US011352414B2

(12) United States Patent
Fallah-Arani et al.

(10) Patent No.: US 11,352,414 B2
(45) Date of Patent: Jun. 7, 2022

(54) MULTIMERIC FC PROTEINS

(71) Applicant: UCB BIOPHARMA SPRL, Brussels (BE)

(72) Inventors: Farnaz Fallah-Arani, Slough (GB); Robert Anthony Griffin, Slough (GB); David Paul Humphreys, Slough (GB); Shirley Jane Peters, Slough (GB); Bryan John Smith, Slough (GB); Paul Edward Stephens, Slough (GB)

(73) Assignee: UCB Biopharma SRL

( * ) Notice: Subject to any disclaimer, the term of this patent is extended or adjusted under 35 U.S.C. 154(b) by 142 days.

(21) Appl. No.: 15/123,038

(22) PCT Filed: Mar. 5, 2015

(86) PCT No.: PCT/EP2015/054687
§ 371 (c)(1),
(2) Date: Sep. 1, 2016

(87) PCT Pub. No.: WO2015/132364
PCT Pub. Date: Sep. 11, 2015

(65) Prior Publication Data
US 2017/0088603 A1   Mar. 30, 2017

(30) Foreign Application Priority Data

Mar. 5, 2014 (GB) .................................. 1403912
Mar. 5, 2014 (GB) .................................. 1403913
Apr. 2, 2014 (GB) .................................. 1405952
Jul. 16, 2014 (GB) .................................. 1412646

(51) Int. Cl.
| C07K 1/00 | (2006.01) |
| A61K 39/00 | (2006.01) |
| C07K 16/00 | (2006.01) |
| C07K 16/46 | (2006.01) |
| C12N 15/62 | (2006.01) |
| C12P 21/02 | (2006.01) |

(52) U.S. Cl.
CPC .............. *C07K 16/00* (2013.01); *C07K 16/46* (2013.01); *C12N 15/62* (2013.01); *C12P 21/02* (2013.01); *A61K 2039/505* (2013.01); *C07K 2317/41* (2013.01); *C07K 2317/52* (2013.01); *C07K 2317/524* (2013.01); *C07K 2317/526* (2013.01); *C07K 2317/528* (2013.01); *C07K 2317/53* (2013.01); *C07K 2317/62* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,677,425 A | 10/1997 | Bodmer |
| 6,475,749 B1 | 11/2002 | Morrison |
| 6,737,056 B1 * | 5/2004 | Presta ................ C07K 16/4291 424/133.1 |
| 6,737,076 B2 | 5/2004 | Fritsche |
| 8,680,237 B2 * | 3/2014 | Strome ................ C07K 16/065 530/350 |
| 2002/0147326 A1 | 10/2002 | Chaikin |
| 2003/0044423 A1 | 3/2003 | Gillies |
| 2004/0175786 A1 | 9/2004 | Choi |
| 2005/0054832 A1 | 3/2005 | Lazar |
| 2006/0134105 A1 | 6/2006 | Lazar |
| 2006/0275283 A1 | 12/2006 | Van Vlijmen |
| 2007/0231329 A1 * | 10/2007 | Lazar ................ C07K 16/2893 424/144.1 |
| 2011/0135662 A1 | 6/2011 | Finney |
| 2017/0081406 A1 | 3/2017 | Fallah-Arani |
| 2017/0088603 A1 * | 3/2017 | Fallah-Arani ........... A61P 37/02 |
| 2018/0044416 A1 | 2/2018 | Humphreys |

FOREIGN PATENT DOCUMENTS

| EP | 0905238 | 3/1999 |
| EP | 2083017 | 7/2009 |
| JP | 2017512063 A | 5/2017 |
| JP | 2018519834 A | 7/2018 |
| WO | 9820734 | 5/1998 |
| WO | 9825971 | 6/1998 |
| WO | 9915549 | 4/1999 |
| WO | 9954484 A1 | 10/1999 |
| WO | 1999051642 | 10/1999 |
| WO | 03010202 | 2/2003 |
| WO | 2004029207 | 4/2004 |
| WO | 2004099249 | 11/2004 |
| WO | 2005003169 | 1/2005 |
| WO | 2005003170 | 1/2005 |
| WO | 2005003171 | 1/2005 |
| WO | 2006019447 | 2/2006 |

(Continued)

OTHER PUBLICATIONS

Braathen et al. The Journal of Biological Chemistry. 277;45:42755-42762. (Year: 2002).*
Xu et al. JBC 1994, 269;5:3469-3474. (Year: 1994).*
Aalberse and Schuurman., "IgG4 breaking the rules," Immunology, vol. 105, No. 1, Jan. 1, 2002, pp. 9-19.
Ananymous, "IgG-Fc Engineering for Therapeutic Use, InvivoGen Insight," InvivoGen, May 1, 2006, pp. 1-4, retrieved from the Internet on May 21, 2015, <http://www.invivogen.com/docs/Insight200605.pdf>.
Angal, S., et al. "A single amino acid substitution abolishes the heterogeneity of chimeric mouse/human (IgG4) antibody", Molecular Immunology, vol. 30, No. 1, pp. 105-108, 1993.

(Continued)

*Primary Examiner* — Chun W Dahle
(74) *Attorney, Agent, or Firm* — Saul Ewing Arnstein & Lehr LLP; Doreen Y. Trujillo

(57) ABSTRACT

The invention relates to multimeric fusion proteins which bind to human Fc receptors. The invention also relates to therapeutic compositions comprising the proteins, and their use in the treatment of immune disorders.

9 Claims, 63 Drawing Sheets

Figure 1:
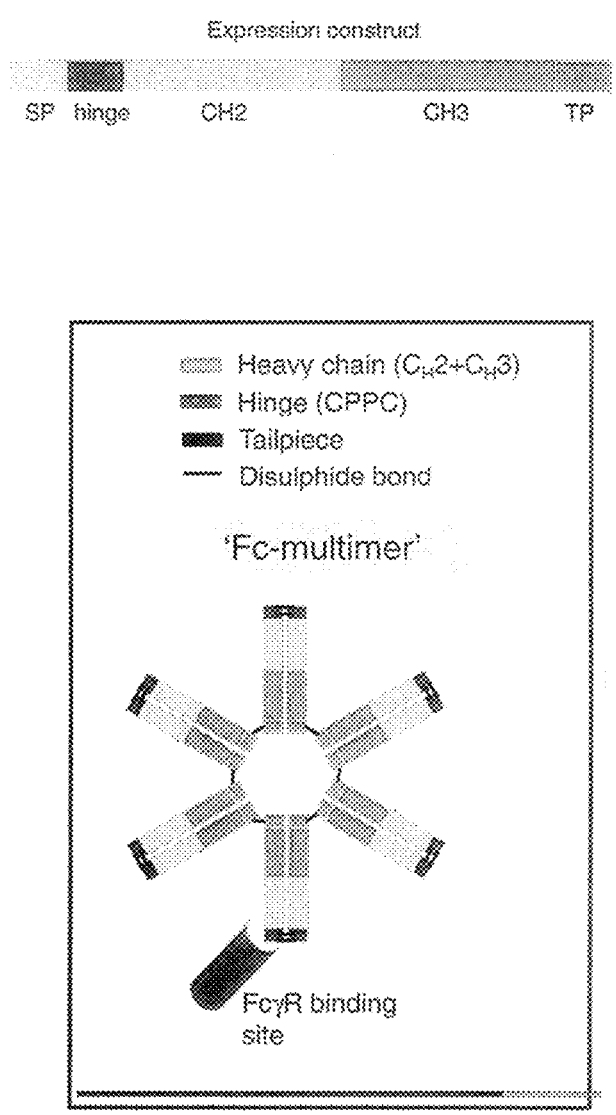

Specification includes a Sequence Listing.

(56) References Cited

FOREIGN PATENT DOCUMENTS

| WO | 2007146968 | | 12/2007 | | |
|---|---|---|---|---|---|
| WO | 2008143954 | | 11/2008 | | |
| WO | 2008151088 | | 12/2008 | | |
| WO | 2009112502 | A1 | 9/2009 | | |
| WO | 2010085682 | A2 | 7/2010 | | |
| WO | 2011073692 | | 6/2011 | | |
| WO | 2012016073 | | 2/2012 | | |
| WO | 2013004842 | | 1/2013 | | |
| WO | 2013049254 | | 4/2013 | | |
| WO | 2013096221 | | 6/2013 | | |
| WO | 2013100702 | | 7/2013 | | |
| WO | 2014006217 | | 1/2014 | | |
| WO | 2014020069 | | 2/2014 | | |
| WO | 2014022592 | | 2/2014 | | |
| WO | 2014031646 | A2 | 2/2014 | | |
| WO | WO-2014022592 | A1 * | 2/2014 | ......... | C07K 16/2878 |
| WO | 2014060712 | | 4/2014 | | |
| WO | 2015132364 | A1 | 9/2015 | | |
| WO | 2015132365 | A1 | 9/2015 | | |
| WO | 2015158867 | A1 | 10/2015 | | |
| WO | 2015168643 | A2 | 11/2015 | | |

OTHER PUBLICATIONS

Augener, "Are Aggregates of IgG the Effective Part of High-Dose Immunoglobulin Therapy in Adult Idiopathic Thrombocytopenic Purpura (ITP)?" Blut, vol. 50, No. 4, p. 249-252, 1985.
Aukrust P et al, "Release of cytokines, soluble cytokine receptors, and interleukin-1 receptor antagonist after intravenous immunoglobulin administration in vivoo," Blood, vol. 84, No. 7, p. 2136-2143, 1994.
Baerenwaldt, "Mechanisms of action of intravenous immunoglobulins," Expert Rev Clin Immunol, vol. 6(3), p. 425-434, 2010.
Bruhns, "Properties of mouse and human IgG receptors and their contribution to disease models," Blood (2012) vol. 119, p. 5640-5649.
Bruhns, P. et a., "Specificity and affinity of human Fcγ receptors and their polymorphic variants for human IgG subclasses," Blood (2009) vol. 113, p. 3716-3725.
Co-pending U.S. Appl. No. 15/123,066, filed Sep. 1, 2016—IFW listing from PAIR only.
Coloma, MJ et al., "The role of carbohydrate in the assembly and function of polymeric IgG", Molecular Immunology (2000); vol. 37, pp. 1081-1090.
Crow, A.R. et al., "The Mechanisms of Action of Intravenous Immunoglobulin and Polyclonal Anti-D Immunoglobulin in the Amelioration of Immune Thrombocytopenic Purpura: What Do We Really Know?" Transfusion Medicine Reviews, vol. 22(2), p. 103-116, 2008.
Dall'Acqua W. F. et al., "Properties of human IgG1s engineered for enhanced binding to the neonatal Fc receptor (FcRn)," Journal of Biological Chemistry, vol. 281, No. 33, Jun. 21, 2006, pp. 23514-23524.
Database Geneseq [Online] May 8, 2003, "Concatameric immunoadhesion human protein sequence Seq ID No. 22.", XP002742050, retrieved from EBI accession No. GSP:ABJ37108, Database accession No. ABJ37108 sequence.
Edelman et al., 1969; "The covalent structure of an entire γG immunoglobulin molecule," PNAS Biochemistry vol. 63 pp. 78-85.
Fridman et al., "Soluble FCγ receptors," (1993) J Leukocyte Biology, vol. 54, No. 5, pp. 504-512.
Garber, E. et al., "A broad range of Fab stabilities within a host of therapeutic IgGs," Biochemical and Biophysical Research Communications, vol. 355, pp. 751-757 (2007).
Ginsberg and Jenson, "Enhancement of platelet response to immune complexes and IgG aggregates by lipid A-rich bacterial lipopolysaccharides," J. Experimental Medicine (1978) vol. 147, No. 1, pp. 207-218.
Hoemberg, "The Isotype of Autoantibodies Influences the Phagocytosis of Antibody Coated Platelets in Autoimmune Thrombocytopenic Purpura ," Scand HJ Immunol, vol. 74, Issue 5, p. 489-495, 2011.

Horsewood, P. et al., "Investigation of the mechanisms of monoclonal antibody-induced platelet activation," Blood, 1991, vol. 78, No. 4, pp. 1019-1026.
Idusogie Esohe et al., "Mapping of the C1q binding site on rituxan, a chimeric antibody with a human IgG1 Fc," The Journal of Immunology, vol. 164, Jan. 1, 2000, pp. 4178-4184.
Imbach, P. et al., "High-Dose Intravenous Gammaglobulin Therapy of Refractory, in Particular Idiopathic Thrombocytopenia in Childhood," Helv Paediatri Acta, vol. 36(1), p. 81-86, 1981.
International Search Report of International Application No. PCT/EP2015/054687 dated Jun. 2, 2015.
International Search Report of International Application No. PCT/EP2015/054688, dated Jul. 1, 2015.
International Search Report of International Application No. PCT/EP2015/058338 dated Jul. 29, 2015.
Kaneko, Y. et al., "Anti-Inflammatory Activity of Immunoglobulin G Resulting from Fc Sialylation," Science, vol. 313, Issue 5787, p. 670-673, 2006.
Langer, F. et al., "The role of CD40 in CD40L- and antibody-mediated platelet activation," Thrombosis and Haemostasis, 2005 vol. 93, pp. 1127-1146.
Levine, R. et al., "How Frequently Is Venous Thromboembolism in Heparin-Treated Patients Associated With Heparin-Induced Thrombocytopenia?" Chest, 2006, vol. 130, Issue 3, pp. 681-687.
Lux et al., "Impact of Immune Complex Size and Glycosylation on IgG Binding to Human FcγRs," J Immunol (2013) vol. 190, No. 8, pp. 4315-4323.
Machino, Y. et al., "Effect of immunoglobulin G (IgG) interchain disulfide bond cleavage on efficacy of intravenous immunoglobulin for immune thrombocytopenic purpura (ITP)," Clin Exp Immunol, vol. 162, No. 3, pp. 415-424, 2010.
Machino, Yusuke et al., "Chemically dimerized intravenous immunoglobulin has potent ameliorating activity in a mouse immune thrombocytopenic purpura model," Biochemical and Biophysical Research Communications, vol. 418, No. 4, p. 748-753, 2012.
Mekhaiel et al; "Polymeric human Fc-fusion proteins with modified effector functions," Nature Scientific Reports 1:124, published Oct. 19, 2011.
Meyer J. et al., "Bevacizumab immune complexes activate platelets and induce thrombosis in FCGR2A transgenic mice," Thrombosis and Haemostasis 2009 7:171-181.
Mollnes, T. et al., "Effect of whole and fractionated intravenous immunoglobulin on complement in vitro," Mol Immunol, vol. 34, Issue 10, p. 719-729, 1997.
Neunert Cindy E, "Current management of immune thrombocytopenia," Hematology / The Education Program of the American Society of Hematology, American Society of Hematology, Education Program 2013, vol. 2013,No. 1, pp. 276-282.
Nimmerjahn and Ravetch, "Anti-Inflammatory Actions of Intravenous Immunoglobulin," Annu Rev Immunol, vol. 26, pp. 513-533, 2008.
Oganesyan Vaheh et al., "Structural characterization of a human Fc fragment engineered for lack of effector functions," ACTS Crystallographica Section D: Biological Crystallography, vol. 64, No. 6, 2008, pp. 700-704.
Proulx, D.P., et al., "Inhibition of B cell-mediated antigen presentation by intravenous immunoglobulins (IVIg)," Clinical Immunology (2010) vol. 135, Iss. 3, pp. 422-429.
Salfeld Jochen G, "Isotype selection in antibody engineering," Nature Biotechnology, vol. 25, No. 12, Dec. 1, 2007, pp. 1369-1372.
Samuelsson, A. et al., "Anti-inflammatory Activity of IVIG Mediated Through the Inhibitory Fc Receptor," Science, vol. 291, Issue 5503, pp. 484-486, 2001.
Scappaticci, F.A. et al., "Arterial Thromboembolic Events in Patients with Metastatic Carcinoma Treated with Chemotherapy and Bevacizumab," 2007 J National Cancer Institute, vol. 99, Issue 16, pp. 1232-1239.
Schwab, I. and Nimmerjahn, "Intravenous immunoglobulin therapy: how does IgG modulate the immune system?" F. Nature Reviews Immunology, vol. 13, Issue 3, pp. 176-189, 2013.
Schwab, I. et al., "IVIg mediated amelioration of ITP in mice is dependent on sialic acid and SIGNR1," European J Immunol, vol. 42, Issue 4, pp. 826-830, 2012.

(56) References Cited

OTHER PUBLICATIONS

Semple, J.W. et al., "Platelets and the immune continuum," Nature Reviews Immunology 2011, vol. 11, Issue 4, pp. 265-274.
Shields R.L. et al, "High resolution mapping of the binding site on human IgG1 for Fc gamma RI, Fc gamma RII, Fc gamma RIII and FcRn and design of IgG1 variants with improved binding to the Fc gamma R," J Biol Chem, vol. 276(9), p. 6591-6604, Mar. 2, 2001.
Siegel, Jerry, "The Product: All Intravenous Immunoglobulins Are Not Equivalent," Pharmacotherapy vol. 25, Issue 11P2, pp. 78S-84S, 2005.
Smith R.I.F. and Morrison, S.L., "Recombinant Polymeric IgG: An Approach to Engineering More Potent Antibodies," Biotechnology, vol. 12, pp. 683-688, 1994.
Smith R.I.F. et al, "Addition of a mu-tailpiece to IgG results in polymeric antibodies with enhanced effector functions including complement-mediated cytolysis," The Journal of Immunology, vol. 154, No. 5, p. 2226-2236, Mar. 1, 1995.
Sondermann, P. et al., "General mechanism for modulating immunoglobulin effector function," PNAS, vol. 110, Issue 24, pp. 9868-9872, 2013.
Sorensen V. et al, "Effect of the IgM and IgA secretory tailpieces on polymerization and secretion of IgM and IgG," The Journal of Immunology, vol. 156, No. 8, p. 2858-2865, Apr. 15, 1996.
Sorensen Vigdis et al., "Structural requirements for incorporation of J chain into human IgM and IgA," International Immunology, vol. 12, No. 2, Jan. 1, 2000, pp. 19-27.
Suntharalingam G et al, "Cytokine Storm in a Phase 1 Trial of the Anti-CD28 Monoclonal Antibody TGN1412," N Engl J Med, vol. 355, Issue 10, pp. 1018-1028, 2006.
Teeling, et al., "Therapeutic efficacy of intravenous immunoglobulin preparations depends on the immunoglobulin G dimers: studies in experimental immune thrombocytopenia," Blood vol. 98(4), p. 1095-1099, 2001.
United Kingdom Search Report dated Dec. 14, 2014 for Application No. GB1403913.5.
United Kingdom Search Report dated Dec. 18, 2014 for Application No. GB1403912.7.
United Kingdom Search Report dated Dec. 18, 2014 for Application No. GB1403914.3.
United Kingdom Search Report dated Dec. 18, 2014 for Application No. GB1403915.0.
United Kingdom Search Report dated Jan. 14, 2015 for Application No. GB1405952.1.
United Kingdom Search Report dated Jan. 15, 2015 for Application No. GB1405955.4.
United Kingdom Search Report dated May 1, 2015 for Application No. GB1412646.0.
United Kingdom Search Report dated May 1, 2015 for Application No. GB1412648.6.
Written Opinion of the International Searching Authority for International Application No. PCT/EP2015/054687 dated Jun. 2, 2015.
Written Opinion of the International Searching Authority for International Application No. PCT/EP2015/054688, dated Jul. 1, 2015.
Written Opinion of the International Searching Authority for International Application No. PCT/EP2015/058338 dated Jul. 29, 2015.
Yoo, E.M. et al., "Structural Requirements for Polymeric Immunoglobulin Assembly and Association with J Chain," Journal of Biological Chemistry, vol. 274, No. 47, Nov. 19, 1999, pp. 33771-33777.
United Kingdom Search Report dated Jan. 27, 2015 for Application No. GB1406894.4.
United Kingdom Search Report dated Jul. 22, 2015 for Application No. GB1412649.4.
Office Action, Japanese Patent Application No. 2016-55557, dated Mar. 19, 2019.
Office Action, U.S. Appl. No. 15/554,478, dated May 21, 2020.
Co-pending U.S. Appl. No. 15/741,590, filed Jan. 3, 2018.
Co-pending U.S. Appl. No. 15/554,478, filed Aug. 30, 2017.
Sitia, R., et al., "Developmental Regulation of IgM Secretion: The Role of the Carboxy-Terminal Cysteine", Cell (1990), vol. 60, pp. 781-790.
Office Action, Japanese Patent Application No. 2018-500473 dated Jun. 16, 2020.
Translation of Office Action, Japanese Patent Application No. 2018-500473 dated Jun. 16, 2020.
Carter, "Bispecific Human IgG by Design," Journal of Immunol. Methods 248(1-2): 7-15 (2001).
Czajkowsky et al., "Fc-fusion proteins: new developments and future perspectives," EMBO Molecular Medicine 4(10):1015-1028 (2012).
Davis et al., "Intermolecular Disulfide Bonding in IgM: Effects of Replacing Cysteine Residues in the Mu Heavy Chain," EMBO Journal 8(9): 2519-2526 (1989).
Diebolder et al., "Complement is Activated by IgG Hexamers Assembled at the Cell Surface," Science, 343(6176):1260-1263 (2014).
Finco et al., "Cytokine release assays: Current practices and future directions," Cytokine 66(2): 143-155 (2014).
Jain et al., "Fully Recombinant IgG2a Fc Multimers (Stradomers) Effectively Treat Collagen-Induced Arthritis and Prevent Idiopathic Thrombocytopenic Purpura in Mice," Arthritis Research and Therapy 14: 1-12 (2012).
De Jong et al., "A Novel Platform for the Potentiation of Therapeutic Antibodies Based on Antigen-Dependent Formation of IgG Hexamers at the Cell Surface," PLoS Biol 14(1): e1002344 (2016).
Klein et al., "Progress in Overcoming the Chain Association Issue in Bispecific Heterodimeric IgG Antibodies," MAbs 4(6): 653-663 (2012).
Nagashima et al., "Tandemly Repeated Fc Domain Augments Binding Avidities of Antibodies for Fcgamma Receptors, Resulting in Enhanced Antibody-dependent Cellular Cytotoxicity," Molecular Immunology 45(10): 2752-2763 (2008).
Von Kreudenstein et al., "Improving Biophysical Properties of a Bispecific Antibody Scaffold to Aid Developabililty," mAbs 5(5): 646-654 (2013).
Youd et al., "IgM Monomers Accelerate Disease Manifestations in Autoimmune-prone Fas-deficient Mice," Journal of Autoimmunity 23: 333-343 (2004).
International Search Report and Written Opinion dated Jun. 26, 2016 for International Application No. PCT/EP2016/054718 filed Mar. 4, 2016, 22 pages.
United Kingdom Search Report dated Nov. 30, 2015 for Application No. GB1503778.1.
Japanese Office Action in JP 2016-555527 dated Mar. 19, 2019.
Japanese Office Action in JP 2018-500473 dated Jun. 16, 2020.
Mekhaiel et al., "Polymeric human Fc-fusion proteins with modified effector functions," Scientific Reports 1 (19):(2011).
International Search Report for PCT/EP2016/065914, dated Oct. 4, 2016.
Co-pending U.S. Appl. No. 17/098,734, filed Nov. 16, 2020.
Japanese Office Action in JP 2016-555527 dated Mar. 19, 2019 English Translation.
Japanese Office Action in JP 2018-500473 dated Jun. 16, 2020 English Translation.
Vafa, O., et al., "An engineered Fc variant of an IgG eliminates all immune effector functions via structural perturbations", Methods 65 (2014) 114-126.
Office Action, Japanese Patent Application No. 2017-546686 dated Sep. 11, 2020.
Translation of Office Action, Japanese Patent Application No. 2017-546686 dated Sep. 11, 2020.
Communication pursuant to Article 94(3) EPC, European Patent Application No. 16707827.8, dated Oct. 19, 2020.
Brunke, C., "Effect of a tail piece cysteine deletion on biochemical and functional properties of an epidermal growth factor receptor-directed IgA2 m(1) antibody", mAbs 5:6, 936-945, Nov./Dec. 2013.
Office Action, Chinese Patent Application No. 201680039811.X, dated Dec. 24, 2020.
English Translation of Office Action, Chinese Patent Application No. 201680039811.X, dated Dec. 24, 2020.

(56) References Cited

OTHER PUBLICATIONS

Search Report, Chinese Patent Application No. 201680039811.X, dated Dec. 24, 2020.
English Translation of Search Report, Chinese Patent Application No. 201680039811.X, dated Dec. 24, 2020.
Japanese Office Action for App. No. JP2018-500473, dated Jun. 8, 2021, 12 pages.
Muller, R. et al., "High-resolution structures of the IgM Fc domains reveal principles of its hexamer formation", Proc Natl acad Sci, USA, (2013) vol. 110, No. 25, pp. 10183-10188.
Nagaoka et al., "Single amino acid substitution in the mouse IgG1 Fc region induces drastic enhancement of the affinity to protein A", Protein Eng., (2003) vol. 16, No. 4, pp. 243-245.
Japanese Office Action for App. No. JP2018-500473, dated Jun. 8, 2021 English translation, 13 pages.

* cited by examiner

Figure 2a

1.  Human IgG1 Fc-multimer IgM tp    SEQ ID NO: 26

CPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGKPTLYNVSLVMSDTAGTCY

2.  Human IgG4 Fc-multimer IgM tp    SEQ ID NO: 27

CPPCPAPEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLYSRLT
VDKSRWQEGNVFSCSVMHEALHNHYTQKSLSLSLGKPTLYNVSLVMSDTAGTCY

3.  Human IgG1 Fc-multimer IgA tp    SEQ ID NO: 28

CPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGKPTHVNVSVVMAEVDGTCY

4.  Human IgG4 Fc-multimer IgA tp    SEQ ID NO: 29

CPPCPAPEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLYSRLT
VDKSRWQEGNVFSCSVMHEALHNHYTQKSLSLSLGKPTHVNVSVVMAEVDGTCY

5.  Human IgG1 Fc-multimer Cμ4-IgM tp    SEQ ID NO: 30

CPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK*VALHRPDVYLLPPAREQLNLRESATI*
*TCLVTGFSPADVFVQWMQRGQPLSPEKYVTSAPMPEPQAPGRYFAHSILTVSEEEWNTGETY*
*TCVAHEALPNRVTERTVDKSTGK*PTLYNVSLVMSDTAGTCY

Figure 2a continued

6. Human IgG4 Fc-multimer Cµ4-IgM tp    SEQ ID NO: 31

CPPCPAPEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLYSRLT
VDKSRWQEGNVFSCSVMHEALHNHYTQKSLSLSLGK*VALHRPDVYLLPPAREQLNLRESATI
TCLVTGFSPADVFVQWMQRGQPLSPEKYVTSAPMPEPQAPGRYFAHSILTVSEEEWNTGETY
TCVAHEALPNRVTERTVDKSTGK*<u>*PTLYNVSLVMSDTAGTCY*</u>

7. Human IgG1 Fc-multimer IgM tp S267A    SEQ ID NO: 32

CPPCPAPELLGGPSVFLFPPKPKDTLMISRTPEVTCVVVDV<u>A</u>HEDPEVKFNWYVDGVEVHNA
KTKPREEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK<u>PTLYNVSLVMSDTAGTCY</u>

Figure 2b

IgG1 Fc IgM tp    SEQ ID NO: 33

CPPCPAPE*L GGPSVFLFPP KPKDTLMISR TPEVTCVVVD VS*EDPEV*F NWYVDGVEV
H NAKTKPREEQ *NSTYRVVSV LTVLHQDWLN GKEYKCKVSN K*LP**IEKT ISKAKGQ
PRE PQVYTLPPS* **TKNQVSL TCLVKGFYPS DIAVEWESNG QPENNYKTTP PVLDS
DGSFF LYS*LTVDKS RWQ*GNVFSC SVMHEALHNH YTQKSLSLS* GKPTLYNVSL VMS
DTAGTCY

IgG4 Fc IgM tp    SEQ ID NO: 34

CPPCPAPE*L GGPSVFLFPP KPKDTLMISR TPEVTCVVVD VS*EDPEV*F NWYVDGVEV
H NAKTKPREEQ *NSTYRVVSV LTVLHQDWLN GKEYKCKVSN K*LP**IEKT ISKAKGQ
PRE PQVYTLPPS* **TKNQVSL TCLVKGFYPS DIAVEWESNG QPENNYKTTP PVLDS
DGSFF LYS*LTVDKS RWQ*GNVFSC SVMHEALHNH YTQKSLSLS* GKPTLYNVSL VMS
DTAGTCY

Figure 2c

`IgG1 Fc IgM tp L234F` SEQ ID NO: 35

CPPCPAPEFL GGPSVFLFPP KPKDTLMISR TPEVTCVVVD VSHEDPEVKF NWYVDGVEV
H NAKTKPREEQ YNSTYRVVSV LTVLHQDWLN GKEYKCKVSN KALPAPIEKT ISKAKGQ
PRE PQVYTLPPSR DELTKNQVSL TCLVKGFYPS DIAVEWESNG QPENNYKTTP PVLDS
DGSFF LYSKLTVDKS RWQQGNVFSC SVMHEALHNH YTQKSLSLSP GKPTLYNVSL VMS
DTAGTCY

`IgG1 Fc IgM tp L234F P331S` SEQ ID NO: 36

CPPCPAPEFL GGPSVFLFPP KPKDTLMISR TPEVTCVVVD VSHEDPEVKF NWYVDGVEV
H NAKTKPREEQ YNSTYRVVSV LTVLHQDWLN GKEYKCKVSN KALPASIEKT ISKAKGQ
PRE PQVYTLPPSR DELTKNQVSL TCLVKGFYPS DIAVEWESNG QPENNYKTTP PVLDS
DGSFF LYSKLTVDKS RWQQGNVFSC SVMHEALHNH YTQKSLSLSP GKPTLYNVSL VMS
DTAGTCY

`IgG4 Fc IgM tp F234L` SEQ ID NO: 37

CPPCPAPELL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KGLPSSIEKT ISKAKGQ
PRE PQVYTLPPSQ EEMTKNQVSL TCLVKGFYPS DIAVEWESNG QPENNYKTTP PVLDS
DGSFF LYSRLTVDKS RWQEGNVFSC SVMHEALHNH YTQKSLSLSL GKPTLYNVSL VMS
DTAGTCY

`IgG4 Fc IgM tp F234L F296Y` SEQ ID NO: 38

CPPCPAPELL GGPSVFLFPP KPKDTLMISR TPEVTCVVVD VSQEDPEVQF NWYVDGVEV
H NAKTKPREEQ YNSTYRVVSV LTVLHQDWLN GKEYKCKVSN KGLPSSIEKT ISKAKGQ
PRE PQVYTLPPSQ EEMTKNQVSL TCLVKGFYPS DIAVEWESNG QPENNYKTTP PVLDS
DGSFF LYSRLTVDKS RWQEGNVFSC SVMHEALHNH YTQKSLSLSL GKPTLYNVSL VMS
DTAGTCY

Figure 2c continued

IgG4 Fc IgM tp G327A S330A   SEQ ID NO: 39

CPPCPAPEFL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KALPASIEKT ISKAKGQ
PRE PQVYTLPPSQ EEMTKNQVSL TCLVKGFYPS DIAVEWESNG QPENNYKTTP PVLDS
DGSFF LYSRLTVDKS RWQEGNVFSC SVMHEALHNH YTQKSLSLSL GKPTLYNVSL VMS
DTAGTCY

IgG4 Fc IgM tp G327A S331P   SEQ ID NO: 40

CPPCPAPEFL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KALPSPIEKT ISKAKGQ
PRE PQVYTLPPSQ EEMTKNQVSL TCLVKGFYPS DIAVEWESNG QPENNYKTTP PVLDS
DGSFF LYSRLTVDKS RWQEGNVFSC SVMHEALHNH YTQKSLSLSL GKPTLYNVSL VMS
DTAGTCY

IgG4 Fc IgM tp S330A S331P   SEQ ID NO: 41

CPPCPAPEFL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KGLPAPIEKT ISKAKGQ
PRE PQVYTLPPSQ EEMTKNQVSL TCLVKGFYPS DIAVEWESNG QPENNYKTTP PVLDS
DGSFF LYSRLTVDKS RWQEGNVFSC SVMHEALHNH YTQKSLSLSL GKPTLYNVSL VMS
DTAGTCY

Figure 2d

IgG1 CH2 IgG4 CH3 IgM tp    SEQ ID NO: 42

CPPCPAPELL GGPSVFLFPP KPKDTLMISR TPEVTCVVVD VSHEDPEVKF NWYVDGVEV
H NAKTKPREEQ YNSTYRVVSV LTVLHQDWLN GKEYKCKVSN KALPAPIEKT ISKAKGQ
PRE PQVYTLPPSQ EEMTKNQVSL TCLVKGFYPS DIAVEWESNG QPENNYKTTP PVLDS
DGSFF LYSRLTVDKS RWQEGNVFSC SVMHEALHNH YTQKSLSLSL GKPTLYNVSL VMS
DTAGTCY

IgG4 CH2 IgG1 CH3 IgM tp    SEQ ID NO: 43

CPPCPAPEFL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KGLPSSIEKT ISKAKGQ
PRE PQVYTLPPSR DELTKNQVSL TCLVKGFYPS DIAVEWESNG QPENNYKTTP PVLDS
DGSFF LYSKLTVDKS RWQQGNVFSC SVMHEALHNH YTQKSLSLSP GKPTLYNVSL VMS
DTAGTCY

Figure 2e

IgG4 CH2 / IgG1 CH3 hybrid IgM tp F234L    SEQ ID NO: 44

CPPCPAPEFL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KGLPSSIEKT ISKAKGQ
PRE PQVYTLPPSR DELTKNQVSL TCLVKGFYPS DIAVEWESNG QPENNYKTTP PVLDS
DGSFF LYSKLTVDKS RWQQGNVFSC SVMHEALHNH YTQKSLSLSP GKPTLYNVSL VMS
DTAGTCY

IgG4 CH2 / IgG1 CH3 hybrid IgM tp G327A S331P    SEQ ID NO: 45

CPPCPAPEFL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KALPSPIEKT ISKAKGQ
PRE PQVYTLPPSR DELTKNQVSL TCLVKGFYPS DIAVEWESNG QPENNYKTTP PVLDS
DGSFF LYSKLTVDKS RWQQGNVFSC SVMHEALHNH YTQKSLSLSP GKPTLYNVSL VMS
DTAGTCY

IgG4 CH2 / IgG1 CH3 hybrid IgM tp F234L F296Y    SEQ ID NO: 46

CPPCPAPEFL GGPSVFLFPP KPKDTLMISR TPEVTCVVVD VSQEDPEVQF NWYVDGVEV
H NAKTKPREEQ YNSTYRVVSV LTVLHQDWLN GKEYKCKVSN KGLPSSIEKT ISKAKGQ
PRE PQVYTLPPSR DELTKNQVSL TCLVKGFYPS DIAVEWESNG QPENNYKTTP PVLDS
DGSFF LYSKLTVDKS RWQQGNVFSC SVMHEALHNH YTQKSLSLSP GKPTLYNVSL VMS
DTAGTCY

Figure 2e continued

IgG4 CH2 / IgG1 CH3 hybrid IgM tp G327A S330A    SEQ ID NO: 47

CPPCPAPEFL GGPSVFLFPP KPKDTLMISR TPEVTCVVVD VSQEDPEVQF NWYVDGVEV
H NAKTKPREEQ FNSTYRVVSV LTVLHQDWLN GKEYKCKVSN KALPASIEKT ISKAKGQ
PRE PQVYTLPPSR DELTKNQVSL TCLVKGFYPS DIAVEWESNG QPENNYKTTP PVLDS
DGSFF LYSKLTVDKS RWQQGNVFSC SVMHEALHNH YTQKSLSLSP GKPTLYNVSL VMS
DTAGTCY

Figure 2f

(i)

atggaatggtcctgggtcttcctgttttcctttctgtcacaaccggggtgcacagc

SEQ ID NO: 48

(ii)

MEWSWVFLFFLSVTTGVHS   SEQ ID NO: 49

Figure 2g

IgG1 Fc IgM tp L309  SEQ ID NO: 50 tgcccaccgtgcccagcacctgaactcctggggggaccgtcagtcttcctcttccccccaaa
acccaaggacaccctcatgatctcccggacccctgaggtcacatgcgtggtggtggacgtga
gccacgaagaccctgaggtcaagttcaactggtacgtggacggcgtggaggtgcataatgcc
aagacaaagccgcgggaggagcagtacaacagcacgtaccgtgtggtcagcgtcctcaccgt
cctgcaccaggactggctgaatggcaaggagtacaagtgcaaggtctccaacaaagccctcc
cagcccccatcgagaaaccatctccaaagccaaagggcagccccgagaaccacaggtgtac
accctgcccccatcccgggatgagctgaccaagaaccaggtcagcctgacctgcctggtcaa
aggcttctatccagcgacatcgccgtggagtgggagagcaatgggcagccggagaacaact
acaagaccacgcctcccgtgctggactccgacggctccttcttcctctacagcaagctcacc
gtggacaagagcaggtggcagcaggggaacgtcttctcatgctccgtgatgcatgaggctct
gcacaaccactacacgcagaagagcctctccctgtctccgggtaaaccgaccctgtataacg
tgagcctggtgatgagcgataccgcgggcacctgctat

IgG4 Fc IgM tp L309  SEQ ID NO: 51 tgtccaccttgtccagctcctgagtttcttggcggtccttctgtgttcctcttccctccaaa
gcctaaggacaccctgatgatctccagaacaccagaagtgacctgcgtggtagtggatgtta
gccaggaagaccctgaggtccagttcaactggtatgtggacggcgttgaggtccataacgcc
aaaaccaagccacgagaggagcagttcaactcaacctaccgtgtggtgtctgtgctcactgt
cctgcatcaggattggctgaacggcaaggagtacaagtgcaaggtcagcaacaagggactgc
caagctccatcgagaagaccattagcaaagccaagggtcagcctagggaaccacaggtgtat
acattgcctccctcaggaggagatgaccaagaaccaggtcagtctgacatgcctggtgaa
aggttctatccctccgatatcgcagtcgaatgggaaagcaatggccagcctgagaacaact
acaaaaccactccacccgtccttgatagcgatggcagtttcttcctgtacagccgtctgact
gtggataagtctcgatggcaggagggtaacgtattcagctgcagcgtcatgcatgaagcctt
gcacaaccactacacccagaaatccctgtctctgtcactcgggaagccgaccctgtataacg
tgagcctggtgatgagcgataccgcgggcacctgctat

Figure 2g continued

IgG1 Fc IgM tp L309 L234F P331S    SEQ ID NO: 52 tgcccaccgtgcccagcacctgaattcctgggggaccgtcagtcttcctcttccccccaaa
acccaaggacaccctcatgatctcccggacccctgaggtcacatgcgtggtggtggacgtga
gccacgaagaccctgaggtcaagttcaactggtacgtggacggcgtggaggtgcataatgcc
aagacaaagccgcgggaggagcagtacaacagcacgtaccgtgtggtcagcgtcctcaccgt
cctgcaccaggactggctgaatggcaaggagtacaagtgcaaggtctccaacaaagccctcc
cagccagcatcgagaaaaccatctccaaagccaaagggcagccccgagaaccacaggtgtac
accctgcccccatcccgggatgagctgaccaagaaccaggtcagcctgacctgcctggtcaa
aggcttctatcccagcgacatcgccgtggagtgggagagcaatgggcagccggagaacaact
acaagaccacgcctcccgtgctggactccgacggctccttcttcctctacagcaagctcacc
gtggacaagagcaggtggcagcaggggaacgtcttctcatgctccgtgatgcatgaggctct
gcacaaccactacacgcagaagagcctctccctgtctccgggtaaaccgaccctgtataacg
tgagcctggtgatgagcgataccgcgggcacctgctat

Hybrid Fc IgG4-CH2 IgG1-CH3 IgM tp L309    SEQ ID NO: 53 tgcccaccgtgcccagcacctgagttcctgggggaccatcagtcttcctgttccccccaaa
acccaaggacactctcatgatctcccggacccctgaggtcacgtgcgtggtggtggacgtga
gccaggaagaccccgaggtccagttcaactggtacgtggatggcgtggaggtgcataatgcc
aagacaaagccgcgggaggagcagttcaacagcacgtaccgtgtggtcagcgtcctcaccgt
cctgcaccaggactggctgaacggcaaggagtacaagtgcaaggtctccaacaaaggcctcc
cgtcctccatcgagaaaaccatctccaaagccaaagggcagccccgagaaccacaggtgtac
accctgcccccatcccgggatgagctgaccaagaaccaggtcagcctgacctgcctggtcaa
aggcttctatcccagcgacatcgccgtggagtgggagagcaatgggcagccggagaacaact
acaagaccacgcctcccgtgctggactccgacggctccttcttcctctacagcaagctcacc
gtggacaagagcaggtggcagcaggggaacgtcttctcatgctccgtgatgcatgaggctct
gcacaaccactacacgcagaagagcctctccctgtctccgggtaaaccgaccctgtataacg
tgagcctggtgatgagcgataccgcgggcacctgctat

Figure 2g continued

IgG4 Fc IgM tp L309 F234L      SEQ ID NO: 54 tgtccaccttgtccagctcctgagttacttggcggtccttctgtgttcctcttccctccaaa
gcctaaggacaccctgatgatctccagaacaccagaagtgacctgcgtggtagtggatgtta
gccaggaagaccctgaggtccagttcaactggtatgtggacggcgttgaggtccataacgcc
aaaaccaagccacgagaggagcagttcaactcaacctaccgtgtggtgtctgtgctcactgt
cctgcatcaggattggctgaacggcaaggagtacaagtgcaaggtcagcaacaagggactgc
caagctccatcgagaagaccattagcaaagccaagggtcagcctagggaaccacaggtgtat
acattgcctcctcacaggaggagatgaccaagaaccaggtcagtctgacatgcctggtgaa
agggttctatcctccgatatcgcagtcgaatgggaaagcaatggccagcctgagaacaact
acaaaaccactccacccgtccttgatagcgatggcagtttcttcctgtacagccgtctgact
gtggataagtctcgatggcaggagggtaacgtattcagctgcagcgtcatgcatgaagcctt
gcacaaccactacacccagaaatccctgtctctgtcactcgggaagccgaccctgtataacg
tgagcctggtgatgagcgataccgcgggcacctgctat

IgG4 Fc IgM tp L309 F234L F296Y      SEQ ID NO: 55 tgtccaccttgtccagctcctgagttacttggcggtccttctgtgttcctcttccctccaaa
gcctaaggacaccctgatgatctccagaacaccagaagtgacctgcgtggtagtggatgtta
gccaggaagaccctgaggtccagttcaactggtatgtggacggcgttgaggtccataacgcc
aaaaccaagccacgagaggagcagtataactcaacctaccgtgtggtgtctgtgctcactgt
cctgcatcaggattggctgaacggcaaggagtacaagtgcaaggtcagcaacaagggactgc
caagctccatcgagaagaccattagcaaagccaagggtcagcctagggaaccacaggtgtat
acattgcctcctcacaggaggagatgaccaagaaccaggtcagtctgacatgcctggtgaa
agggttctatcctccgatatcgcagtcgaatgggaaagcaatggccagcctgagaacaact
acaaaaccactccacccgtccttgatagcgatggcagtttcttcctgtacagccgtctgact
gtggataagtctcgatggcaggagggtaacgtattcagctgcagcgtcatgcatgaagcctt
gcacaaccactacacccagaaatccctgtctctgtcactcgggaagccgaccctgtataacg
tgagcctggtgatgagcgataccgcgggcacctgctat

Figure 2g continued

IgG4 Fc IgM tp L309 G327A S330A      SEQ ID NO: 56 tgtccaccttgtccagctcctgagtttcttggcggtccttctgtgttcctcttccctccaaa
gcctaaggacaccctgatgatctccagaacaccagaagtgacctgcgtggtagtggatgtta
gccaggaagaccctgaggtccagttcaactggtatgtggacggcgttgaggtccataacgcc
aaaaccaagccacgagaggagcagttcaactcaacctaccgtgtggtgtctgtgctcactgt
cctgcatcaggattggctgaacggcaaggagtacaagtgcaaggtcagcaacaaggcactgc
cagcctccatcgagaagaccattagcaaagccaagggtcagcctagggaaccacaggtgtat
acattgcctcctcacaggaggagatgaccaagaaccaggtcagtctgacatgcctggtgaa
agggttctatcctccgatatcgcagtcgaatgggaaagcaatggccagcctgagaacaact
acaaaaccactccacccgtccttgatagcgatggcagtttcttcctgtacagccgtctgact
gtggataagtctcgatggcaggagggtaacgtattcagctgcagcgtcatgcatgaagcctt
gcacaaccactacacccagaaatccctgtctctgtcactcgggaagccgaccctgtataacg
tgagcctggtgatgagcgataccgcgggcacctgctat

IgG4 Fc IgM tp L309 G327A S331P      SEQ ID NO: 57 tgtccaccttgtccagctcctgagtttcttggcggtccttctgtgttcctcttccctccaaa
gcctaaggacaccctgatgatctccagaacaccagaagtgacctgcgtggtagtggatgtta
gccaggaagaccctgaggtccagttcaactggtatgtggacggcgttgaggtccataacgcc
aaaaccaagccacgagaggagcagttcaactcaacctaccgtgtggtgtctgtgctcactgt
cctgcatcaggattggctgaacggcaaggagtacaagtgcaaggtcagcaacaaggcactgc
caagcccatcgagaagaccattagcaaagccaagggtcagcctagggaaccacaggtgtat
acattgcctcctcacaggaggagatgaccaagaaccaggtcagtctgacatgcctggtgaa
agggttctatcctccgatatcgcagtcgaatgggaaagcaatggccagcctgagaacaact
acaaaaccactccacccgtccttgatagcgatggcagtttcttcctgtacagccgtctgact
gtggataagtctcgatggcaggagggtaacgtattcagctgcagcgtcatgcatgaagcctt
gcacaaccactacacccagaaatccctgtctctgtcactcgggaagccgaccctgtataacg
tgagcctggtgatgagcgataccgcgggcacctgctat

Figure 2g continued

IgG4 Fc IgM tp L309 S330A S331P        SEQ ID NO: 58 tgtccaccttgtccagctcctgagtttcttggcggtccttctgtgttcctcttccctccaaa
gcctaaggacaccctgatgatctccagaacaccagaagtgacctgcgtggtagtggatgtta
gccaggaagaccctgaggtccagttcaactggtatgtggacggcgttgaggtccataacgcc
aaaaccaagccacgagaggagcagttcaactcaacctaccgtgtggtgtctgtgctcactgt
cctgcatcaggattggctgaacggcaaggagtacaagtgcaaggtcagcaacaagggactgc
cagcccccatcgagaagaccattagcaaagccaagggtcagcctagggaaccacaggtgtat
acattgcctcctcacaggaggagatgaccaagaaccaggtcagtctgacatgcctggtgaa
agggttctatcctccgatatcgcagtcgaatgggaaagcaatggccagcctgagaacaact
acaaaaccactccaccgtccttgatagcgatggcagtttcttcctgtacagccgtctgact
gtggataagtctcgatggcaggagggtaacgtattcagctgcagcgtcatgcatgaagcctt
gcacaaccactacacccagaaatccctgtctctgtcactcgggaagccgaccctgtataacg
tgagcctggtgatgagcgataccgcgggcacctgctat

IgG4 CH2-IgG1 CH3 IgM tp L309 F234L F296Y        SEQ ID NO: 59 tgcccaccgtgcccagcacctgagttactggggggaccatcagtcttcctgttccccccaaa
acccaaggacactctcatgatctcccggacccctgaggtcacgtgcgtggtggtggacgtga
gccaggaagaccccgaggtccagttcaactggtacgtggatggcgtggaggtgcataatgcc
aagacaaagccgcgggaggagcagtataacagcacgtaccgtgtggtcagcgtcctcaccgt
cctgcaccaggactggctgaacggcaaggagtacaagtgcaaggtctccaacaaaggcctcc
cgtcctccatcgagaaaaccatctccaaagccaaagggcagccccgagaaccacaggtgtac
accctgcccccatcccgggatgagctgaccaagaaccaggtcagcctgacctgcctggtcaa
aggcttctatcccagcgacatcgccgtggagtgggagagcaatgggcagccggagaacaact
acaagaccacgcctcccgtgctggactccgacggctccttcttcctctacagcaagctcacc
gtggacaagagcaggtggcagcaggggaacgtcttctcatgctccgtgatgcatgaggctct
gcacaaccactacacgcagaagagcctctccctgtctccgggtaaaccgaccctgtataacg
tgagcctggtgatgagcgataccgcgggcacctgctat

- △ IgG4 Fc IgM tp L309
- ▲ IgG1 Fc IgM tp L309
- ⊙ IgG1 Fc IgM tp L309 L234F

- △ IgG4 Fc IgM tp L309
- ▲ IgG1 Fc IgM tp L309
- ⊙ IgG1 Fc IgM tp L309 H268Q

△ IgG4 Fc IgM tp L309
▲ IgG1 Fc IgM tp L309
○ IgG1 Fc IgM tp L309 P331S

△ IgG4 Fc IgM tp L309
▲ IgG1 Fc IgM tp L309
○ IgG1 Fc IgM tp L309 K409R

- ▲ IgG1 Fc IgM tp L309
- △ IgG4 Fc IgM tp L309
- ○ IgG4 Fc IgM tp L309 S331P

- ▲ IgG1 Fc IgM tp L309
- △ IgG4 Fc IgM tp L309
- ○ IgG4 Fc IgM tp L309 R409K

- ▲ IgG1 Fc IgM tp L309
- △ IgG4 Fc IgM tp L309
- ○ IgG4 Fc IgM tp L309 F234L F296Y

- ▲ IgG1 Fc IgM tp L309
- △ IgG4 Fc IgM tp L309
- ○ IgG4 Fc IgM tp L309 G327A S331P (a)

(b)

MULTIMERIC FC PROTEINS

CROSS-REFERENCE TO RELATED APPLICATIONS

The present application is a U.S. National Phase entry under 35 U.S.C. § 371 of PCT International Application No. PCT/EP2015/054687, filed Mar. 5, 2015, which claims the benefit of priority under 35 U.S.C. § 119 of British Application No. 1403912.7, filed Mar. 5, 2014, British Application No. 1403913.5, filed Mar. 5, 2014, British Application No. 1405952.1, filed Apr. 2, 2014, British Application No. 1412646.0, filed Jul. 16, 2014, all of which are incorporated by reference in their entireties.

The invention relates to multimeric fusion proteins which bind to human Fc-receptors. The invention also relates to therapeutic compositions comprising the multimeric fusion proteins, and their use in the treatment of immune disorders.

BACKGROUND

Immune disorders encompass a wide variety of diseases with different signs, symptoms, etiologies and pathogenic mechanisms. Many of these diseases are characterised by the active involvement of pathogenic antibodies and/or pathogenic immune complexes. In some diseases such as ITP (variably called immune thrombocytopenia, immune thrombocytic purpura, idiopathic thrombocytopenic purpura) the target antigens for the pathogenic antibodies (Hoemberg, Scand H J Immunol, Vol 74(5), p 489-495, 2011) and disease process are reasonably well understood. Such immune disorders are often treated with a variety of conventional agents, either as monotherapy or in combination. Examples of such agents are corticosteroids, which are associated with numerous side effects, intravenous immunoglobulin (IVIG) and anti-D.

Antibodies, often referred to as immunoglobulins, are Y-shaped molecules comprising two identical heavy (H) chains and two identical light (L) chains, held together by interchain disulphide bonds. Each chain consists of one variable domain (V) that varies in sequence and is responsible for antigen binding. Each chain also consists of at least one constant domain (C). In the light chain there is a single constant domain. In the heavy chain there are at least three, sometimes four constant domains, depending on the isotype (IgG, IgA and IgD have three, IgM and IgE have four).

In humans there are five different classes or isotypes of immunoglobulins termed IgA, IgD, IgE, IgG and IgM. All these classes have the basic four-chain Y-shaped structure, but they differ in their heavy chains, termed $\alpha$, $\delta$, $\epsilon$, $\gamma$ and $\mu$ respectively. IgA can be further subdivided into two sub-classes, termed IgA1 and IgA2. There are four sub-classes of IgG, termed IgG1, IgG2, IgG3 and IgG4.

The Fc-domain of an antibody typically comprises at least the last two constant domains of each heavy chain which dimerise to form the Fc domain. The Fc domain is responsible for providing antibody effector functions, including determining antibody half-life, principally through binding to FcRn, distribution throughout the body, ability to fix complement, and binding to cell surface Fc receptors.

The differences between antibody isotypes are most pronounced in the Fc-domains, and this leads to the triggering of different effector functions on binding to antigen. Structural differences also lead to differences in the polymerisation state of the antibodies. Thus IgG, IgE and IgD are generally monomeric whereas IgM occurs as both a pentamer and a hexamer, IgA occurs predominantly as a monomer in serum and as a dimer in sero-mucous secretions.

Intravenous immunoglobulin (IVIG) is the pooled immunoglobulin from thousands of healthy blood donors. IVIG was initially used as an IgG replacement therapy to prevent opportunistic infections in patients with low IgG levels (reviewed in Baerenwaldt, Expert Rev Clin Immunol, Vol 6(3), p 425-434, 2010). After discovery of the anti-inflammatory properties of IVIG in children with ITP (Imbach, Helv Paediatri Acta, Vol 36(1), p 81-86, 1981), IVIG is now licensed for the treatment of ITP, Guillain-Barré syndrome, Kawasaki disease, and chronic inflammatory demyelinating polyneuropathy (Nimmerjahn, Annu Rev Immunol, Vol 26, p 513-533, 2008).

In diseases involving pathogenic immune complexes it has been proposed that a minority fraction of the component immunoglobulin fraction is disproportionately effective. It is observed that traces (typically 1-5%) of IgG are present in multimeric forms within IVIG. The majority of this multimeric fraction is thought to be dimer with smaller amounts of trimer and higher forms. It has also been proposed that additional dimers may form after infusion by binding of recipient anti-idiotype antibodies. One theory is that these multimeric forms compete against immune complexes for binding to low affinity Fc$\gamma$ receptors due to their enhanced avidity (Augener, Blut, Vol 50, p 249-252, 1985; Teeling, Blood Vol 98(4), p 1095-1099, 2001; Machino, Y., Clin Exp Immunol, Vol 162(3), p 415-424, 2010; Machino, Y. et al., BBRC, Vol 418, p 748-753, 2012). Another theory is that sialic acid glycoforms of IgG within IVIG, especially the presence of higher levels of $\alpha$2-6 sialic acid forms, cause an alteration in Fc$\gamma$ receptor activation status (Samuelsson, Science, Vol 291, p 484-486, 2001; Kaneko, Science, Vol 313, p 670-673, 2006; Schwab, European J Immunol Vol 42, p 826-830, 2012; Sondermann, PNAS, Vol 110(24), p 9868-9872, 2013).

In diseases involving pathogenic antibodies it has been proposed that the very large dose of IVIG administered to humans (1-2 g/kg) effectively overrides the normal IgG homeostasis mechanism performed by FcRn. Effectively a large dilution of recipient IgG by donor IVIG results in enhanced catabolism and a shorter serum half-life of patient pathogenic antibodies. Other proposed mechanisms for the efficacy include anti-idiotypic neutralisation of pathogenic antibodies and transient reductions in complement factors (Mollnes, Mol Immunol, Vol 34, p 719-729, 1997; Crow, Transfusion Medicine Reviews, Vol 22(2), p 103-116, 2008; Schwab, I. and Nimmerjahn, F. Nature Reviews Immunology, Vol 13, p 176-189, 2013).

There are significant disadvantages to the clinical use of IVIG. IVIG has variable product quality between manufacturers due to inherent differences in manufacturing methods and donor pools (Siegel, Pharmacotherapy Vol 25(11) p 78S-84S, 2005). IVIG is given in very large doses, typically in the order of 1-2 g/kg. This large dose necessitates a long duration of infusion, (4-8 hours, sometimes spread over multiple days), which can be unpleasant for the patient and can result in infusion related adverse events. Serious adverse events can occur, reactions in IgA deficient individuals being well understood. Cytokine release can also be observed in patients receiving IVIG but this is largely minimised by careful control of dose and infusion rate. As a consequence of the large amounts used per patient and the reliance on human donors, manufacture of IVIG is expensive and global supplies are severely limited.

Collectively the disadvantages of IVIG mean that there is need for improvement in terms of clinical supply, administration and efficacy of molecules able to interfere with the disease biology of pathogenic antibodies and pathogenic immune complexes.

A polymeric Fc-fusion protein for use as a potential replacement for IVIG therapy has been described in the literature. (Mekhaiel et al; Nature Scientific Reports 1:124, published 19 Oct. 2011). Mekhaiel et al. describe hexameric hIgG1-Fc-LH309/310CL-tailpiece. This protein comprises a double mutation in which leucine at position 309 is substituted with cysteine, and histidine at position 310 is substituted with leucine.

It was believed at the time of the invention, that the L309C/H310L double mutation was essential for polymerisation of the monomer units. (Mekhaiel et al; 2011). However, the present inventors have surprisingly created multimeric fusion proteins which assemble efficiently into multimers in the absence of the L309C/H310L double mutation.

The absence of the cysteine residue at position 309 simplifies the isolation and purification of the multimeric fusion protein, so improving its manufacturability. It may also reduce the potential for immunogenicity. In addition, further modifications are described which greatly improve the safety and efficacy of the multimeric fusion protein of the present invention.

In the present invention we therefore provide improved multimeric fusion proteins with improved manufacturability and greater efficacy, which resolve many of the disadvantages of IVIG and prior art alternatives. The proteins may be produced in large quantities, under carefully controlled conditions, eliminating the problems of limited supply and variable quality. Furthermore, the greater efficacy allows the administration of smaller doses, reducing the risk of adverse events.

The proteins described by Mekhaiel et al were developed primarily for use as vaccines, and were typically fused to a different protein referred to as a "fusion partner" such as an antigen, pathogen-associated molecular pattern (PAMP), drug, ligand, receptor, cytokine or chemokine. In one example, the proteins of the present invention do not comprise a fusion partner.

Polymeric fusion proteins have been described in the prior art in which the carboxyl-terminal tailpiece from either IgM or IgA was added to the carboxyl-termini of whole IgG molecule constant regions to produce recombinant IgM-like IgGs. (Smith R. I. F. and Morrison, S. L. Biotechnology, Vol 12, p 683-688, 1994; Smith R. I. F. et al, J Immunol, Vol 154, p 2226-2236, 1995; Sorensen V. et al, J Immunol, Vol 156, p 2858-2865, 1996). The IgG molecules studied were intact immunoglobulins comprising variable regions. In contrast, the multimeric fusion proteins of the present invention do not comprise an antibody variable region.

In the present invention we therefore provide improved multimeric fusion proteins with improved manufacturability, and greater safety and efficacy, which resolve many of the disadvantages of IVIG and prior art alternatives. The proteins may be produced recombinantly in large quantities, under carefully controlled conditions, eliminating the problems of limited supply and variable quality. Furthermore, the greater safety and efficacy allow the administration of smaller doses, and significantly reduce the risk of adverse events.

DESCRIPTION OF THE INVENTION

The multimeric fusion proteins of the invention have been collectively named "Fc-multimers" and the two terms are used interchangeably herein Unless defined otherwise, all technical and scientific terms used herein have the same meaning as commonly understood by one of skill in the art to which this invention belongs. All publications and patents referred to herein are incorporated by reference.

It will be appreciated that any of the embodiments described herein may be combined.

In the present specification the EU numbering system is used to refer to the residues in antibody domains, unless otherwise specified. This system was originally devised by Edelman et al, 1969 and is described in detail in Kabat et al, 1987.

Edelman et al., 1969; "The covalent structure of an entire $\gamma$G immunoglobulin molecule," PNAS Biochemistry Vol. 63 pp 78-85.

Kabat et al., 1987; in Sequences of Proteins of Immunological Interest, US Department of Health and Human Services, NIH, USA.

Where a position number and/or amino acid residue is given for a particular antibody isotype, it is intended to be applicable to the corresponding position and/or amino acid residue in any other antibody isotype, as is known by a person skilled in the art. When referring to an amino acid residue in a tailpiece derived from IgM or IgA, the position number given is the position number of the residue in naturally occurring IgM or IgA, according to conventional practice in the art.

The present invention provides a multimeric fusion protein comprising two or more polypeptide monomer units;

wherein each polypeptide monomer unit comprises an antibody Fc-domain comprising two heavy chain Fc-regions;

wherein each heavy chain Fc-region comprises any amino acid residue other than cysteine at position 309, and is fused at its C-terminal to a tailpiece which causes the monomer units to assemble into a multimers and wherein each polypeptide monomer unit does not comprise an antibody variable region.

In one example, the multimeric fusion proteins of the present invention further comprise a fusion partner. The term 'fusion partner' specifically excludes one or more antibody variable domains. Typically the term 'fusion partner' refers to an antigen, pathogen-associated molecular pattern (PAMP), drug, ligand, receptor, cytokine or chemokine.

Said fusion partner, where present, is fused to the N-terminus of the or each heavy chain Fc-region. The fusion partner may be fused directly to the N-terminus of the heavy chain Fc-region. Alternatively it may be fused indirectly by means of an intervening amino acid sequence, which may include a hinge, where present. For example, a short linker sequence may be provided between the fusion partner and the heavy chain Fc-region.

In one example, the proteins of the present invention do not comprise a fusion partner.

In particular the multimeric fusion proteins of the present invention do not comprise one or more antibody variable regions, typically the molecules do not comprise either a VH or a VL antibody variable region. In one example the multimeric fusion proteins of the present invention do not comprise a Fab fragment.

Each polypeptide monomer unit of the multimeric fusion protein of the present invention comprises an antibody Fc-domain.

The antibody Fc-domain of the present invention may be derived from any suitable species. In one embodiment the antibody Fc-domain is derived from a human Fc-domain.

The antibody Fc-domain may be derived from any suitable class of antibody, including IgA (including subclasses IgA1 and IgA2), IgD, IgE, IgG (including subclasses IgG1, IgG2, IgG3 and IgG4), and IgM. In one embodiment, the antibody Fc-domain is derived from IgG1, IgG2, IgG3 or IgG4. In one embodiment the antibody Fc-domain is derived from IgG1. In one embodiment the antibody Fc domain is derived from IgG4.

The antibody Fc-domain comprises two polypeptide chains, each referred to as a heavy chain Fc-region. The two heavy chain Fc regions dimerise to create the antibody Fc-domain. Whilst the two heavy chain Fc regions within the antibody Fc domain may be different from one another it will be appreciated that these will usually be the same as one another. Hence where the term 'the heavy chain Fc-region' is used herein below this is used to refer to the single heavy chain Fc-region which dimerises with an identical heavy chain Fc-region to create the antibody Fc-domain.

Typically each heavy chain Fc-region comprises or consists of two or three heavy chain constant domains.

In native antibodies, the heavy chain Fc-region of IgA, IgD and IgG is composed of two heavy chain constant domains (CH2 and CH3) and that of IgE and IgM is composed of three heavy chain constant domains (CH2, CH3 and CH4). These dimerise to create an Fc domain.

In the present invention, the heavy chain Fc-region may comprise heavy chain constant domains from one or more different classes of antibody, for example one, two or three different classes.

In one embodiment the heavy chain Fc-region comprises CH2 and CH3 domains derived from IgG1.

In one embodiment the heavy chain Fc-region comprises CH2 and CH3 domains derived from IgG2.

In one embodiment the heavy chain Fc-region comprises CH2 and CH3 domains derived from IgG3.

In one embodiment the heavy chain Fc-region comprises CH2 and CH3 domains derived from IgG4.

The multimeric fusion proteins of the invention have been collectively named "Fc-multimers" and the two terms are used interchangeably herein The present inventors have unexpectedly found that the CH3 domain plays a significant role in controlling the polymerisation of the monomer units of the multimeric fusion proteins of the present invention. Polymerisation was unexpectedly found to vary depending on the IgG subclass from which the Fc-region was derived. Fc multimers comprising a CH2 domain and a CH3 domain derived from IgG1 assembled very efficiently into hexamers, with approximately 80% of the molecules being present in hexameric form. In contrast, Fc multimers comprising a CH2 domain and a CH3 domain derived from IgG4 formed lower levels of hexamers. Investigation of Fc multimers comprising hybrid Fc-regions in which the CH2 domain was derived from one particular IgG subclass and the CH3 domain was derived from a different IgG subclass revealed that the ability to form hexamers is encoded mainly by the CH3 domain. The presence of a CH3 domain derived from IgG1 significantly increases hexamerisation. Hybrid Fc-multimers in which the CH3 domain is derived from IgG1 and the CH2 domain is derived from IgG4 assembled just as efficiently as IgG1 wild-type, with approximately 80% of the molecules being found as hexamers. (Example 4 and FIG. 3). Thus, replacing the CH3 domain of IgG4 with that of IgG1 improves the levels of hexamerisation compared to wild type IgG4 Fc-multimers. The resulting hybrid has the advantage of high levels of hexamer formation whilst retaining many of the desirable properties of IgG4.

In addition, the CH3 domain of IgG1 is known to confer thermal stability. (Garber and Demarest, Biochem and Biophys Res Comm, Vol 355 p 751-757 2007). Thus, hybrid Fc-multimers comprising a CH3 domain derived from IgG1 will also have improved stability.

Thus in one embodiment the heavy chain Fc region comprises a CH3 domain derived from IgG1.

In one embodiment the heavy chain Fc region comprises a CH2 domain derived from IgG4 and a CH3 domain derived from IgG1.

Accordingly, in one embodiment the present invention provides a multimeric fusion protein comprising two or more polypeptide monomer units;

wherein each polypeptide monomer unit comprises an antibody Fc-domain comprising two heavy chain Fc-regions;

wherein each heavy chain Fc-region comprises any amino acid residue other than cysteine at position 309, and is fused at its C-terminal to a tailpiece which causes the monomer units to assemble into a multimer; and wherein each heavy chain Fc-region comprises a CH2 domain derived from IgG4 and a CH3 domain derived from IgG1 and optionally the polypeptide monomer unit does not comprise an antibody variable region.

The inventors have demonstrated that the amino acid at position 355 of the CH3 domain is critical for hexamerisation. The arginine residue normally found at position 355 of the IgG1 CH3 domain was found to promote particularly efficient hexamerisation. See Example 4 described herein below Thus in one embodiment, the heavy chain Fc region comprises an arginine residue at position 355.

Substitution of the arginine residue normally found at position 355 of the IgG1 CH3 domain with a cysteine residue (R355C) increased hexamer formation beyond that of wild type IgG1. See Example 4 described herein below.

Thus in one embodiment, the heavy chain Fc region comprises a cysteine residue at position 355.

In the Fc-multimers of the present invention which comprise a CH3 domain derived from IgG4, substitution of the glutamine residue at position 355 with an arginine residue (Q355R) significantly increases hexamerisation. Thus, the problem of lower hexamerisation of IgG4 Fc-multimers can be solved by a single amino acid substitution. This has the advantage that the resulting Fc-multimer assembles into hexamers with high efficiency whilst retaining the characteristic properties of IgG4.

Thus in one embodiment, the heavy chain Fc region comprises a CH3 domain derived from IgG4 in which the glutamine residue at position 355 has been substituted with another amino acid.

Thus in one embodiment, the heavy chain Fc region comprises a CH3 domain derived from IgG4 in which the glutamine residue at position 355 has been substituted with an arginine residue (Q355R) or a cysteine residue (Q355C).

In one embodiment the heavy chain Fc-region comprises a CH4 domain from IgM. The IgM CH4 domain is typically located between the CH3 domain and the tailpiece.

In one embodiment the heavy chain Fc-region comprises CH2 and CH3 domains derived from IgG and a CH4 domain derived from IgM.

It will be appreciated that the heavy chain constant domains for use in producing a heavy chain Fc-region of the present invention may include variants of the naturally occurring constant domains described above. Such variants may comprise one or more amino acid variations compared to wild type constant domains. In one example the heavy chain Fc-region of the present invention comprises at least one constant domain which varies in sequence from the wild type constant domain. It will be appreciated that the variant constant domains may be longer or shorter than the wild type constant domain. Preferably the variant constant domains are at least 50% identical or similar to a wild type constant domain. The term "identity", as used herein, indicates that at any particular position in the aligned sequences, the amino acid residue is identical between the sequences. The term "similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

- phenylalanine, tyrosine and tryptophan (amino acids having aromatic side chains);
- lysine, arginine and histidine (amino acids having basic side chains);
- aspartate and glutamate (amino acids having acidic side chains);
- asparagine and glutamine (amino acids having amide side chains); and
- cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In one example the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

Each heavy chain Fc-region is fused at its C-terminus to a tailpiece which causes the polypeptide monomer units to assemble into a multimer.

IgM and IgA occur naturally in humans as covalent multimers of the common $H_2L_2$ antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. This tailpiece includes a cysteine residue that forms a disulphide bond between heavy chains in the polymer, and is believed to have an important role in polymerisation. The tailpiece also contains a glycosylation site.

The tailpiece of the present invention may comprise any suitable amino acid sequence. It may be a tailpiece found in a naturally occurring antibody, or alternatively, it may be a modified tailpiece which differs in length and/or composition from a natural tailpiece. Other modified tailpieces may be entirely synthetic and may be designed to possess desired properties for multimerisation, such as length, flexibility and cysteine composition.

The tailpiece may be derived from any suitable species. Antibody tailpieces are evolutionarily conserved and are found in most species, including primitive species such as teleosts. In one embodiment the tailpiece of the present invention is derived from a human antibody.

In one embodiment, the tailpiece comprises all or part of an 18 amino acid tailpiece sequence from human IgM or IgA as shown in Table 1.

The tailpiece may be fused directly to the C-terminus of the heavy chain Fc-region. Alternatively, it may be fused indirectly by means of an intervening amino acid sequence. For example, a short linker sequence may be provided between the tailpiece and the heavy chain Fc-region.

The tailpiece of the present invention may include variants or fragments of the native sequences described above. A variant of an IgM or IgA tailpiece typically has an amino acid sequence which is identical to the native sequence in 8, 9, 10, 11, 12, 13, 14, 15, 16, or 17 of the 18 amino acid positions shown in Table 1. A fragment typically comprises 8, 9, 10, 11, 12, 13, 14, 15, 16, or 17 amino acids. The tailpiece may be a hybrid IgM/IgA tailpiece. Fragments of variants are also envisaged.

TABLE 1

Tailpiece sequences

| Tailpiece | Sequence |
|---|---|
| IgM | PTLYNVSLVMSDTAGTCY SEQ ID NO: 1 |
| IgA | PTHVNVSVVMAEVDGTCY SEQ ID NO: 2 |

Each heavy chain Fc-region of the present invention may optionally possess a native or a modified hinge region at its N-terminus.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the heavy chain Fc-region. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO9915549, WO2005003170, WO2005003169, WO2005003170, WO9825971 and WO2005003171 and these are incorporated herein by reference.

Examples of suitable hinge sequences are shown in Table 2.

In one embodiment, the heavy chain Fc-region possesses an intact hinge region at its N-terminus.

In one embodiment the heavy chain Fc-region and hinge region are derived from IgG4 and the hinge region comprises the mutated sequence CPPC (SEQ ID NO: 11). The core hinge region of human IgG4 contains the sequence CPSC (SEQ ID NO: 12) compared to IgG1 which contains the sequence CPPC. The serine residue present in the IgG4 sequence leads to increased flexibility in this region, and therefore a proportion of molecules form disulphide bonds within the same protein chain (an intrachain disulphide) rather than bridging to the other heavy chain in the IgG molecule to form the interchain disulphide. (Angel S. et al, Mol Immunol, Vol 30(1), p 105-108, 1993). Changing the serine residue to a proline to give the same core sequence as IgG1 allows complete formation of inter-chain disulphides in the IgG4 hinge region, thus reducing heterogeneity in the purified product. This altered isotype is termed IgG4P.

TABLE 2

Hinge sequences

| Hinge | Sequence |
|---|---|
| Human IgA1 | VPSTPPTPSPSTPPTPSPS SEQ ID NO: 3 |
| Human IgA2 | VPPPPP SEQ ID NO: 4 |
| Human IgD | ESPKAQASSVPTAQPQAEGSLAKATTAPATTR NTGRGGEEKKKEKEKEEQEERETKTP SEQ ID NO: 5 |
| Human IgG1 | EPKSCDKTHTCPPCP SEQ ID NO: 6 |
| Human IgG2 | ERKCCVECPPCP SEQ ID NO: 7 |
| Human IgG3 | ELKTPLGDTTHTCPRCPEPKSCDTPPPCPRCP EPKSCDTPPPCPRCPEPKSCDTPPPCPRCP SEQ ID NO: 8 |
| Human IgG4 | ESKYGPPCPSCP SEQ ID NO: 9 |
| Human IgG4(P) | ESKYGPPCPPCP SEQ ID NO: 10 |
| Recombinant v1 | CPPC SEQ ID NO: 11 |
| Recombinant v2 | CPSC SEQ ID NO: 12 |
| Recombinant v3 | CPRC SEQ ID NO: 13 |
| Recombinant v4 | SPPC SEQ ID NO: 14 |
| Recombinant v5 | CPPS SEQ ID NO: 15 |
| Recombinant v6 | SPPS SEQ ID NO: 16 |
| Recombinant v7 | DKTHTCAA SEQ ID NO: 17 |
| Recombinant v8 | DKTHTCPPCPA SEQ ID NO: 18 |
| Recombinant v9 | DKTHTCPPCPATCPPCPA SEQ ID NO: 19 |
| Recombinant v10 | DKTHTCPPCPATCPPCPATCPPCPA SEQ ID NO: 20 |
| Recombinant v11 | DKTHTCPPCPAGKPTLYNSLVMSDTAGTCY SEQ ID NO: 21 |
| Recombinant v12 | DKTHTCPPCPAGKPTHVNVSVVMAEVDGTCY SEQ ID NO: 22 |
| Recombinant v13 | DKTHTCCVECPPCPA SEQ ID NO: 23 |
| Recombinant v14 | DKTHTCPRCPEPKSCDTPPPCPRCPA SEQ ID NO: 24 |
| Recombinant v15 | DKTHTCPSCPA SEQ ID NO: 25 |

The multimeric fusion protein of the invention may comprise two, three, four, five, six, seven, eight, nine, ten, eleven or twelve or more polypeptide monomer units. Such proteins may alternatively be referred to as a dimer, trimer, tetramer, pentamer, hexamer, heptamer, octamer, nonamer, decamer, undecamer, dodecamer, etc., respectively.

The multimeric fusion protein may comprise a mixture of multimeric fusion proteins of different sizes, having a range of numbers of polypeptide monomer units.

In one embodiment, the multimeric fusion protein of the invention comprises six or twelve polypeptide monomer units.

In one example, the multimeric fusion protein of the present invention is a hexamer.

Accordingly in one example the present invention provides a multimeric fusion protein consisting of six polypeptide monomer units;

wherein each polypeptide monomer unit consists of an antibody Fc-domain and a tailpiece region;

wherein each antibody Fc domain consists of two heavy chain Fc-regions in which the amino acid residue at position 309 is any amino acid residue other than cysteine; and, optionally, each heavy chain Fc region possesses a hinge region at the N-terminus; and wherein the tailpiece region is fused to the C-terminus of each heavy chain Fc region and causes the monomer units to assemble into a multimer.

In one example the multimeric fusion protein of the present invention is a purified hexamer. In one example the term 'purified' means greater than 80% hexamer, for example greater than 90% or 95% hexamer.

It will be appreciated that the quantity of hexamer in a sample can be determined using any suitable method such as analytical size exclusion chromatography as described herein below.

In one example the present invention provides a mixture comprising a multimeric fusion protein of the invention in more than one multimeric form, for example hexamer and docdecamer, but in which the mixture is enriched for the hexameric form of said multimeric fusion protein.

In one example such a mixture may comprise greater than 80% hexamer. In one example such a mixture may comprise greater than 85%, 90%, or 95%.

Each polypeptide monomer unit of the invention comprises two individual polypeptide chains. The two polypeptide chains within a particular polypeptide monomer unit may be the same as one another, or they may be different from one another. In one embodiment, the two polypeptide chains are the same as one another.

Similarly, the polypeptide monomer units within a particular multimeric fusion protein may be the same as one another, or they may be different from one another. In one embodiment, the polypeptide monomer units are the same as one another.

In one embodiment, a polypeptide chain of a polypeptide monomer unit comprises an amino acid sequence as provided in FIG. 2, optionally with an alternative hinge or tailpiece sequence.

Accordingly in one example the present invention also provides a multimeric fusion protein comprising or consisting of two or more, preferably six, polypeptide monomer units;

wherein each polypeptide monomer unit comprises two identical polypeptide chains each polypeptide chain comprising or consisting of the sequence given in any one of SEQ ID Nos 26 to 47 and wherein each polypeptide monomer unit does not comprise an antibody variable region.

In one example the present invention also provides a multimeric fusion protein comprising or consisting of two or more, preferably six, polypeptide monomer units; wherein each polypeptide monomer unit comprises two identical polypeptide chains each polypeptide chain comprising or consisting of a sequence selected from the group consisting of SEQ ID No: 26, SEQ ID No: 27, SEQ ID No: 28, SEQ ID No: 29, SEQ ID No: 30, SEQ ID No: 31, SEQ ID No: 32, SEQ ID No: 33, SEQ ID No: 34, SEQ ID No: 35, SEQ ID No: 36, SEQ ID No: 37, SEQ ID No: 38, SEQ ID No: 39, SEQ ID No: 40, SEQ ID No: 41, SEQ ID No: 42, SEQ ID No: 43, SEQ ID No: 44, SEQ ID No: 45, SEQ ID No: 46 and SEQ ID No: 47; and wherein optionally each polypeptide monomer unit does not comprise an antibody variable region.

In one example where the hinge and tailpiece may be varied from the sequences given in SEQ ID NOs 26 to 47 the present invention provides a multimeric fusion protein comprising two or more polypeptide monomer units;

wherein each polypeptide monomer unit comprises an antibody Fc-domain comprising two heavy chain Fc-regions;

wherein each heavy chain Fc-region comprises or consists of the sequence given in amino acids 6 to 222 of any one of SEQ ID NOs 26 to 29 or amino acids 6 to 222 of any one of SEQ ID NOs 32 to 47 or the sequence given in amino acids 6 to 333 of SEQ ID NOs 30 or 31 and which is fused at its C-terminal to a tailpiece which causes the monomer units to assemble into a multimer and wherein the polypeptide monomer unit does not comprise an antibody variable region.

Typically in addition to the tailpiece at the C-terminus, each heavy chain Fc-region further comprises a hinge sequence at the N-terminus.

The multimeric fusion proteins of the present invention may comprise one or more mutations that alter the functional properties of the proteins, for example, binding to Fc-receptors such as FcRn or leukocyte receptors, binding to complement, modified disulphide bond architecture or altered glycosylation patterns, as described herein below. It will be appreciated that any of these mutations may be combined in any suitable manner to achieve the desired functional properties, and/or combined with other mutations to alter the functional properties of the proteins.

In the present invention, Fc-multimers have been created that are particularly suitable for use in the treatment of immune disorders. The Fc-multimers have been engineered to possess the following properties:

The potency of an Fc-multimer protein for use in the treatment of immune disorders should be as high as possible. Potency may be determined by measuring the inhibition of macrophage phagocytosis of antibody coated target cells as described in Example 6.

Unwanted side effects should be as low as possible. Unwanted side effects may be determined by measuring cytokine release, C1q binding and platelet activation as described in Examples 8, 15 and 16 respectively.

Wild type IgG1 Fc-multimer comprising a CH2 and CH3 domain derived from IgG1 without any additional mutations may be less suitable for use in the treatment of immune disorders because, although it displays high potency of phagocytosis inhibition, it also shows high levels of unwanted side effects, measured by cytokine release, C1q binding and platelet activation.

Figure 7:
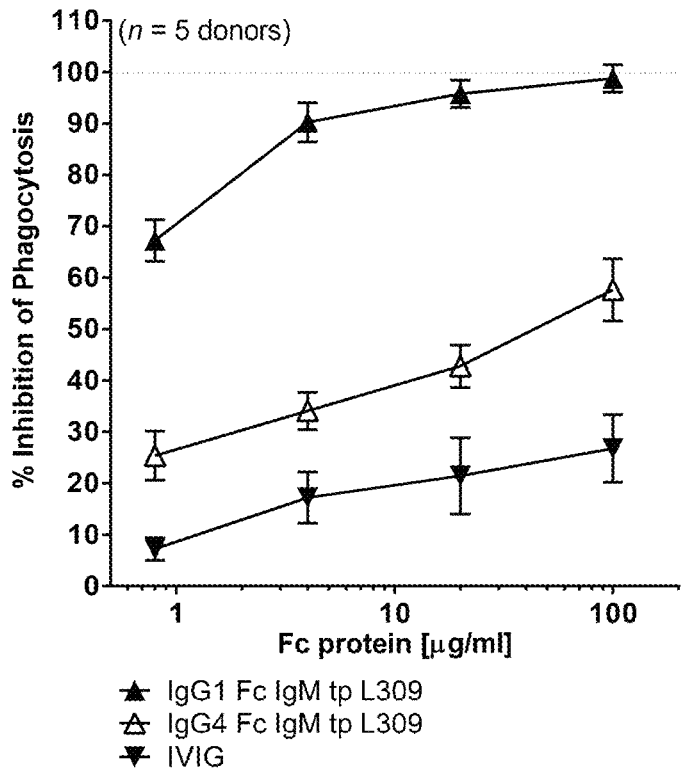
Figure 7:
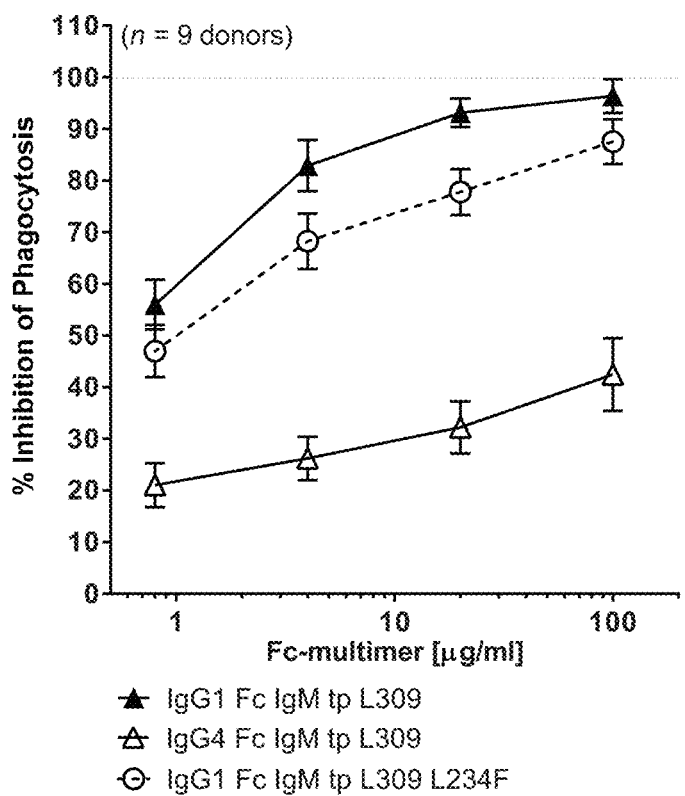
Figure 7:
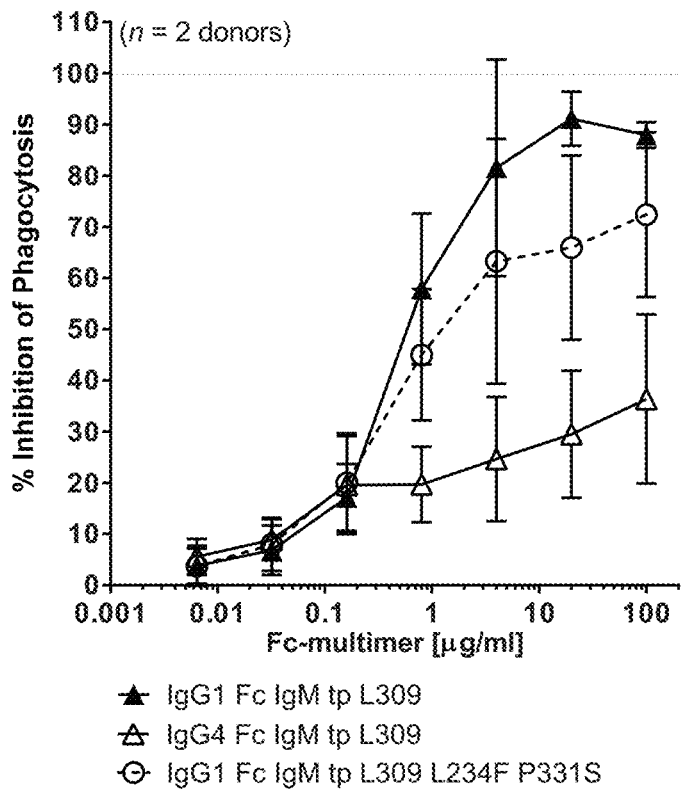
Figure 7:
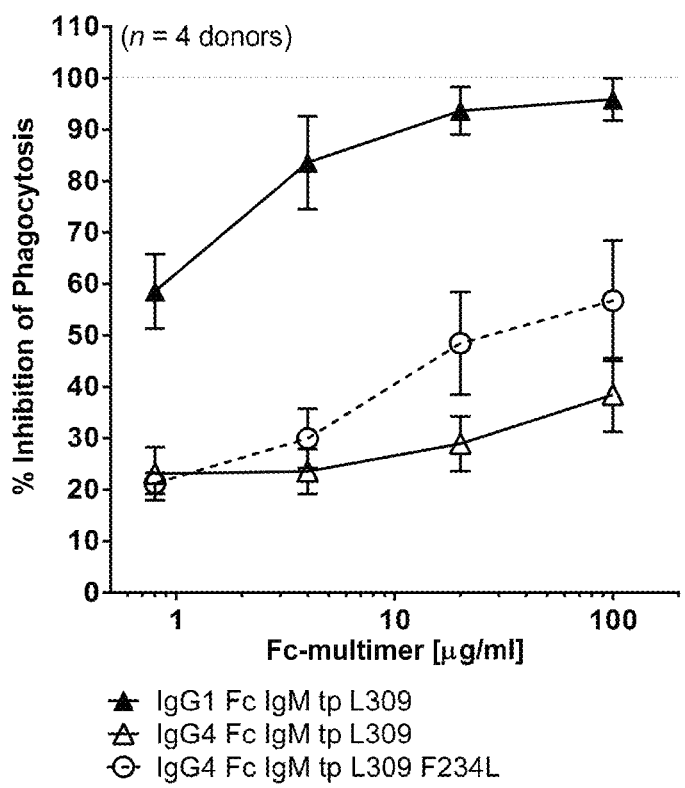
Figure 7:
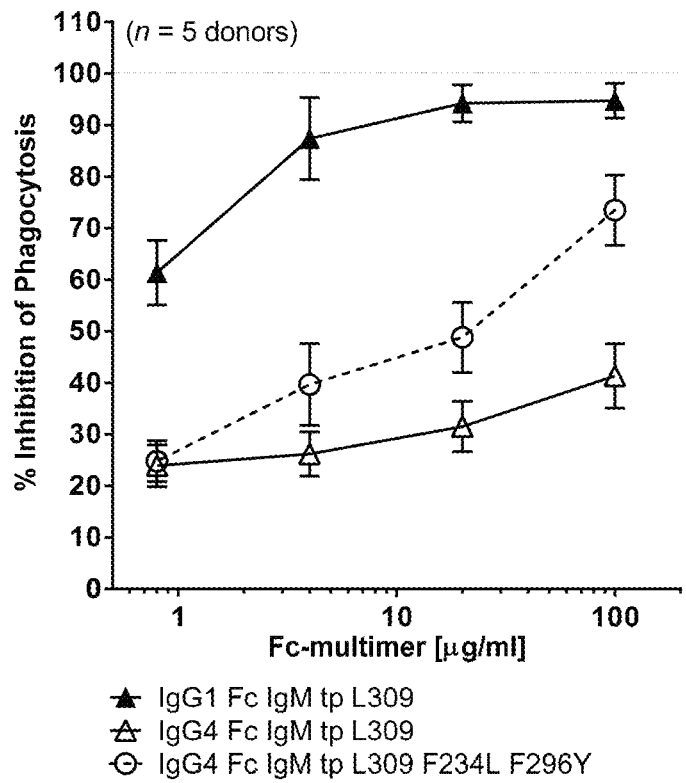
Figure 7:
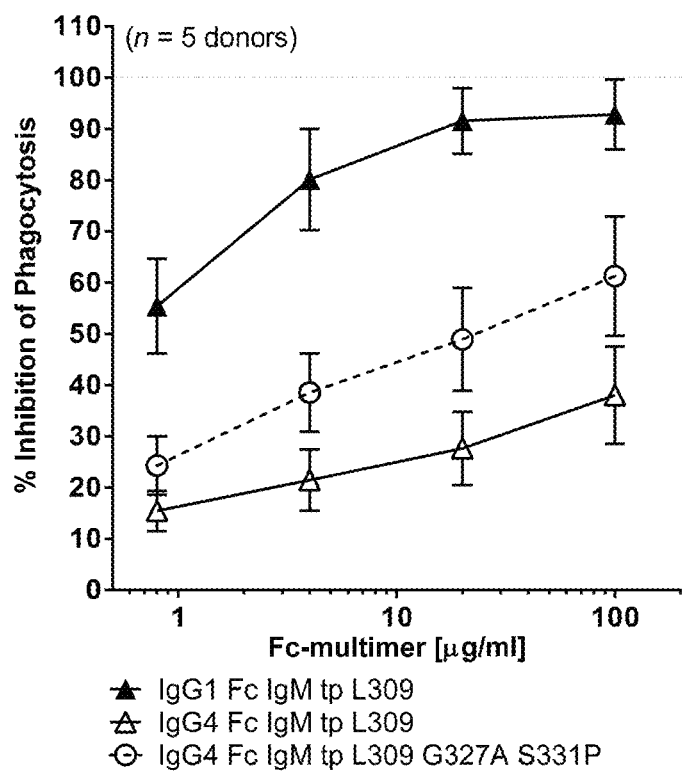
Figure 7:
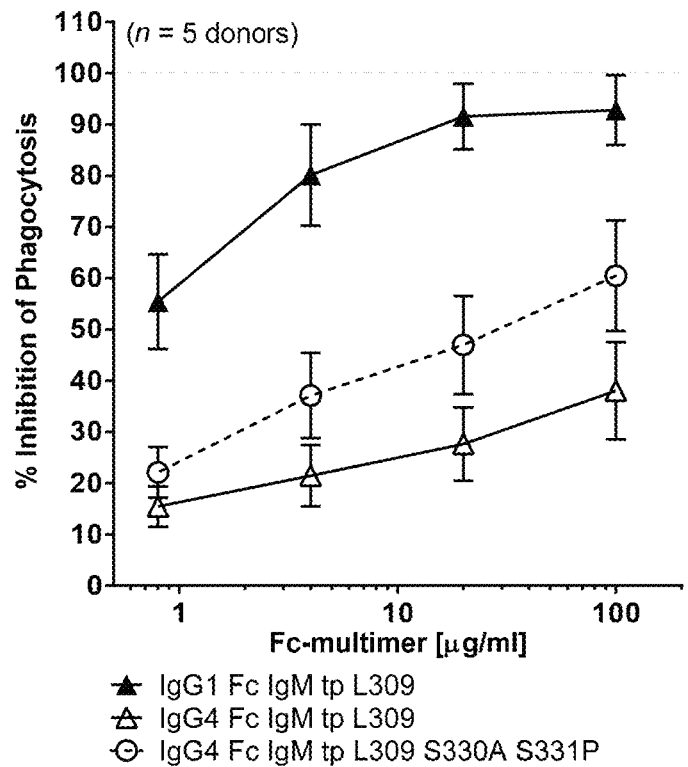
Figure 7:
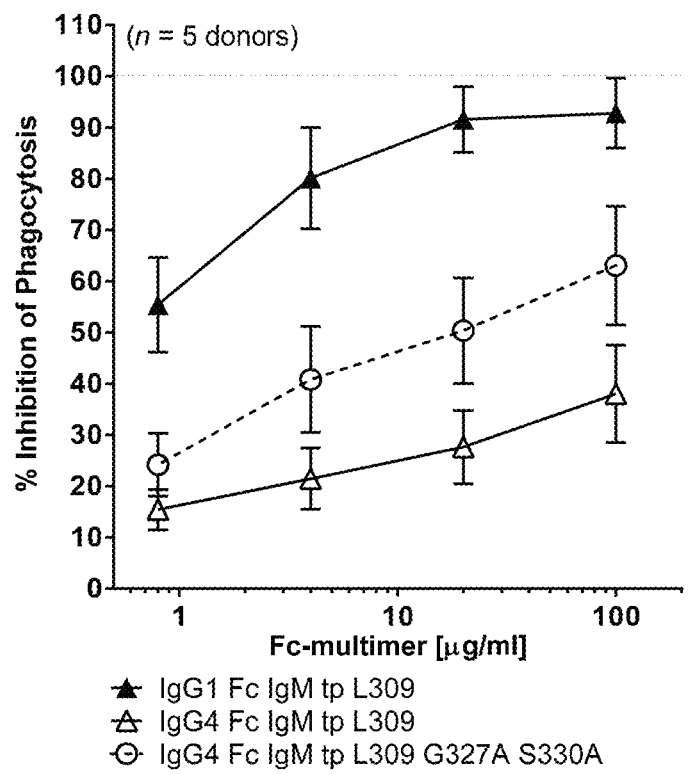
Figure 7:
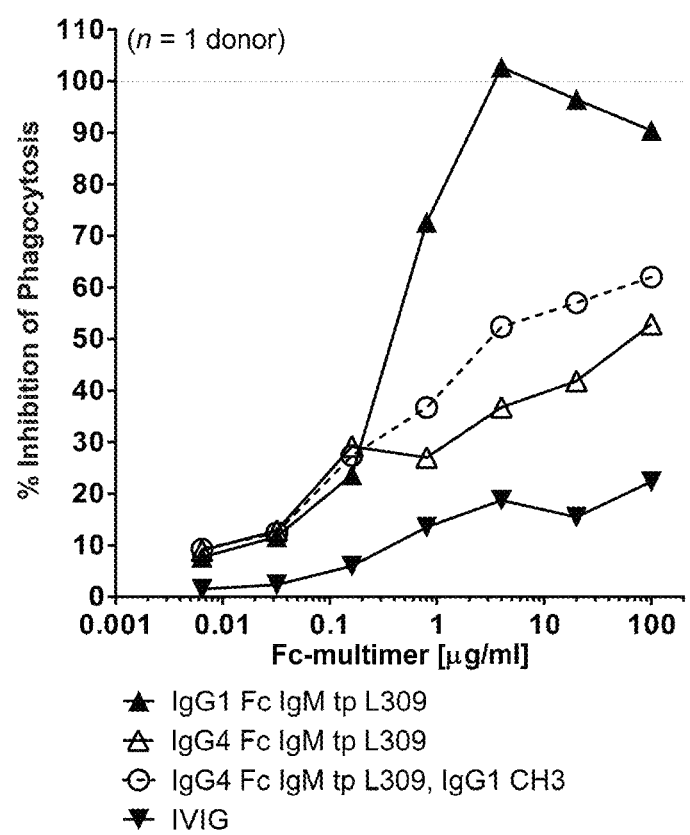

Wild type IgG4 Fc-multimer comprising a CH2 and CH3 domain derived from IgG4, produces very low levels of unwanted side effects although its potency is low relative to that of IgG1. Notwithstanding, the potency of wild type IgG4 Fc-multimer is still significantly higher than that of IVIG, as shown in FIG. 7.

In one example the present invention also provides Fc-multimer proteins that have been engineered to combine the desirable properties of both IgG1 and IgG4 wild type Fc-multimers, without the undesirable properties. These Fc-multimers display effective levels of potency, whilst reducing unwanted side effects to a tolerable level as shown below in Table 3. These Fc-multimers are expected to be particularly useful for use in the treatment of immune disorders.

TABLE 3

| Fc-multimer | phagocytosis inhibition | IFNγ release | C1q binding | platelet activation |
|---|---|---|---|---|
| wild type IgG1 Fc-multimer | the standard for "IgG1-like" | the standard for "IgG1-like" | the standard for "IgG1-like" | the standard for "IgG1-like" |
| wild type IgG4 Fc-multimer | the standard for "IgG4-like" | the standard for "IgG4-like" | the standard for "IgG4-like" | the standard for "IgG4-like" |
| IgG1 Fc IgM tp L309 L234F P331S | high | medium | IgG4-like | IgG4-like |
| Hybrid Fc IgG4-CH2 IgG1-CH3 IgM tp L309 | medium | IgG4-like | IgG4-like | low |
| IgG4 Fc IgM tp L309 F234L | medium | IgG4-like | IgG4-like | medium |
| IgG4 Fc IgM tp L309 F234L F296Y | medium | IgG4-like | IgG4-like | medium |
| IgG4 Fc IgM tp L309 G327A S330A | medium | IgG4-like | IgG4-like | IgG4-like |
| IgG4 Fc IgM tp L309 G327A S331P | medium | IgG4-like | medium | IgG4-like |
| IgG4 Fc IgM tp L309 S330A S331P | medium | IgG4-like | medium | IgG4-like |

In one example the present invention provides multimeric fusion proteins comprising one or more mutations which decrease cytokine release and/or decrease platelet activation and/or decrease C1q binding when compared to the unmodified parent multimeric fusion protein. In one example the unmodified parent is a multimeric fusion protein of the present invention containing CH2 and CH3 domains derived from IgG1.

Cytokine release, platelet activation and C1q binding may be measured by any suitable method known in the art. In one example cytokine release is measured in a whole blood cytokine release assay.

In one example platelet activation is measured by flow cytometry using CD62p as an activation marker.

In one example C1q binding is measured by ELISA.

In one example the present invention provides multimeric fusion proteins comprising one or more mutations which increase the potency of inhibition of macrophage phagocytosis of antibody-coated target cells when compared to the unmodified parent multimeric fusion protein. In one example the unmodified parent is a multimeric fusion protein of the present invention containing a CH2 and CH3 domain derived from IgG4 or a CH2 domain from IgG4 and a CH3 domain from IgG1.

Suitable assays for measuring inhibition of macrophage phagocytosis of antibody coated target cells are known in the art and are described in the examples herein.

Accordingly in one example each heavy chain Fc-region of a multimeric fusion protein of the present invention comprises CH2 and CH3 domains derived from IgG1 in which the leucine residue at position 234 and/or the proline residue at position 331 and/or the alanine at position 327 and/or the tyrosine at position 296 has been substituted with another amino acid.

In one embodiment the heavy chain Fc-region comprises CH2 and CH3 domains derived from IgG1 in which the leucine residue at position 234 has been substituted with a phenylalanine residue and the proline residue at position 331 has been substituted with a serine residue (L234F/P331S).

In one embodiment the heavy chain Fc-region is a hybrid comprising a CH2 domain derived from IgG4 and a CH3 domain derived from IgG1.

In one example each heavy chain Fc-region of a multimeric fusion protein of the present invention comprises a CH2 domain from IgG4 and a CH3 domain derived from IgG4 or IgG1 in which one or more amino acid residues selected from the group consisting of the phenylalanine residue at position 234, the phenylalanine residue at position 296, the glycine residue at position 327, the serine residue at position 330 and the serine residue at position 331, have been substituted with another amino acid.

In one example each heavy chain Fc-region of a multimeric fusion protein of the present invention comprises a CH2 domain from IgG4 and a CH3 domain derived from IgG4 or IgG1 in which one or more amino acid residues or pairs of amino acids selected from the group consisting of F234, F234 and F296, G327, G327 and S331, S330 and S331, and, G327 and S330 have been substituted with another amino acid.

In one embodiment the heavy chain Fc-region comprises CH2 and CH3 domains derived from IgG4 in which the phenylalanine residue at position 234 has been substituted with a leucine residue (F234L).

In one embodiment the heavy chain Fc-region comprises CH2 and CH3 domains derived from IgG4 in which the phenylalanine residue at position 234 has been substituted with a leucine residue and the phenylalanine residue at position 296 has been substituted with a tyrosine residue (F234L/F296Y).

In one embodiment the heavy chain Fc-region comprises CH2 and CH3 domains derived from IgG4 in which the glycine residue at position 327 has been substituted with an alanine residue and the serine residue at position 330 has been substituted with an alanine residue (G327A/S330A).

In one embodiment the heavy chain Fc-region comprises CH2 and CH3 domains derived from IgG4 in which the glycine residue at position 327 has been substituted with an alanine residue and the serine residue at position 331 has been substituted with a proline residue (G327A/S331P).

In one embodiment the heavy chain Fc-region comprises CH2 and CH3 domains derived from IgG4 in which the serine residue at position 330 has been substituted with an alanine residue and the serine residue at position 331 has been substituted with a proline residue (S330A/S331P).

In one embodiment the heavy chain Fc-region is a hybrid comprising a CH2 domain derived from IgG4 and a CH3 domain derived from IgG1, in which the phenylalanine residue at position 234 has been substituted with a leucine residue (F234L).

In one embodiment the heavy chain Fc-region is a hybrid comprising a CH2 domain derived from IgG4 and a CH3 domain derived from IgG1, in which the phenylalanine residue at position 234 has been substituted with a leucine residue and the phenylalanine residue at position 296 has been substituted with a tyrosine residue (F234L/F296Y).

In one embodiment the heavy chain Fc-region is a hybrid comprising a CH2 domain derived from IgG4 and a CH3 domain derived from IgG1, in which the glycine residue at position 327 has been substituted with an alanine residue and the serine residue at position 330 has been substituted with an alanine residue (G327A/S330A).

In one embodiment the heavy chain Fc-region is a hybrid comprising a CH2 domain derived from IgG4 and a CH3 domain derived from IgG1, in which the glycine residue at position 327 has been substituted with an alanine residue and the serine residue at position 331 has been substituted with a proline residue (G327A/S331P).

In one embodiment the heavy chain Fc-region is a hybrid comprising a CH2 domain derived from IgG4 and a CH3 domain derived from IgG1, in which the serine residue at position 330 has been substituted with an alanine residue and the serine residue at position 331 has been substituted with a proline residue (S330A/S331P).

The multimeric fusion protein of the invention may show altered binding to one or more Fc-receptors (FcR's) in comparison with the corresponding polypeptide monomer unit and/or native immunoglobulin. The binding to any particular Fc-receptor may be increased or decreased. In one embodiment, the multimeric fusion protein of the invention comprises one or more mutations which alter its Fc-receptor binding profile.

The term "mutation" as used herein may include substitution, addition or deletion of one or more amino acids.

Human cells can express a number of membrane bound FcR's selected from FcαR, FcεR, FcγR, FcRn and glycan receptors. Some cells are also capable of expressing soluble (ectodomain) FCR (Fridman et al., (1993) J Leukocyte Biology 54: 504-512 for review). FcγR can be further divided by affinity of IgG binding (high/low) and biological effect (activating/inhibiting). Human FcγRI is widely considered to be the sole 'high affinity' receptor whilst all of the others are considered as medium to low. FcγRIIb is the sole receptor with 'inhibitory' functionality by virtue of its intracellular ITIM motif whilst all of the others are considered as 'activating' by virtue of ITAM motifs or pairing with the common FcγR-γchain. FcγRIIIb is also unique in that although activatory it associates with the cell via a GPI anchor. In total, humans express six 'standard' FcγR: FcγRI, FcγRIIa, FcγRIIb, FcγRIIc, FcγRIIIa FcγRIIIb. In addition to these sequences there are a large number of sequence or allotypic variants spread across these families. Some of these have been found to have important functional consequence and so are sometimes considered to be receptor sub-types of their own. Examples include FcγRIIa$^{H134R}$, FcγRIIb$^{I190T}$, FcγRIIIa$^{F158V}$ and FcγRIIIb$^{NA1}$, FcγRIIIb$^{NA2}$ FcγRIIIb$^{SH}$. Each receptor sequence has been shown to have different affinities for the 4 sub-classes of IgG: IgG1, IgG2, IgG3 and IgG4 (Bruhns Blood (1993) Vol 113, p 3716-3725). Other species have somewhat different numbers and functionality of FcγR, with the mouse system being the best studied to date and comprising of 4 FcγR; FcγRI FcγRIIb FcγRIII FcγRIV (Bruhns, Blood (2012) Vol 119, p 5640-5649). Human FcγRI on cells is normally considered to be 'occupied' by monomeric IgG in normal serum conditions due to its affinity for IgG1/IgG3/IgG4 ($\sim 10^{-8}$M) and the concentration of these IgG in serum ($\sim$10 mg/ml). Hence cells bearing FcγRI on their surface are considered to be capable for 'screening' or 'sampling' of their antigenic environment vicariously through the bound polyspecific IgG. The other receptors having lower affinities for IgG sub-classes (in the range of ($\sim 10^{-8}$-$10^{-7}$M) are normally considered to be 'unoccupied'. The low affinity receptors are hence inherently sensitive to the detection of and activation by antibody involved immune complexes. The increased Fc density in an antibody immune complex results in increased functional affinity of binding 'avidity' to low affinity FcγR. This has been demonstrated in vitro using a number of methods (Shields R. L. et al, J Biol Chem, Vol 276(9), p 6591-6604, 2001; Lux et al., J Immunol (2013) Vol 190, p 4315-4323). It has also been implicated as being one of the primary modes of action in the use of anti-RhD to treat ITP in humans (Crow Transfusion Medicine Reviews (2008) Vol 22, p 103-116).

Many cell types express multiple types of FcγR and so binding of IgG or antibody immune complex to cells bearing FcγR can have multiple and complex outcomes depending upon the biological context. Most simply, cells can either receive an activatory, inhibitory or mixed signal. This can result in events such as phagocytosis (e.g. macrophages and neutrophils), antigen processing (e.g. dendritic cells), reduced IgG production (e.g. B-cells) or degranulation (e.g. neutrophils, mast cells). There are data to support that the inhibitory signal from FcγRIIb can dominate that of activatory signals (Proulx Clinical Immunology (2010) 135:422-429.

Cytokines are a family of highly potent proteins which modulate cells of the immune system or effect the killing of target cells such as virally infected or pre-cancerous host cells. The high level of potency has been investigated for use as therapeutic proteins on their own or after fusion to targeting moieties. IL-2, TNFα, G-CSF, GM-CSF, IFNα, IFNβ, IFNγ have all been investigated for use in humans. Their extreme potency was evidenced by a broad range of side effects or adverse events which resulted in rather restricted uses in patients with serious or life threatening conditions.

Production of cytokines in vivo can be elicited after the systemic administration of therapeutic proteins such as antibodies or immunoglobulins. Cytokine production can be short lived and temporary such as during and immediately after administration by infusion or subcutaneous injection. For example, infusion of intravenous immunoglobulin is known to result in the production of TNFα, IL-6, IL-8 and IFNγ (Aukrust P et al, Blood, Vol 84, p 2136-2143, 1994) which are associated with common infusion related events: fever, chills and nausea. Cytokine production may be longer lived and related to drug mode of action due to activation of effector cells, for example as in so called 'tumour lysis syndrome'. Extreme examples have been life threatening when administration of a drug causes tytokine storm' (Suntharalingam G et al, N Engl J Med, Vol 355, p 1018-1028, 2006).

There is a clear need to understand and minimise the cytokine release risk of engineered recombinant proteins. Recombinant proteins that contain the Fc domain of antibodies, and that are capable of becoming functionally multivalent, require special attention.

In the present study of multimeric Fc domains a whole blood cytokine release assay was deployed to study the effects of mutagenesis with the aim of minimising cytokine release. (Example 7).

Platelets (thrombocytes) are small anucleated cells which are very abundant in blood. Platelets are involved, along with clotting factors and others cells in the cessation of bleeding by formation of blood clots. Platelets are involved in a number of maladies. Low platelet count "thrombocytopenia" can be caused by a number of factors and results in increased bruising and bleeding. Inadvertent clotting "thrombosis" includes events such as stroke and deep vein thrombosis. Human and non-human primate platelets, but not mice platelets; express FcγRIIa on their surface. Platelets can respond very quickly to vessel damage by means of pre-formed 'dense-granules' and 'alpha granules' and release of potent immunokines and other molecules such as histamine, serotonin, thromboxane, PAF, PDGF, TGFγ IL1β and many others (Semple Nature Reviews Immunology 2011 11: 265-274).

Platelets have been mechanistically involved in the toxicology of drugs administered to humans. Certain antibodies have been found to be of special interest because both their target antigen and the Fc-domain have been capable of interacting with the platelet, activating them and causing thrombosis (Horsewood 1991 78(4):1019-1026). Direct, dual binding mechanisms have been proposed for anti-CD40 Mabs (Langer Thrombosis and Haemostasis 2005 93:1127-1146). Alternatively, thrombosis can be caused indirectly by antibodies cross-linking with a target molecule which can interact with platelets such as in 'HIT syndrome' (heparin induced thrombocytopenia). Unfractionated heparin was associated with venous thrombosis in approximately 12% or recipients (Levine Chest 2006 130: 681-687). In other examples such as Mabs targeting VEGF, the mechanism of action is likely to involve heparin acting as bridge between VEGF, antibody and platelet (Scappaticci 2007 J National Cancer Institute 99:1232-1239; Meyer J. Thrombosis and Haemostasis 2009 7:171-181). Thrombosis can also be caused by aggregated IgG and hence product quality is of importance when manufacturing IgG and perhaps of special importance when manufacturing multimeric Fc-domains (Ginsberg J. Experimental Medicine 1978 147:207-218).

Platelet activation is a pre-cursor to, but not necessarily a commitment towards thrombosis. Platelet activation can be followed in vitro by means of serotonin release assays or following activation markers such as CD62p, CD63 or PAC-1. Platelet aggregation can be observed directly in vitro by means of whole blood, platelet rich plasma or washed platelet aggregation assays. Mice transgenic for human FcγRIIa expression on platelets can also be used to study thrombosis or reduced clotting in vivo. The construction of multimeric Fc-domain proteins poses a foreseeable risk with regards to thrombosis, hence in the present invention Fc-engineering and platelet activation assays have been deployed to understand and ensure the safety of the Fc-multimers. FcRn, has a crucial role in maintaining the long half-life of IgG in the serum of adults and children. The receptor binds IgG in acidified vesicles (pH<6.5) protecting the IgG molecule from degradation, and then releasing it at the higher pH of 7.4 in blood.

FcRn is unlike leukocyte Fc receptors, and instead, has structural similarity to MHC class I molecules. It is a heterodimer composed of a $β_2$-microglobulin chain, non-covalently attached to a membrane-bound chain that includes three extracellular domains. One of these domains, including a carbohydrate chain, together with $β_2$-microglobulin interacts with a site between the CH2 and CH3 domains of Fc. The interaction includes salt bridges made to histidine residues on IgG that are positively charged at pH<6.5. At higher pH, the His residues lose their positive charges, the FcRn-IgG interaction is weakened and IgG dissociates.

A polymeric Fc-fusion protein for use as a potential replacement for IVIG therapy has been described in the literature but this protein does not bind to human FcRn. It therefore has a reduced functionality in vivo. (Mekhaiel et al; Nature Scientific Reports 1:124, published 19 Oct. 2011).

Mekhaiel et al. describe a polymeric human Fc-fusion protein, hexameric hIgG1-Fc-LH309/3100L-tailpiece. This protein comprises a double mutation in which leucine at position 309 is substituted with cysteine, and histidine at position 310 is substituted with leucine. Because H310 is critical for binding to human FcRn, the protein described by Mekhaiel is not capable of binding to human FcRn.

It was believed at the time of the invention, that the L309C/H310L double mutation was essential for polymerisation of the monomer units. (Mekhaiel et al; 2011). However, the present inventors have surprisingly created multimeric fusion proteins which assemble efficiently into multimers in the absence of the L309C/H310L double mutation.

The cysteine residues created by the L309C mutation are thought to form interchain disulphide bonds with L309C cysteines on adjacent monomer units. Since these disulphides are located in very close proximity to H310, their presence may result in obstructed FcRn binding. In the multimeric fusion protein of the invention, the absence of the L309O mutation allows unimpeded binding to FcRn.

Furthermore, the absence of the cysteine residue at position 309 simplifies the isolation and purification of the multimeric fusion protein, so improving its manufacturability. It may also reduce the potential for immunogenicity.

Furthermore, by retaining the histidine residue at position 310 and preferably also at position 435, the multimeric fusion protein of the invention is capable of binding to human FcRn, and is protected from degradation, resulting in a longer half-life and greater functionality.

Thus, in one embodiment, the multimeric fusion protein of the invention binds to human FcRn.

In one embodiment, the multimeric fusion protein has a histidine residue at position 310, and preferably also at position 435. These histidine residues are important for human FcRn binding. In one embodiment, the histidine residues at positions 310 and 435 are native residues, i.e. positions 310 and 435 are not mutated. Alternatively, one or both of these histidine residues may be present as a result of a mutation.

The multimeric fusion protein of the invention may comprise one or more mutations which alter its binding to FcRn. The altered binding may be increased binding or decreased binding.

In one embodiment, the multimeric fusion protein comprises one or more mutations such that it binds to FcRn with greater affinity and avidity than the corresponding native immunoglobulin.

In one embodiment, the Fc domain is mutated by substituting the threonine residue at position 250 with a glutamine residue (T250Q).

In one embodiment, the Fc domain is mutated by substituting the methionine residue at position 252 with a tyrosine residue (M252Y)

In one embodiment, the Fc domain is mutated by substituting the serine residue at position 254 with a threonine residue (S254T).

In one embodiment, the Fc domain is mutated by substituting the threonine residue at position 256 with a glutamic acid residue (T256E).

In one embodiment, the Fc domain is mutated by substituting the threonine residue at position 307 with an alanine residue (T307A).

In one embodiment, the Fc domain is mutated by substituting the threonine residue at position 307 with a proline residue (T307P).

In one embodiment, the Fc domain is mutated by substituting the valine residue at position 308 with a cysteine residue (V308C).

In one embodiment, the Fc domain is mutated by substituting the valine residue at position 308 with a phenylalanine residue (V308F).

In one embodiment, the Fc domain is mutated by substituting the valine residue at position 308 with a proline residue (V308P).

In one embodiment, the Fc domain is mutated by substituting the glutamine residue at position 311 with an alanine residue (Q311A).

In one embodiment, the Fc domain is mutated by substituting the glutamine residue at position 311 with an arginine residue (Q311R).

In one embodiment, the Fc domain is mutated by substituting the methionine residue at position 428 with a leucine residue (M428L).

In one embodiment, the Fc domain is mutated by substituting the histidine residue at position 433 with a lysine residue (H433K).

In one embodiment, the Fc domain is mutated by substituting the asparagine residue at position 434 with a phenylalanine residue (N434F).

In one embodiment, the Fc domain is mutated by substituting the asparagine residue at position 434 with a tyrosine residue (N434Y).

In one embodiment, the Fc domain is mutated by substituting the methionine residue at position 252 with a tyrosine residue, the serine residue at position 254 with a threonine residue, and the threonine residue at position 256 with a glutamic acid residue (M252Y/S254T/T256E).

In one embodiment, the Fc domain is mutated by substituting the valine residue at position 308 with a proline residue and the asparagine residue at position 434 with a tyrosine residue (V308P/N434Y).

In one embodiment, the Fc domain is mutated by substituting the methionine residue at position 252 with a tyrosine residue, the serine residue at position 254 with a threonine residue, the threonine residue at position 256 with a glutamic acid residue, the histidine residue at position 433 with a lysine residue and the asparagine residue at position 434 with a phenylalanine residue (M252Y/S254T/T256E/H433K/N434F).

In one embodiment, the multimeric fusion protein comprises one or more mutations such that it binds to FcRn with lower affinity and avidity than the corresponding native immunoglobulin. In one embodiment, a histidine residue at position 310 is mutated to another amino acid residue. In one example, a histidine residue at position 310 is substituted with a leucine residue (H310L).

It will be appreciated that any of the mutations listed above may be combined to alter FcRn binding.

The multimeric fusion protein of the invention may comprise one or more mutations which increase its binding to FcγRIIb. FcγRIIb is the only inhibitory receptor in humans and the only Fc receptor found on B cells. B cells and their pathogenic antibodies lie at the heart of many immune diseases, and thus the multimeric fusion proteins may provide improved therapies for these diseases.

In one embodiment, the Fc domain is mutated by substituting the proline residue at position 238 with an aspartic acid residue (P238D).

In one embodiment, the Fc domain is mutated by substituting the glutamic acid residue at position 258 with an alanine residue (E258A).

In one embodiment, the Fc domain is mutated by substituting the serine residue at position 267 with an alanine residue (S267A).

In one embodiment, the Fc domain is mutated by substituting the serine residue at position 267 with a glutamic acid residue (S267E).

In one embodiment, the Fc domain is mutated by substituting the leucine residue at position 328 with a phenylalanine residue (L328F).

In one embodiment, the Fc domain is mutated by substituting the glutamic acid residue at position 258 with an alanine residue and the serine residue at position 267 with an alanine residue (E258A/S267A).

In one embodiment, the Fc domain is mutated by substituting the serine residue at position 267 with a glutamic acid residue and the leucine residue at position 328 with a phenylalanine residue (S267E/L328F).

It will be appreciated that any of the mutations listed above may be combined to increase FcγRIIb binding.

In one embodiment of the invention we provide multimeric fusion proteins which display decreased binding to FcγR. Decreased binding to FcγR may provide improved therapies for use in the treatment of immune diseases involving pathogenic antibodies.

In one embodiment the multimeric fusion protein of the present invention comprises one or more mutations that decrease its binding to FcγR.

In one embodiment, a mutation that decreases binding to FcγR is used in a multimeric fusion protein of the invention which comprises an Fc-domain derived from IgG1.

In one embodiment, the Fc domain is mutated by substituting the leucine residue at position 234 with an alanine residue (L234A).

In one embodiment, the Fc domain is mutated by substituting the phenylalanine residue at position 234 with an alanine residue (F234A).

In one embodiment, the Fc domain is mutated by substituting the leucine residue at position 235 with an alanine residue (L235A).

In one embodiment, the Fc-domain is mutated by substituting the glycine residue at position 236 with an arginine residue (G236R).

In one embodiment, the Fc domain is mutated by substituting the asparagine residue at position 297 with an alanine residue (N297A) or a glutamine residue (N297Q).

In one embodiment, the Fc domain is mutated by substituting the serine residue at position 298 with an alanine residue (S298A).

In one embodiment, the Fc domain is mutated by substituting the leucine residue at position 328 with an arginine residue (L328R).

In one embodiment, the Fc-domain is mutated by substituting the leucine residue at position 234 with an alanine residue and the leucine residue at position 235 with an alanine residue (L234A/L235A).

In one embodiment, the Fc-domain is mutated by substituting the phenylalanine residue at position 234 with an alanine residue and the leucine residue at position 235 with an alanine residue (F234A/L235A).

In one embodiment, the Fc domain is mutated by substituting the glycine residue at position 236 with an arginine residue and the leucine residue at position 328 with an arginine residue (G236R/L328R).

It will be appreciated that any of the mutations listed above may be combined to decrease FcγR binding.

In one embodiment the multimeric fusion protein of the present invention comprises one or more mutations that decrease its binding to FcγRIIIa without affecting its binding to FcγRII.

In one embodiment, the Fc domain is mutated by substituting the serine residue at position 239 with an alanine residue (S239A).

In one embodiment, the Fc domain is mutated by substituting the glutamic acid residue at position 269 with an alanine residue (E269A).

In one embodiment, the Fc domain is mutated by substituting the glutamic acid residue at position 293 with an alanine residue (E293A).

In one embodiment, the Fc domain is mutated by substituting the tyrosine residue at position 296 with a phenylalanine residue (Y296F).

In one embodiment, the Fc domain is mutated by substituting the valine residue at position 303 with an alanine residue (V303A).

In one embodiment, the Fc domain is mutated by substituting the alanine residue at position 327 with a glycine residue (A327G).

In one embodiment, the Fc domain is mutated by substituting the lysine residue at position 338 with an alanine residue (K338A).

In one embodiment, the Fc domain is mutated by substituting the aspartic acid residue at position 376 with an alanine residue (D376A).

It will be appreciated that any of the mutations listed above may be combined to decrease FcγRIIIa binding.

The multimeric fusion protein of the invention may comprise one or more mutations that alter its binding to complement. Altered complement binding may be increased binding or decreased binding.

In one embodiment the protein comprises one or more mutations which decrease its binding to C1q. Initiation of the classical complement pathway starts with binding of hexameric C1q protein to the CH2 domain of antigen bound IgG and IgM. The multimeric fusion proteins of the invention do not possess antigen binding sites, and so would not be expected to show significant binding to C1q. However, the presence of one or more mutations that decrease C1q binding will ensure that they do not activate complement in the absence of antigen engagement, so providing improved therapies with greater safety.

Thus in one embodiment the multimeric fusion protein of the invention comprises one or more mutations to decrease its binding to C1q.

In one embodiment, the Fc domain is mutated by substituting the leucine residue at position 234 with an alanine residue (L234A).

In one embodiment, the Fc domain is mutated by substituting the leucine residue at position 235 with an alanine residue (L235A).

In one embodiment, the Fc domain is mutated by substituting the leucine residue at position 235 with a glutamic acid residue (L235E).

In one embodiment, the Fc domain is mutated by substituting the glycine residue at position 237 with an alanine residue (G237A).

In one embodiment, the Fc domain is mutated by substituting the lysine residue at position 322 with an alanine residue (K322A).

In one embodiment, the Fc domain is mutated by substituting the proline residue at position 331 with an alanine residue (P331A).

In one embodiment, the Fc domain is mutated by substituting the proline residue at position 331 with a serine residue (P331S).

In one embodiment, the multimeric fusion protein comprises an Fc domain derived from IgG4. IgG4 has a naturally lower complement activation profile than IgG1, but also weaker binding of FcγR. Thus, in one embodiment, the multimeric fusion protein comprising IgG4 also comprises one or more mutations that increase FcγR binding.

It will be appreciated that any of the mutations listed above may be combined to reduce C1q binding.

The multimeric fusion protein of the invention may comprise one or more mutations to create or remove a cysteine residue. Cysteine residues have an important role in the spontaneous assembly of the multimeric fusion protein, by forming disulphide bridges between individual pairs of polypeptide monomer units. Alternatively, they may be used for chemical modification of the free SH group. Thus, by altering the number and/or position of cysteine residues, it is possible to modify the structure of the multimeric fusion protein to produce a protein with improved therapeutic properties.

The multimeric fusion protein of the present invention does not comprise a cysteine residue at position 309. The amino acid residue at position 309 may be any amino acid residue other than cysteine. In one embodiment, the amino acid residue at position 309 is the wild type residue found in the corresponding naturally occurring antibody. For example, the wild type residue found at position 309 in naturally occurring human IgG1, IgG3 and IgG4 is a leucine residue, that found in naturally occurring IgG2 is a valine residue.

In one embodiment, the antibody Fc-domain is mutated by substituting the valine residue at position 308 with a cysteine residue (V308C).

In one embodiment of the invention we provide multimeric fusion proteins with improved manufacturability comprising fewer disulphide bonds and/or glycosylation sites. These proteins have less complex disulphide bond architecture and post translational glycosylation patterns and are thus simpler and less expensive to manufacture.

In one embodiment, two disulphide bonds in the hinge region are removed by mutating a core hinge sequence CPPC to SPPS.

In one embodiment, a disulphide bond in the tailpiece is removed by substituting the cysteine residue at position 575 with a serine, threonine or alanine residue (C575S, C575T, or C575A).

In one embodiment a core hinge sequence CPPC is mutated to SPPS, and the tailpiece cysteine residue at position 575 is substituted with a serine, threonine or alanine residue (C575S, C575T, or C575A).

In one embodiment the multimeric fusion protein of the invention comprises substantially non-covalent inter-domain interactions.

In one embodiment, the multimeric fusion protein of the invention is expressed in a cell such that a practical proportion of the product is hexameric.

A practical proportion is preferably greater than or equal to 50%, for example 50-60%, 60-70%, 70-80%, 80-90%, 90-100%.

In one embodiment a glycosylation site in the CH2 domain is removed by substituting the asparagine residue at position 297 with an alanine residue (N297A) or a glutamine residue (N297Q). In addition to improved manufacturability, these aglycosyl mutants also reduce FcγR binding as described herein above.

In one embodiment, a glycosylation site in the tailpiece is removed by substituting the asparagine residue at position 563 with an alanine residue (N563A) or a glutamine residue (N563Q).

In one embodiment a glycosylation site in the CH2 domain and a glycosylation site in the tailpiece are both removed by substituting the asparagine residue at position 297 with an alanine residue or a glutamine residue, and substituting the asparagine residue at position 563 with an alanine residue or a glutamine residue (N297A/N563A or N297A/N563Q or N297Q/N563A or N297Q/N563Q).

It will be appreciated that any of the mutations listed above may be combined.

The present invention also provides an isolated DNA sequence encoding a polypeptide chain of a polypeptide monomer unit of the present invention, or a component part thereof. The DNA sequence may comprise synthetic DNA, for instance produced by chemical processing, cDNA, genomic DNA or any combination thereof.

DNA sequences which encode a polypeptide chain of a polypeptide monomer unit of the present invention can be obtained by methods well known to those skilled in the art. For example, DNA sequences coding for part or all of a polypeptide chain of a polypeptide monomer unit may be synthesised as desired from the determined DNA sequences or on the basis of the corresponding amino acid sequences.

Examples of suitable DNA sequences according to the present invention are provided in SEQ ID NOs 50-59.

Standard techniques of molecular biology may be used to prepare DNA sequences coding for a polypeptide chain of a polypeptide monomer unit of the present invention. Desired DNA sequences may be synthesised completely or in part using oligonucleotide synthesis techniques. Site-directed mutagenesis and polymerase chain reaction (PCR) techniques may be used as appropriate.

The present invention also relates to a cloning or expression vector comprising one or more DNA sequences of the present invention. Accordingly, provided is a cloning or expression vector comprising one or more DNA sequences encoding a polypeptide chain of a polypeptide monomer unit of the present invention, or a component part thereof.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding a multimeric fusion protein of the present invention. Any suitable host cell/vector system may be used for expression of the DNA sequences encoding the multimeric fusion protein of the present invention. Bacterial, for example *E. coli*, and other microbial systems such as *Saccharomyces* or *Pichia* may be used or eukaryotic, for example mammalian, host cell expression systems may also be used. Suitable mammalian host cells include CHO cells. Suitable types of chinese hamster ovary (CHO cells) for use in the present invention may include CHO and CHO-K1 cells, including dhfr-CHO cells, such as CHO-DG44 cells and CHO-DXB11 cells, which may be used with a DHFR selectable marker, or CHOK1-SV cells which may be used with a glutamine synthetase selectable marker. Other suitable host cells include NS0 cells.

The present invention also provides a process for the production of a multimeric fusion protein according to the present invention, comprising culturing a host cell containing a vector of the present invention under conditions suitable for expression of the fusion protein and assembly into multimers, and isolating and optionally purifying the multimeric fusion protein.

The multimeric fusion proteins of the present invention are expressed at good levels from host cells. Thus the properties of the multimeric fusion protein are conducive to commercial processing.

The multimeric fusion proteins of the present invention may be made using any suitable method. In one embodiment, the multimeric fusion protein of the invention may be produced under conditions which minimise aggregation. In one example, aggregation may be minimised by the addition of preservative to the culture media, culture supernatant, or purification media. Examples of suitable preservatives include thiol capping agents such as N-ethyl maleimide, iodoacetic acid, β-mercaptoethanol, β-mercaptoethylamine, glutathione, or cysteine. Other examples include disulphide inhibiting agents such as ethylenediaminetetraacetic acid (EDTA), ethyleneglycoltetraacetic acid (EGTA), or acidification to below pH 6.0.

In one embodiment there is provided a process for purifying a multimeric fusion protein of the present invention comprising the steps: performing anion exchange chromatography in non-binding mode such that the impurities are retained on the column and the antibody is eluted.

In one embodiment the purification employs affinity capture on an FcRn, FcγR or C-reactive protein column.

In one embodiment the purification employs protein A.

Suitable ion exchange resins for use in the process include Q.FF resin (supplied by GE-Healthcare). The step may, for example be performed at a pH about 8. The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filtration steps, such as a diafiltration step.

Multimers which have the required number of polypeptide monomer units can be separated according to molecular size, for example by size exclusion chromatography.

Thus in one embodiment there is provided a purified multimeric fusion protein according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

As the multimeric fusion proteins of the present invention are useful in the treatment and/or prophylaxis of a pathological condition, the present invention also provides a pharmaceutical or diagnostic composition comprising a multimeric fusion protein of the present invention in combination with one or more of a pharmaceutically acceptable excipient, diluent or carrier. Accordingly, provided is the use of an protein of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically acceptable excipient.

The present invention also provides a process for preparation of a pharmaceutical or diagnostic composition comprising adding and mixing the multimeric fusion protein of the present invention together with one or more of a pharmaceutically acceptable excipient, diluent or carrier.

The multimeric fusion protein may be the sole active ingredient in the pharmaceutical or diagnostic composition or may be accompanied by other active ingredients including other antibody ingredients or non-antibody ingredients such as steroids or other drug molecules.

The pharmaceutical compositions suitably comprise a therapeutically effective amount of the multimeric fusion protein of the invention. The term "therapeutically effective amount" as used herein refers to an amount of a therapeutic agent needed to treat, ameliorate or prevent a targeted disease or condition, or to exhibit a detectable therapeutic or preventative effect. For any medicine, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/kg. Pharmaceutical compositions may be conveniently presented in unit dose forms containing a predetermined amount of an active agent of the invention per dose.

Therapeutic doses of the multimeric fusion protein according to the present disclosure show no apparent toxicology effects in vivo.

In one embodiment of a multimeric fusion protein according to the invention a single dose may provide up to a 90% reduction in circulating IgG levels.

Compositions may be administered individually to a patient or may be administered in combination (e.g. simultaneously, sequentially or separately) with other agents, drugs or hormones.

In one embodiment the multimeric fusion proteins according to the present disclosure are employed with an immunosuppressant therapy, such as a steroid, in particular prednisone.

In one embodiment the multimeric fusion proteins according to the present disclosure are employed in combination with Rituximab or other B cell therapies.

In one embodiment the multimeric fusion proteins according to the present disclosure are employed with any B cell or T cell modulating agent or immunomodulator. Examples include methotrexate, mycophenylate and azathioprine.

The dose at which the multimeric fusion protein of the present invention is administered depends on the nature of the condition to be treated, the extent of the disease present and on whether the multimeric fusion protein is being used prophylactically or to treat an existing condition.

The frequency of dose will depend on the half-life of the multimeric fusion protein and the duration of its effect. If the multimeric fusion protein has a short half-life (e.g. 2 to 10 hours) it may be necessary to give one or more doses per day. Alternatively, if the multimeric fusion protein has a long half-life (e.g. 2 to 15 days) and/or long lasting pharmacodynamic effects it may only be necessary to give a dosage once per day, once per week or even once every 1 or 2 months.

In one embodiment the dose is delivered bi-weekly, i.e. twice a month.

Half-life as employed herein is intended to refer to the duration of the molecule in circulation, for example in serum/plasma.

Pharmacodynamics as employed herein refers to the profile and in particular duration of the biological action of the multimeric fusion protein according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles. Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. The protein may be in the form of nanoparticles. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the multimeric fusion protein, for example if the pI of the protein is in the range 8-9 or above then a formulation pH of 7 may be appropriate. Whilst not wishing to be bound by theory it is thought that this may ultimately provide a final formulation with improved stability, for example the multimeric fusion protein remains in solution.

In one example the pharmaceutical formulation at a pH in the range of 4.0 to 7.0 comprises: 1 to 200 mg/mL of an protein molecule according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule It will be appreciated that the active ingredient in the composition will be an protein molecule. As such, it will be susceptible to degradation in the gastrointestinal tract. Thus, if the composition is to be administered by a route using the gastrointestinal tract, the composition will need to contain agents which protect the protein from degradation but which release the protein once it has been absorbed from the gastrointestinal tract.

A thorough discussion of pharmaceutically acceptable carriers is available in Remington's Pharmaceutical Sciences (Mack Publishing Company, N.J. 1991). In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient. These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 1 to 5 µm. The particle size of the active ingredient (such as the antibody or fragment) is of primary importance.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellant-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The multimeric fusion protein of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised protein.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the protein in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The multimeric fusion proteins disclosed herein may be suitable for delivery via nebulisation.

It is also envisaged that the proteins of the present invention may be administered by use of gene therapy. In order to achieve this, DNA sequences encoding the polypeptide chains of the protein molecule under the control of appropriate DNA components are introduced into a patient such that the polypeptide chains are expressed from the DNA sequences and assembled in situ.

In one embodiment we provide the multimeric fusion protein of the invention for use in therapy.

In one embodiment we provide the multimeric fusion protein of the invention for use in the treatment of immune disorders.

In one embodiment we provide the use of the multimeric fusion protein of the invention for the preparation of a medicament for the treatment of immune disorders.

Examples of immune disorders which may be treated using the multimeric fusion protein of the invention include immune thrombocytopenia (ITP), chronic inflammatory demyelinating polyneuropathy (CIDP), Kawasaki disease and Guillain-Barre syndrome (GBS).

The present invention also provides a multimeric fusion protein (or compositions comprising same) for use in the control of autoimmune diseases, for example Acute Disseminated Encephalomyelitis (ADEM), Acute necrotizing hemorrhagic leukoencephalitis, Addison's disease, Agammaglobulinemia, Alopecia areata, Amyloidosis, ANCA-associated vasculitis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticarial, Axonal & nal neuropathies, Balo disease, Behcet's disease, Bullous pemphigoid, Cardiomyopathy, Castleman disease, Celiac disease, Chagas disease, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Dilated cardiomyopathy, Discoid lupus, Dressler's syndrome, Endometriosis, Eosinophilic angiocentric fibrosis, Eosinophilic fasciitis, Erythema nodosum, Experimental allergic encephalomyelitis, Evans syndrome, Fibrosing alveolitis, Giant cell arteritis (temporal arteritis), Glomerulonephritis, Goodpasture's syndrome, Granulomatosis with Polyangiitis (GPA) see Wegener's, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic hypocomplementemic tubulointestitial nephritis, Idiopathic thrombocytopenic purpura (ITP), IgA nephropathy, IgG4-related disease, IgG4-related sclerosing disease, Immunoregulatory lipoproteins, Inflammatory aortic aneurysm, Inflammatory pseudotumour, Inclusion body myositis, Insulin-dependent diabetes (type1), Interstitial cystitis, Juvenile arthritis, Juvenile diabetes, Kawasaki syndrome, Kuttner's tumour, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Mediastinal fibrosis, Meniere's disease, Microscopic polyangiitis, Mikulicz's syndrome, Mixed connective tissue disease (MCTD), Mooren's ulcer, Mucha-Habermann disease, Multifocal fibrosclerosis, Multiple sclerosis, Myasthenia gravis, Myositis, Narcolepsy, Neuromyelitis optica (Devic's), Neutropenia, Ocular cicatricial pemphigoid, Optic neuritis, Ormond's disease (retroperitoneal fibrosis), Palindromic rheumatism, PANDAS (Pediatric Autoimmune Neuropsychiatric Disorders Associated with *Streptococcus*), Paraneoplastic cerebellar degeneration, Paraproteinemic polyneuropathies, Paroxysmal nocturnal hemoglobinuria (PNH), Parry Romberg syndrome, Parsonnage-Turner syndrome, Pars planitis (peripheral uveitis), Pemphigus vulgaris, Periaortitis, Periarteritis, Peripheral neuropathy, Perivenous encephalomyelitis, Pernicious anemia, POEMS syndrome, Polyarteritis nodosa, Type I, II, & Ill autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis (Ormond's disease), Rheumatic fever, Rheumatoid arthritis, Riedel's thyroiditis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/ Giant cell arteritis, Thrombotic, thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, Waldenstrom Macroglobulinaemia, Warm idiopathic haemolytic anaemia and Wegener's granulomatosis (now termed Granulomatosis with Polyangiitis (GPA).

In one embodiment the multimeric fusion proteins and fragments according to the disclosure are employed in the treatment or prophylaxis of epilepsy or seizures.

In one embodiment the multimeric fusion proteins and fragments according to the disclosure are employed in the treatment or prophylaxis of multiple sclerosis.

In embodiment the multimeric fusion proteins and fragments of the disclosure are employed in the treatment or prophylaxis of alloimmune disease/indications which include:

Transplantation donor mismatch due to anti-HLA antibodies

Foetal and neonatal alloimmune thrombocytopenia, FNAIT (or neonatal alloimmune thrombocytopenia, NAITP or NAIT or NAT, or foeto-maternal alloimmune thrombocytopenia, FMAITP or FMAIT).

Additional indications include: rapid clearance of Fc-containing biopharmaceutical drugs from human patients and combination of multimeric fusion protein therapy with other therapies—IVIg, Rituxan, plasmapheresis. For example multimeric fusion protein therapy may be employed following Rituxan therapy.

In one embodiment the multimeric fusion proteins of the disclosure are employed in the treatment or prophylaxis of a neurology disorder such as:
  Chronic inflammatory demyelinating polyneuropathy (CIDP)
  Guillain-Barre syndrome
  Paraproteinemic polyneuropathies
  Neuromyelitis optica (NMO, NMO spectrum disorders or NMO spectrum diseases), and
  Myasthenia gravis.

In one embodiment the multimeric fusion proteins of the disclosure are employed in a dermatology disorder such as:
  Bullous pemphigoid
  Pemphigus vulgaris
  ANCA-associated vasculitis
  Dilated cardiomyopathy In one embodiment the multimeric fusion proteins of the disclosure are employed in an immunology or haematology disorder such as:
  Idiopathic thrombocytopenic purpura (ITP)
  Thrombotic thrombocytopenic purpura (TTP)
  Warm idiopathic haemolytic anaemia
  Goodpasture's syndrome
  Transplantation donor mismatch due to anti-HLA antibodies In one embodiment the disorder is selected from Myasthenia Gravis, Neuro-myelitis Optica, CIDP, Guillaume-Barre Syndrome, Para-proteinemic Poly neuropathy, Refractory Epilepsy, ITP/TTP, Hemolytic Anemia, Goodpasture's Syndrome, ABO mismatch, Lupus nephritis, Renal Vasculitis, Sclero-derma, Fibrosing alveolitis, Dilated cardiomyopathy, Grave's Disease, Type 1 diabetes, Auto-immune diabetes, Pemphigus, Sclero-derma, Lupus, ANCA vasculitis, Dermato-myositis, Sjogren's Disease and Rheumatoid Arthritis.

In one embodiment the disorder is selected from autoimmune polyendocrine syndrome types 1 (APECED or Whitaker's Syndrome) and 2 (Schmidt's Syndrome); alopecia universalis; myasthenic crisis; thyroid crisis; thyroid associated eye disease; thyroid ophthalmopathy; autoimmune diabetes; autoantibody associated encephalitis and/or encephalopathy; pemphigus foliaceus; epidermolysis bullosa; dermatitis herpetiformis; Sydenham's chorea; acute motor axonal neuropathy (AMAN); Miller-Fisher syndrome; multifocal motor neuropathy (MMN); opsoclonus; inflammatory myopathy; Isaac's syndrome (autoimmune neuromyotonia), Paraneoplastic syndromes and Limbic encephalitis.

The multimeric fusion protein according to the present disclosure may be employed in treatment or prophylaxis.

The present invention also provides a method of reducing the concentration of undesired antibodies in an individual comprising the steps of administering to an individual a therapeutically effective dose of a multimeric fusion protein described herein.

The multimeric fusion protein of the present invention may also be used in diagnosis, for example in the in vivo diagnosis and imaging of disease states involving Fc-receptors, such as B-cell related lymphomas.

FIGURE LEGENDS

FIG. 1 Example of an expression construct and a multimeric fusion protein according to the invention. SP is signal peptide, CH2 and CH3 are heavy chain constant domains, TP is tailpiece.

FIG. 2 Example Sequences

2(*a*) Example amino acid sequences of a polypeptide chain of a polypeptide monomer unit. In each sequence, the tailpiece sequence is underlined, and any mutations are shown in bold and underlined. The hinge is in bold. In constructs comprising a CH4 domain from IgM, this region is shown in italics.

2(*b*) Example amino acid sequences for an Fc-multimer polypeptide chain comprising a CH2 and CH3 domain derived from IgG1 or a CH2 and CH3 domain derived from IgG4. In each sequence, the positions of difference between IgG1 and IgG4 are in bold and highlighted.

2(*c*) Example amino acid sequences for Fc-multimers designed to combine certain selected properties of IgG1 and certain selected properties of IgG4. The mutations are shown in bold and underlined.

2(*d*) Example amino acid sequences for Fc-multimers with hybrid heavy chain Fc-regions engineered by domain exchange.

2(*e*) Example amino acid sequences for Fc-multimers with hybrid heavy chain Fc-regions and additional mutations, that have been engineered to combine certain selected properties of IgG1 and certain selected properties of IgG4.

2(f) DNA and amino acid sequences of the B72.3 signal peptide. (i) DNA sequence, (ii) amino acid sequence.

2(g) Example DNA sequences for Fc-multimers.

FIG. 3 Role of the CH3 domain in Fc-multimer assembly

3(a) Size exclusion chromatography traces showing the effect of IgG1/IgG4 CH3 domain exchange on hexamerisation of Fc-multimers.

3(b) Effect of point mutations in the CH3 domain on hexamerisation of IgG1 Fc IgM tp.

3(c) High levels of hexamerisation of IgG4 Fc IgM tp are achieved by point mutation Q355R.

3(d) Effect of mutagenesis of R355 to all other amino acids in IgG1 Fc IgM tp.

Figure 4:
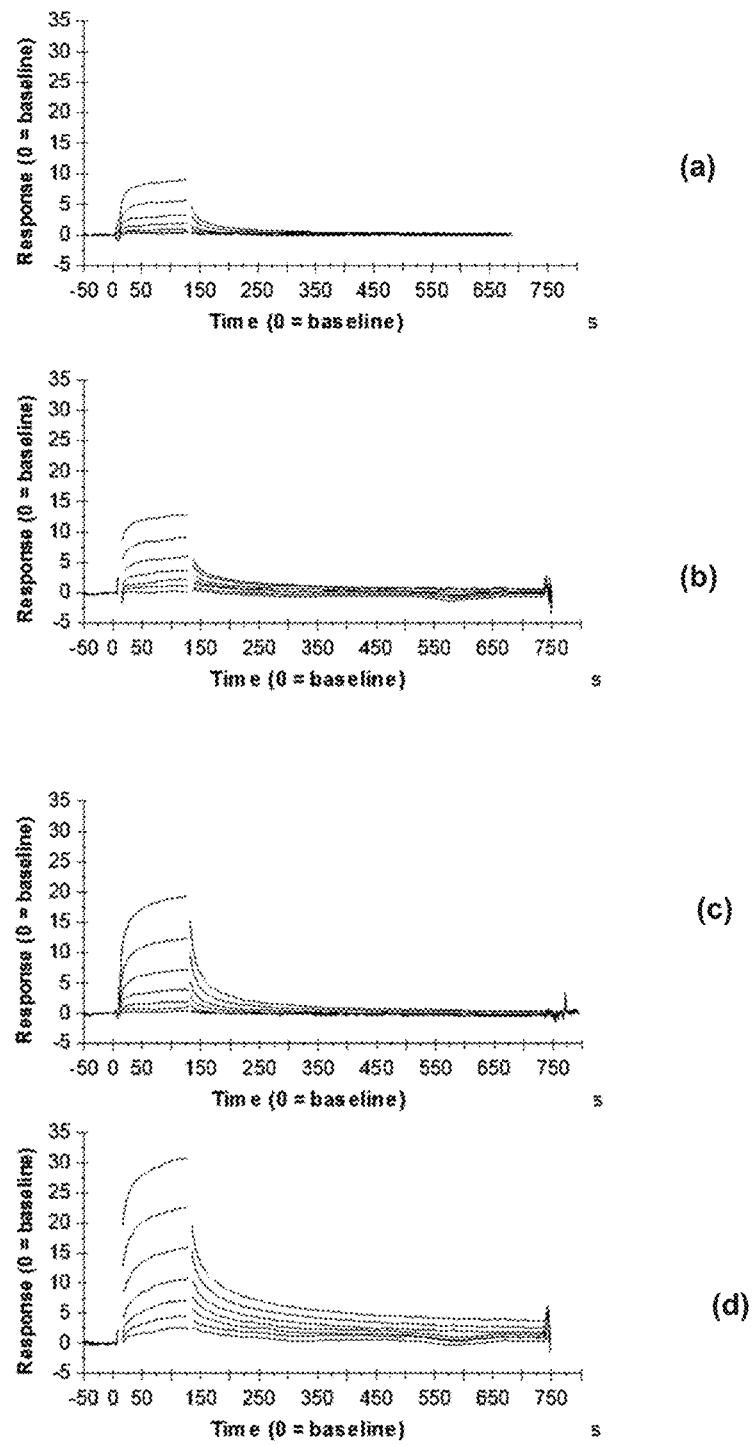

FIG. 4 Binding of Fc-multimers to FcRn, measured by surface plasmon resonance analysis. The traces demonstrate binding for multimer concentration range: 2.5 µM, 1.25 µM, 0.625 µM, 0.3125 µM, 0.15625 µM, 0.078125 µM, 0.0390625 µM. The Fc-multimers shown all comprised histidine at position 310.

4(a) hIgG1 Fc-multimer IgM tp L309C binding to low density FcRn.

4(b) hIgG1 Fc-multimer IgM tp binding to low density FcRn.

4(c) hIgG1 Fc-multimer IgM tp L309C binding to high density FcRn.

4(d) hIgG1 Fc-multimer IgM tp binding to high density FcRn.

Figure 5:
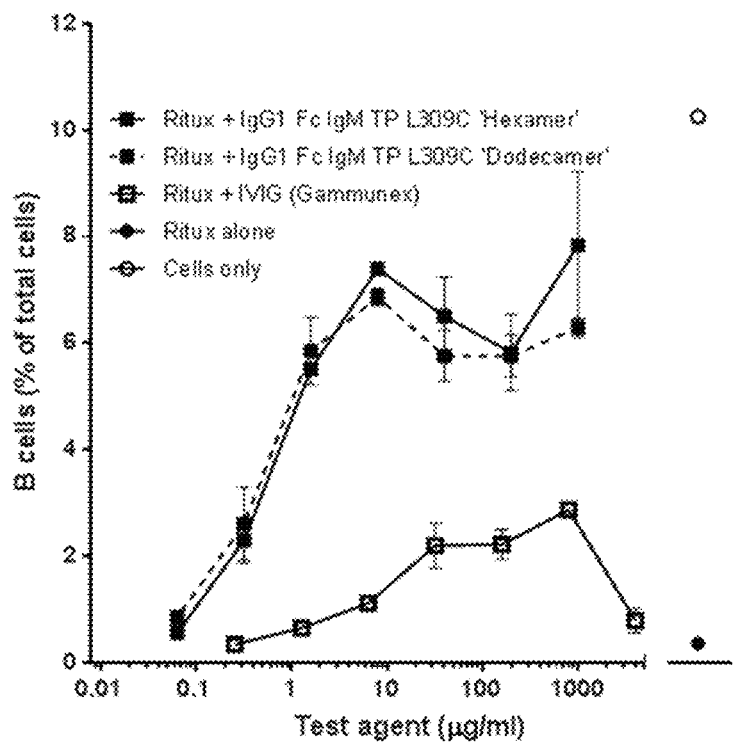
Figure 5:
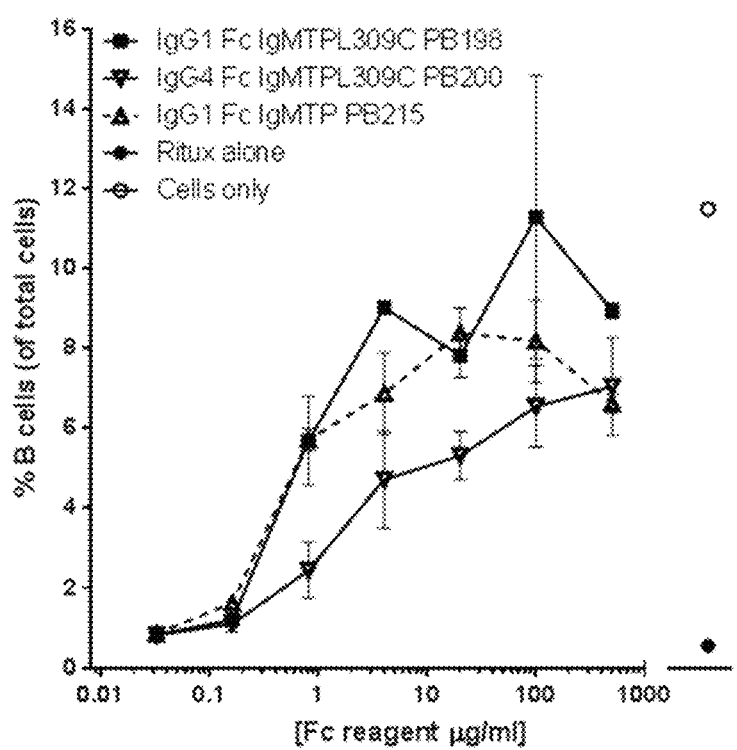

FIG. 5 Fc-multimer inhibition of macrophage phagocytosis. The data show that Fc-multimers derived from human IgG1 or IgG4, polymerised into hexamer or dodecamer forms by IgM tailpiece alone, or IgM tailpiece and L309C, all exhibit potency and maximum levels of inhibition significantly better than human IVIG.

Figure 6:
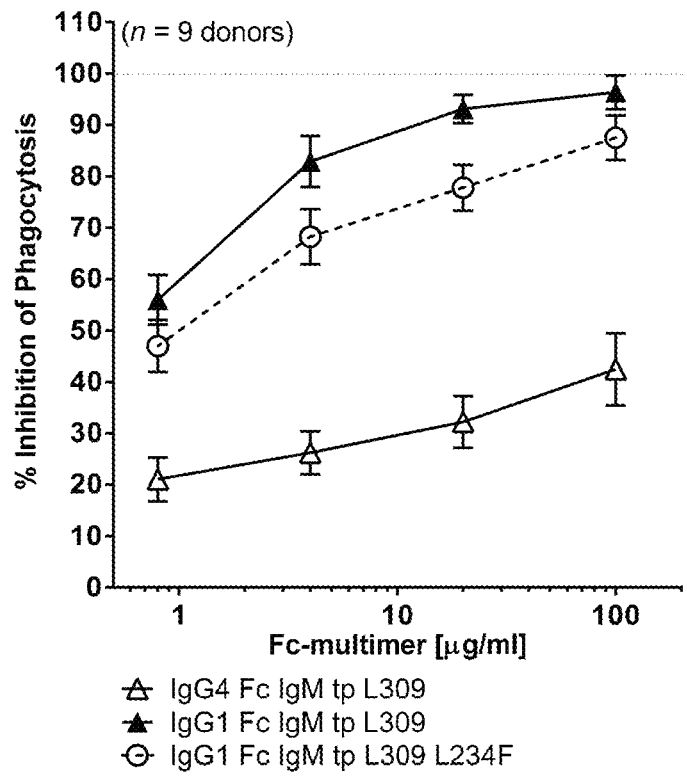
Figure 6:
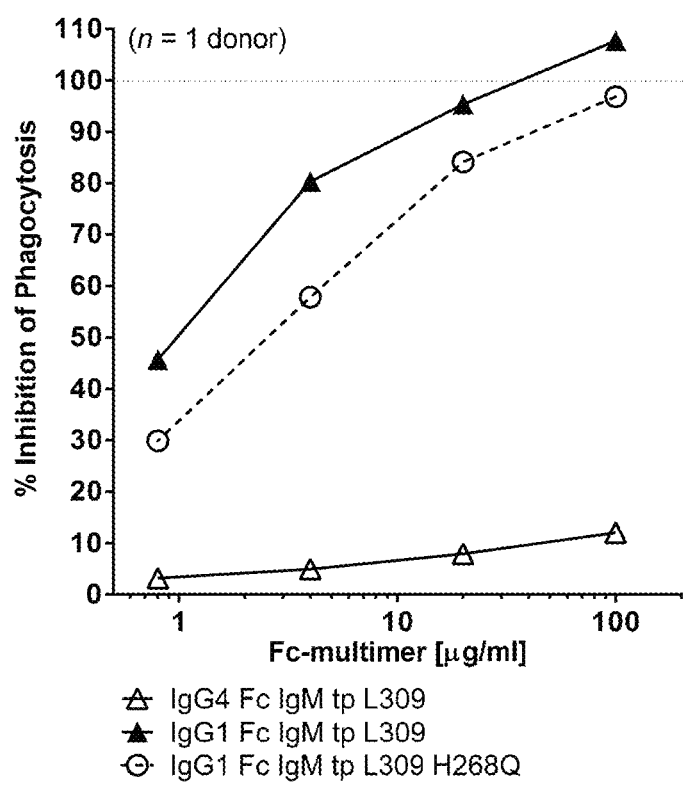
Figure 6:
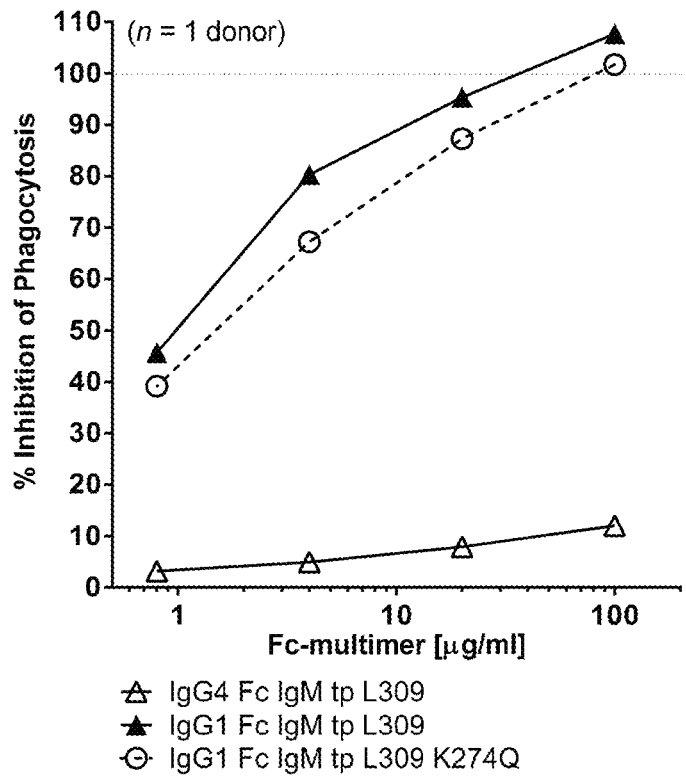
Figure 6:
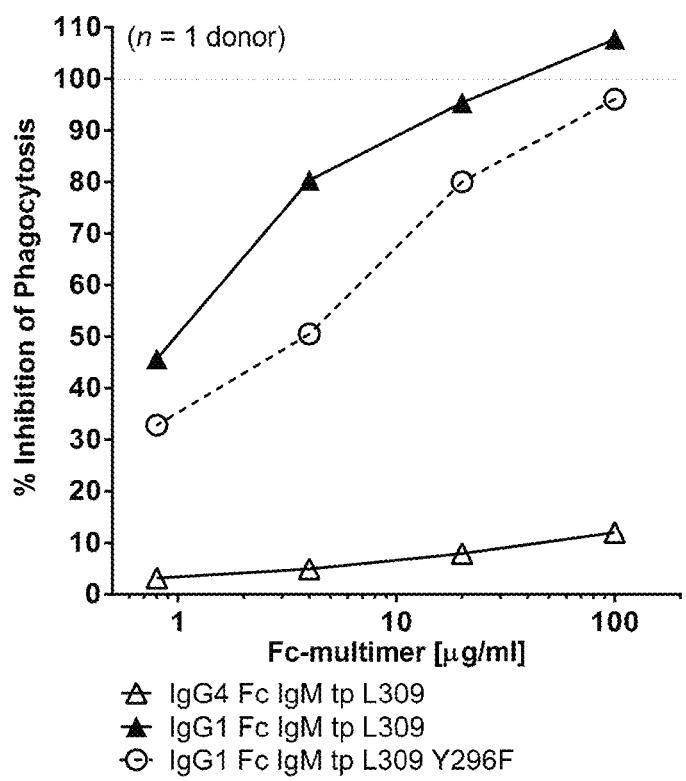
Figure 6:
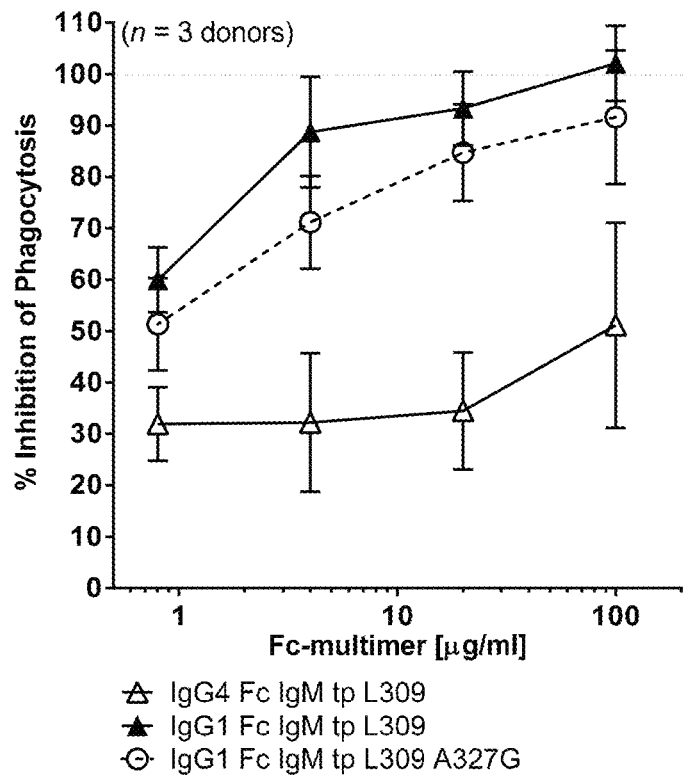
Figure 6:
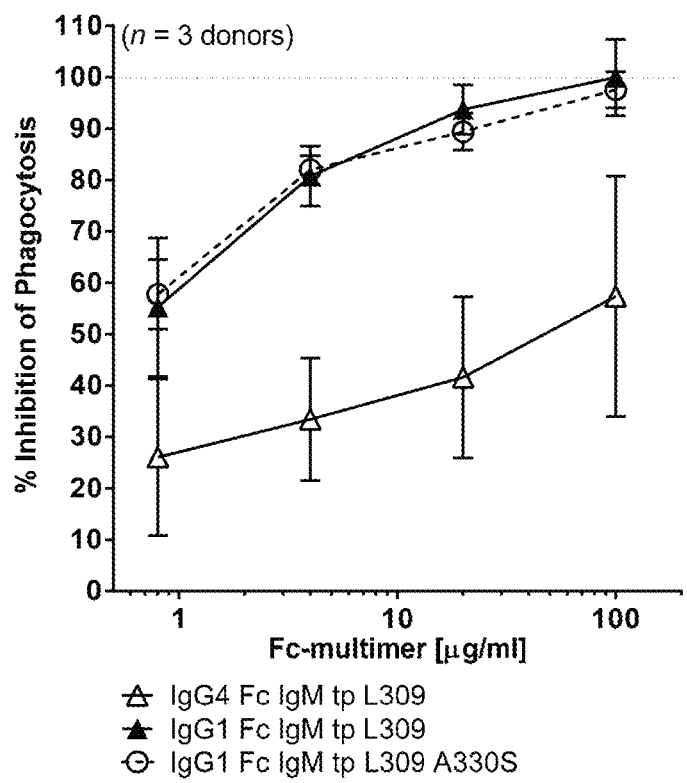
Figure 6:
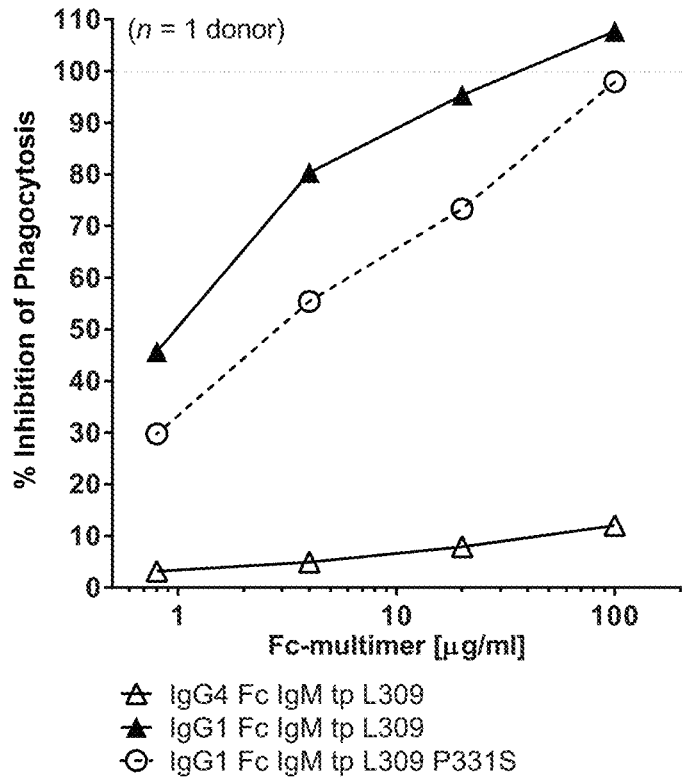
Figure 6:
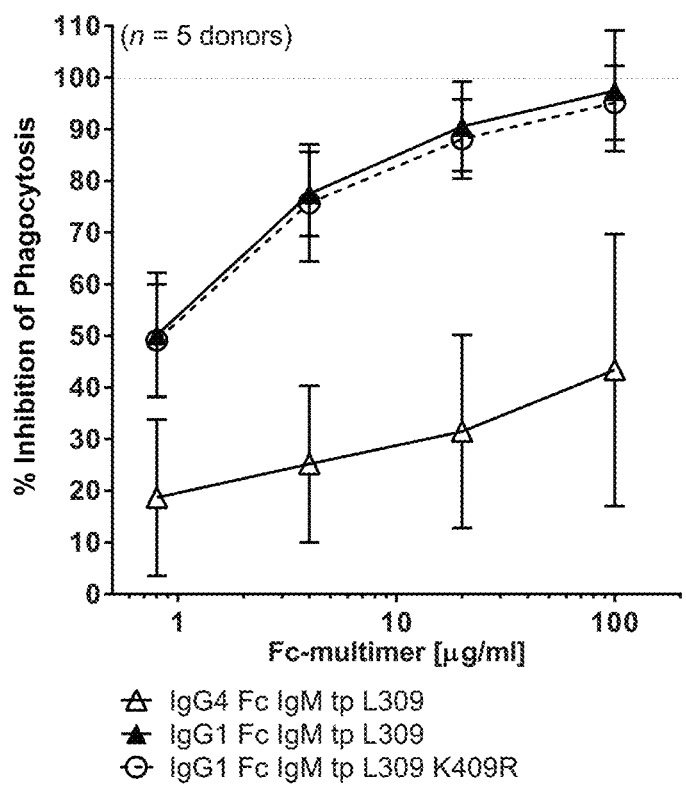
Figure 6:
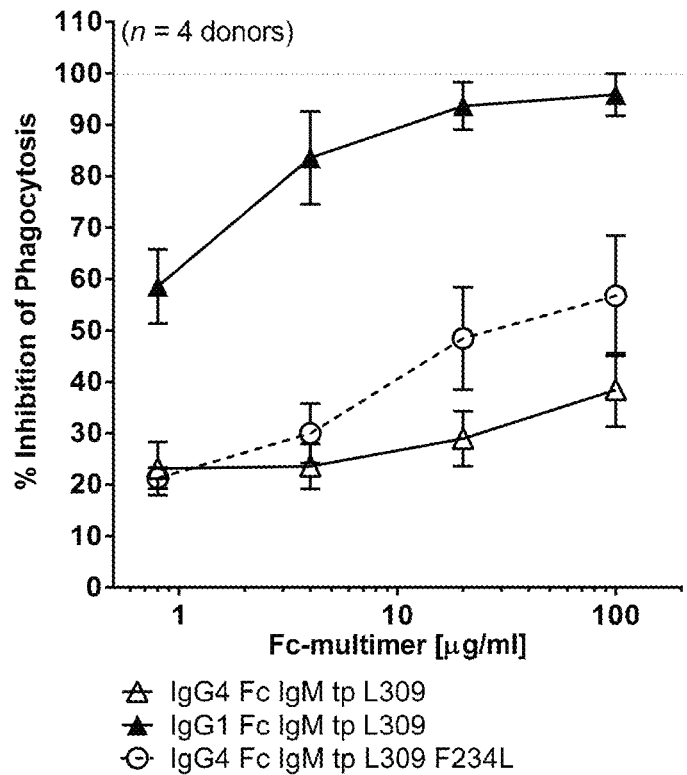
Figure 6:
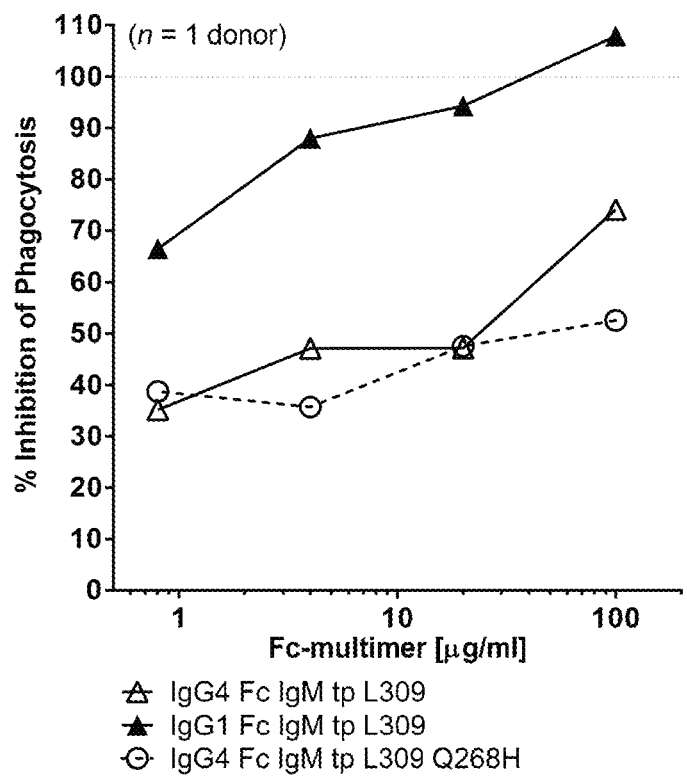
Figure 6:
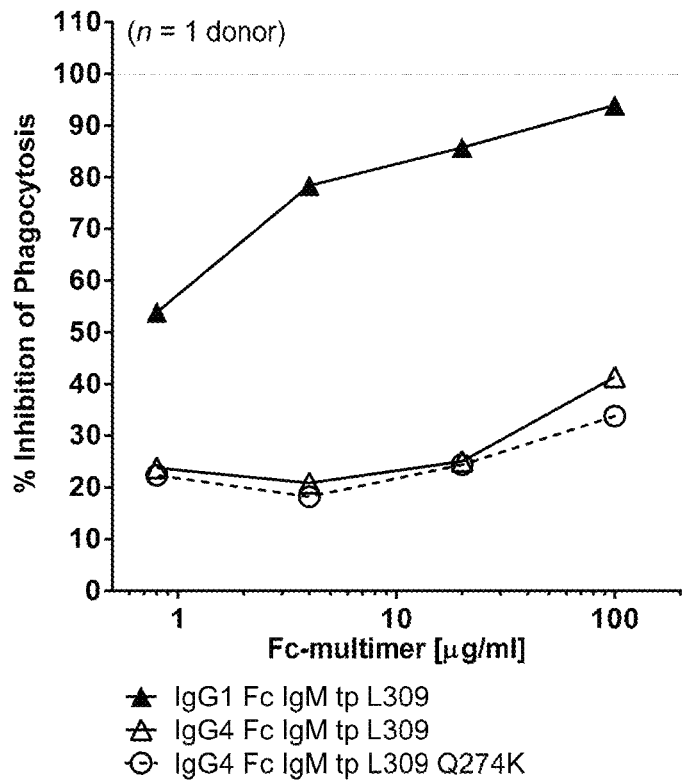
Figure 6:
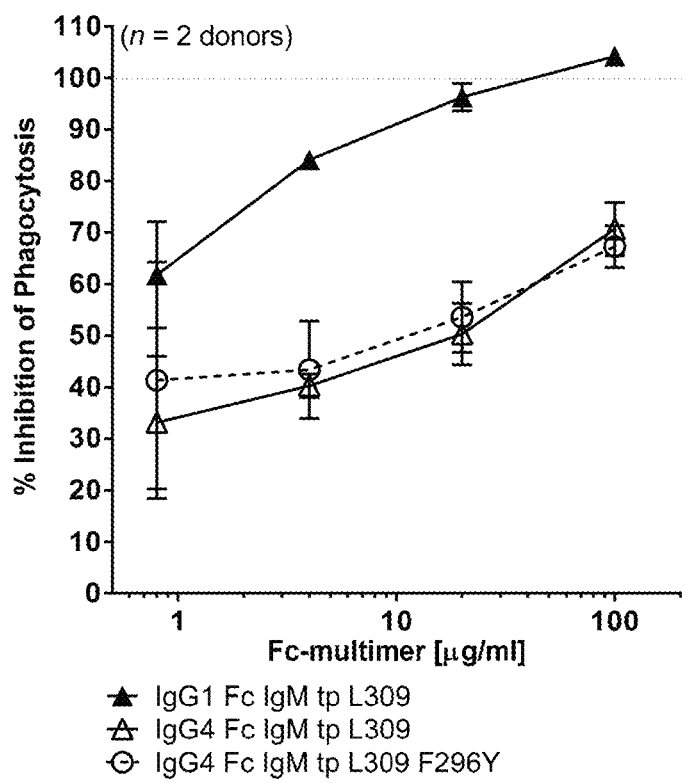
Figure 6:
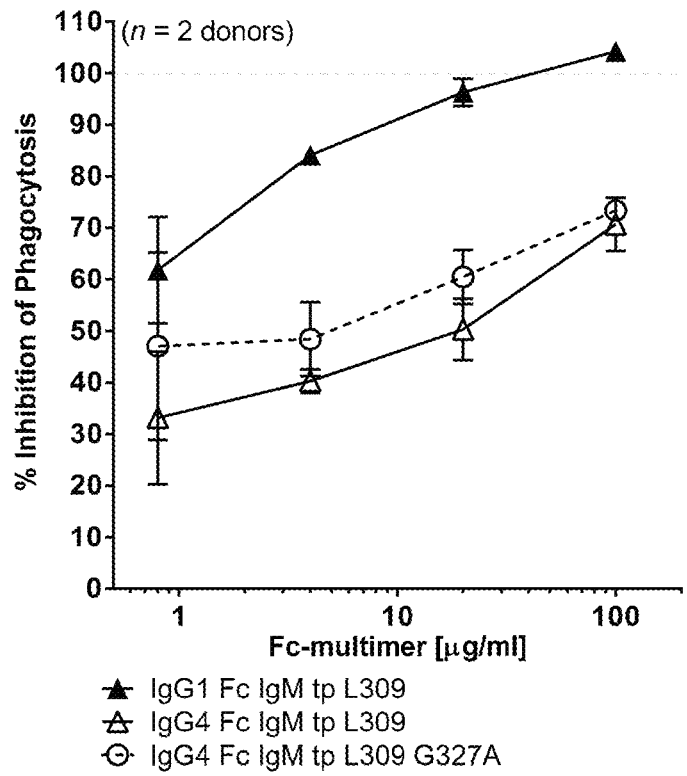
Figure 6:
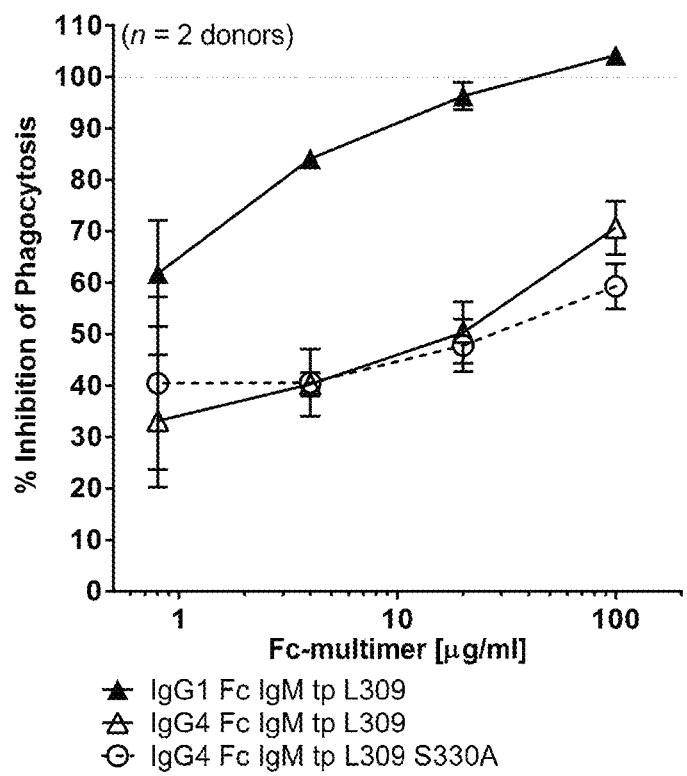
Figure 6:
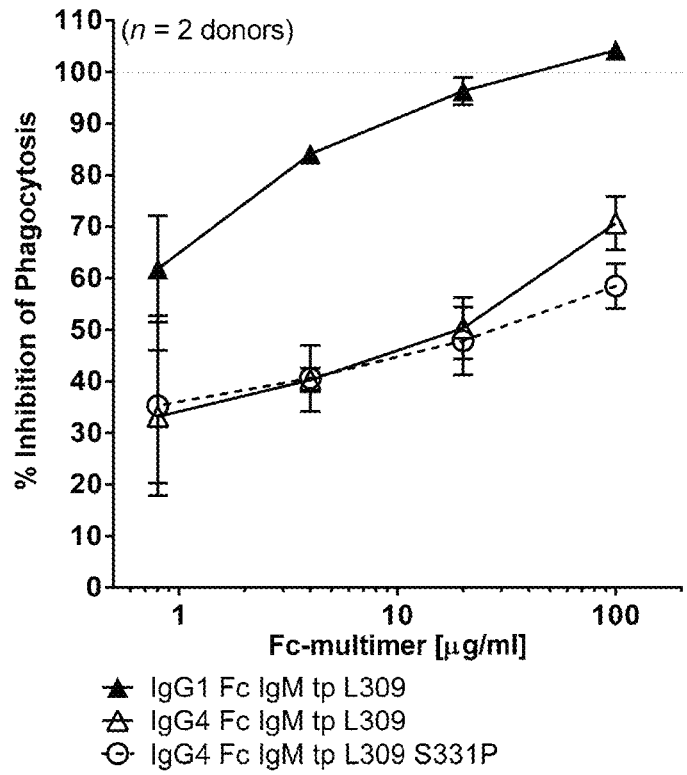
Figure 6:
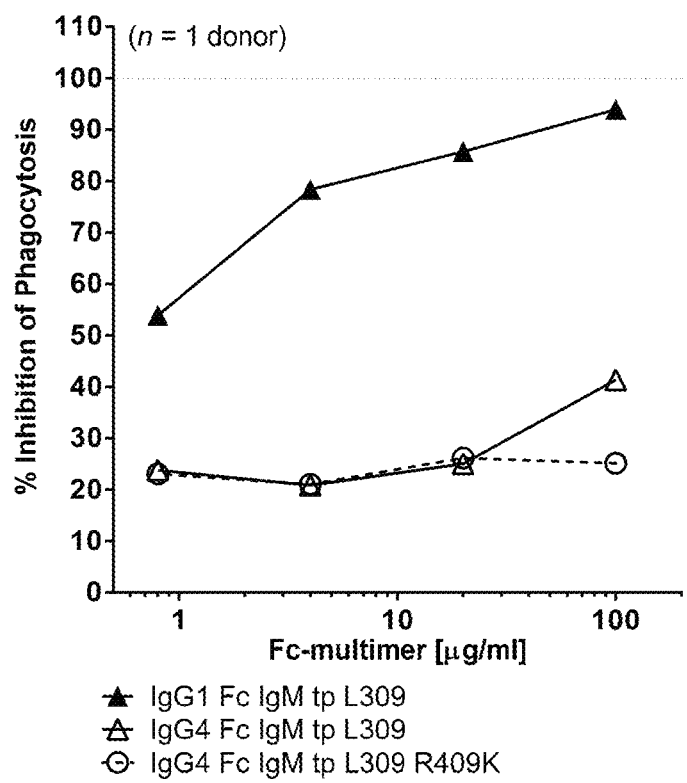

FIG. 6 Fc-multimer inhibition of macrophage phagocytosis. The data show the inhibitory effects of Fc-multimers comprising a single cross-over mutation at a selected position of difference between the IgG1 and IgG4 Fc region.

FIG. 7 Fc-multimer inhibition of macrophage phagocytosis. The data show the inhibitory effects of Fc-multimers designed for use in the treatment of immune disorders.

Figure 8:
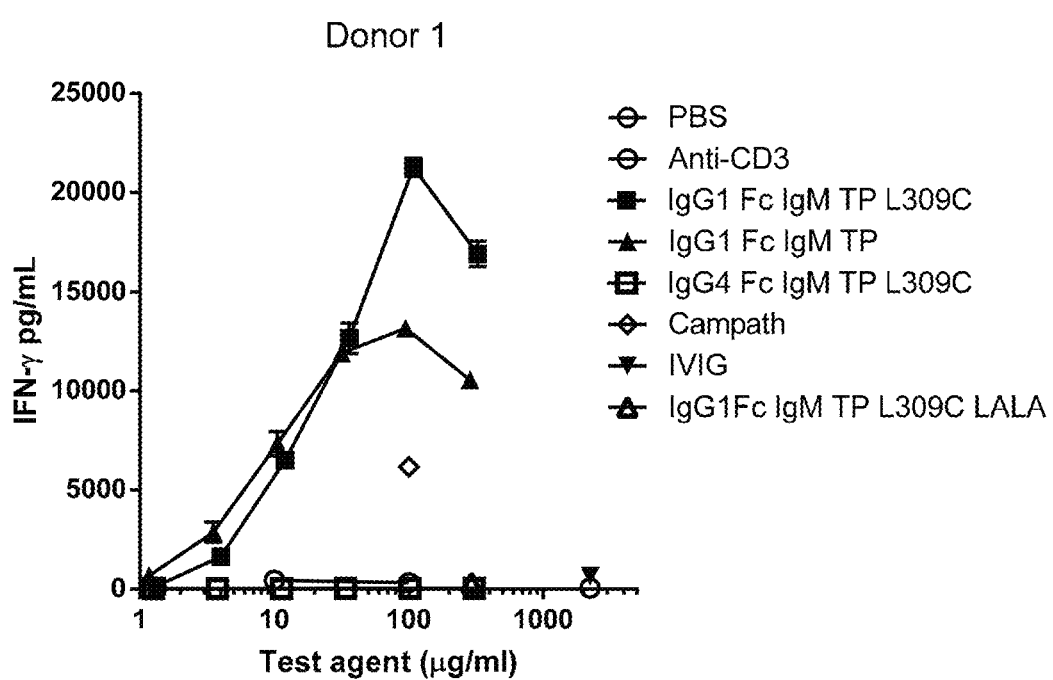

FIG. 8 Stimulation of cytokine release by Fc-multimers. The data demonstrated that wild type IgG1 Fc-multimers, both with and without L309C, stimulate very high levels of cytokine release. The observed levels of cytokines were higher than those produced by the positive control anti-CD52 antibody, Campath. In marked contrast, IgG4 Fc-multimers, and IgG1 Fc-multimers comprising the FcγR and C1q inert "LALA" mutation (L234A L235A), produced virtually zero cytokine release.

Figure 9:
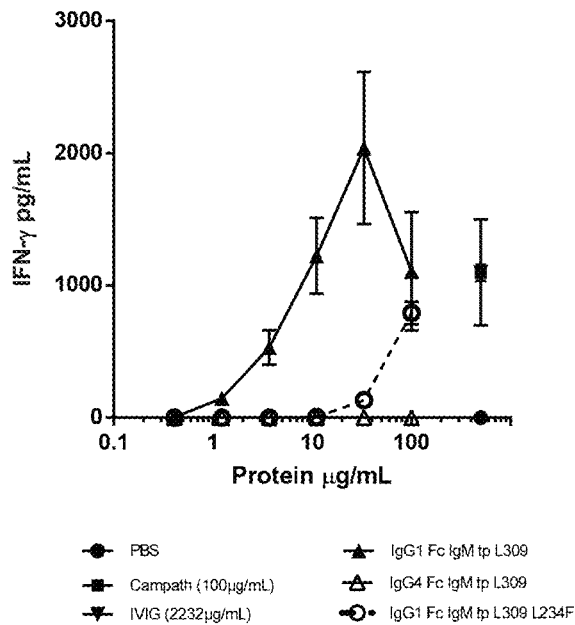
Figure 9:
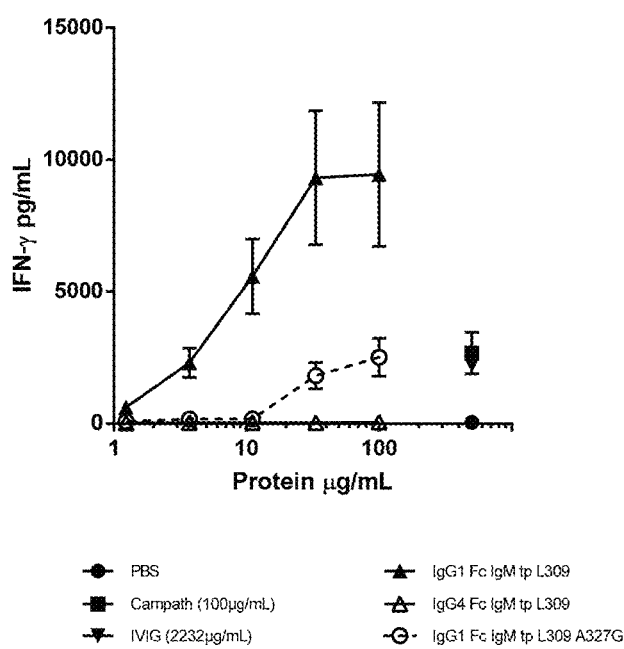
Figure 9:
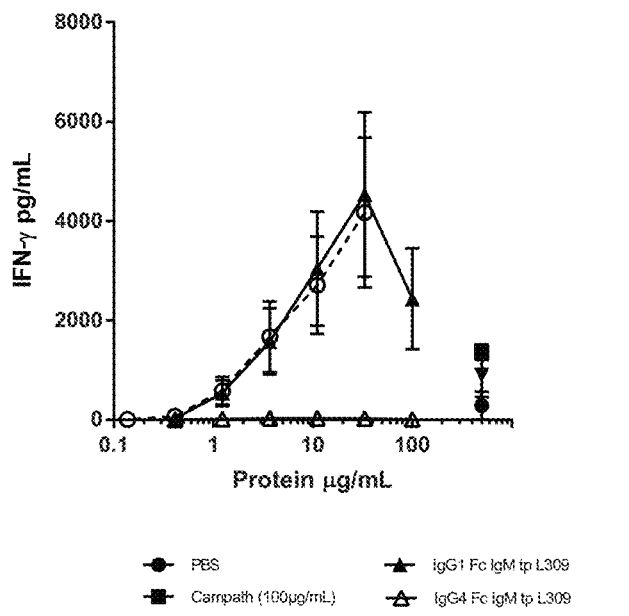
Figure 9:
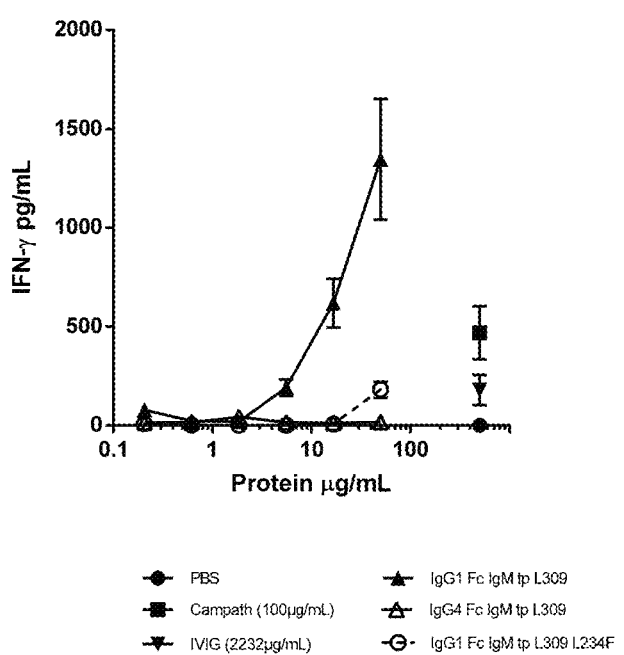
Figure 9:
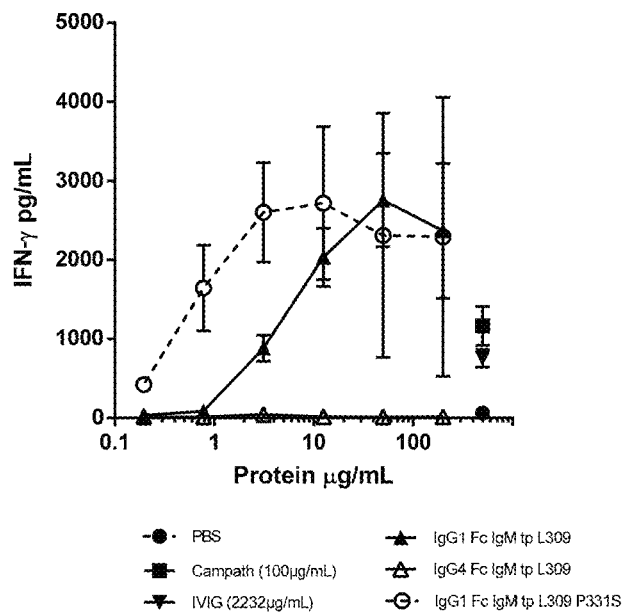
Figure 9:
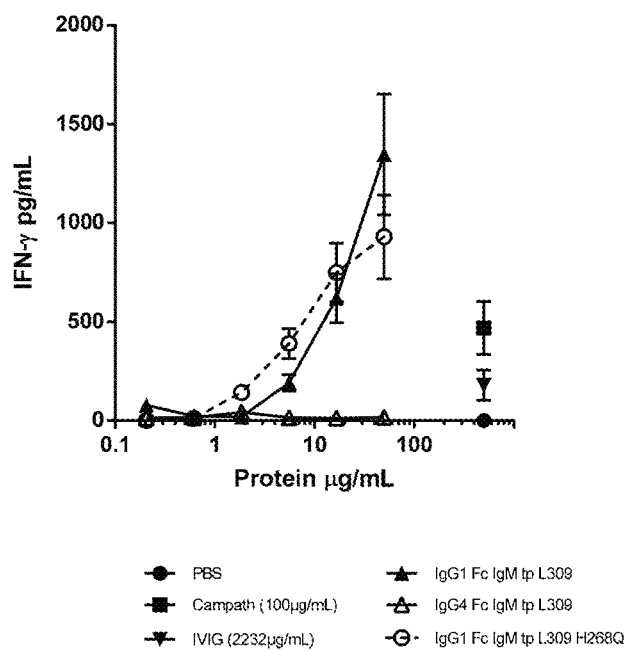
Figure 9:
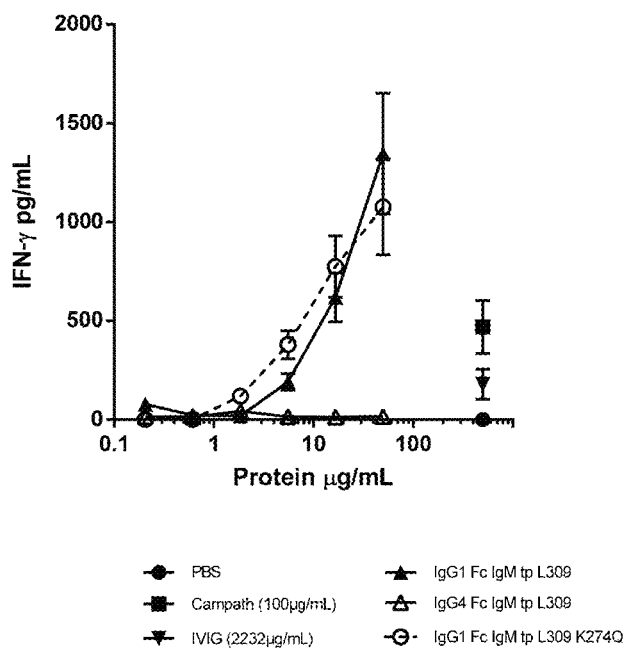
Figure 9:
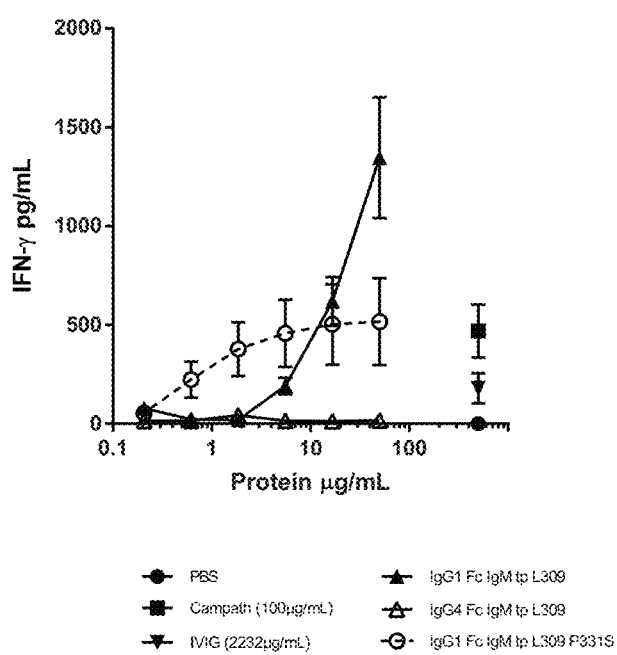
Figure 9:
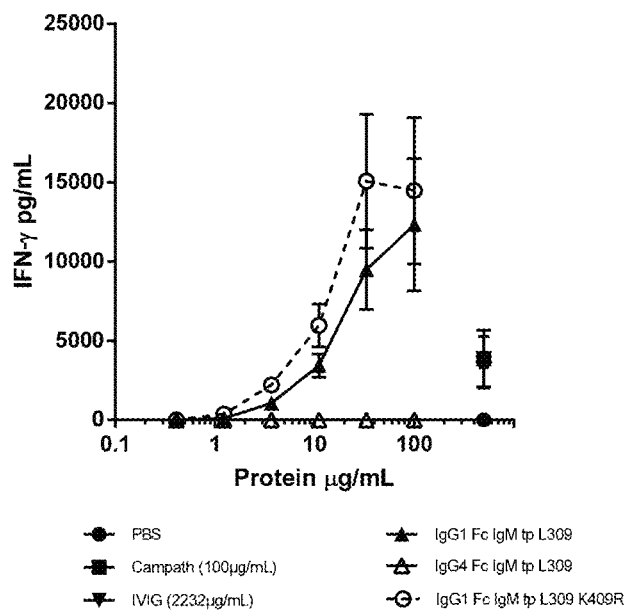
Figure 9:
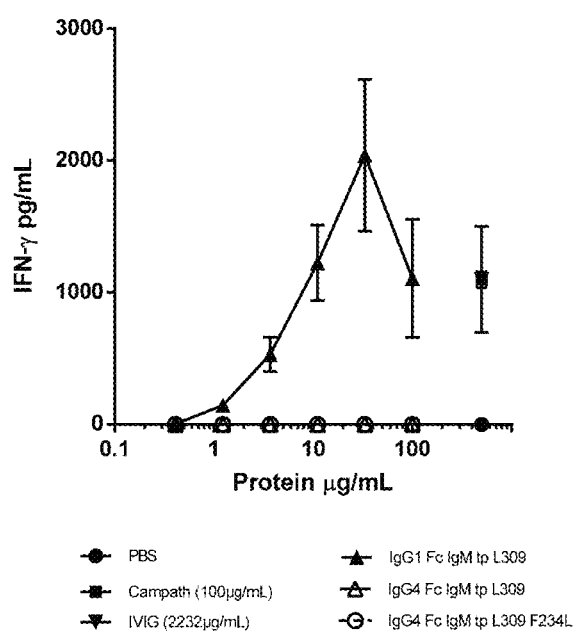
Figure 9:
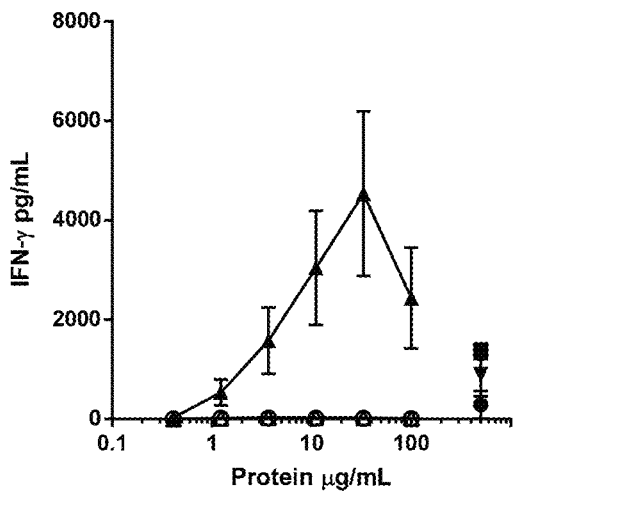
Figure 9:
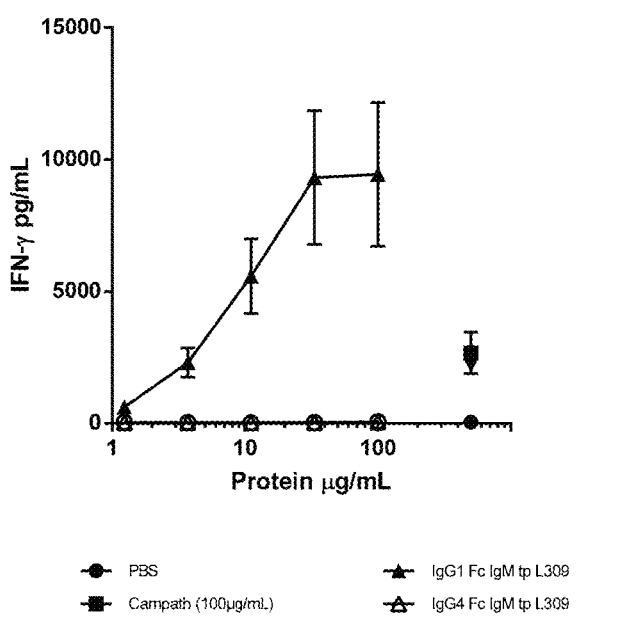
Figure 9:
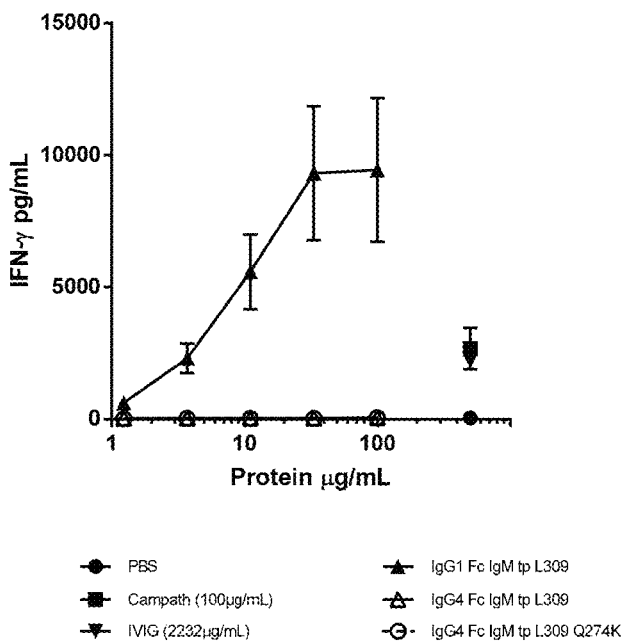
Figure 9:
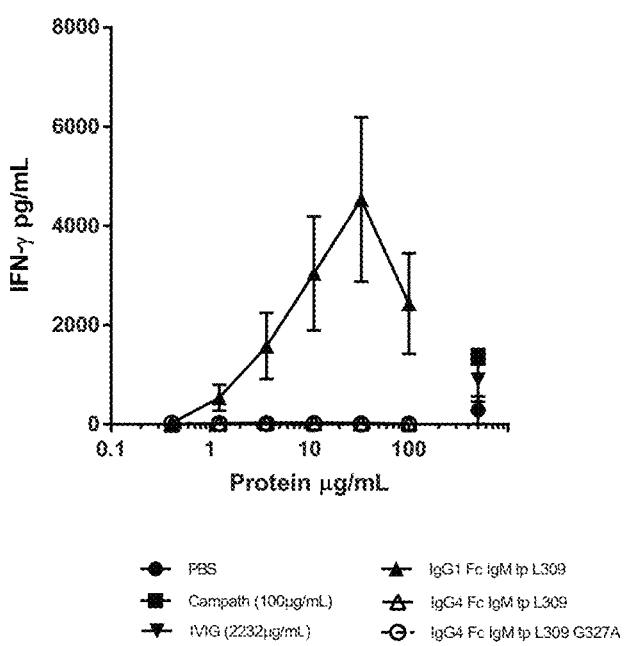
Figure 9:
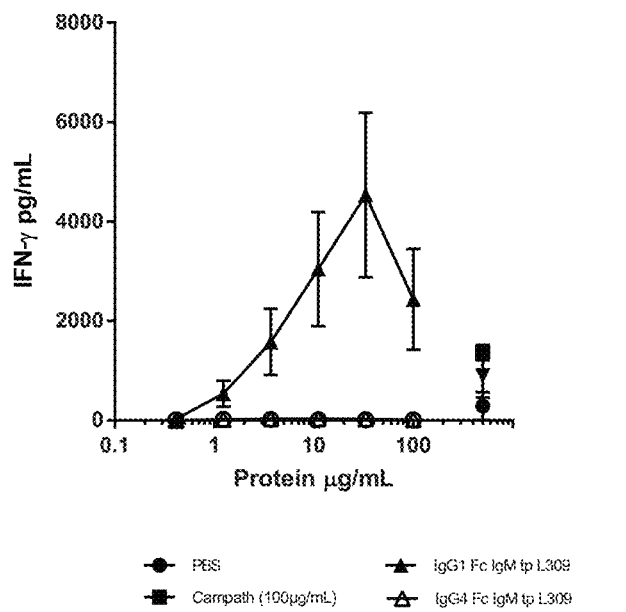
Figure 9:
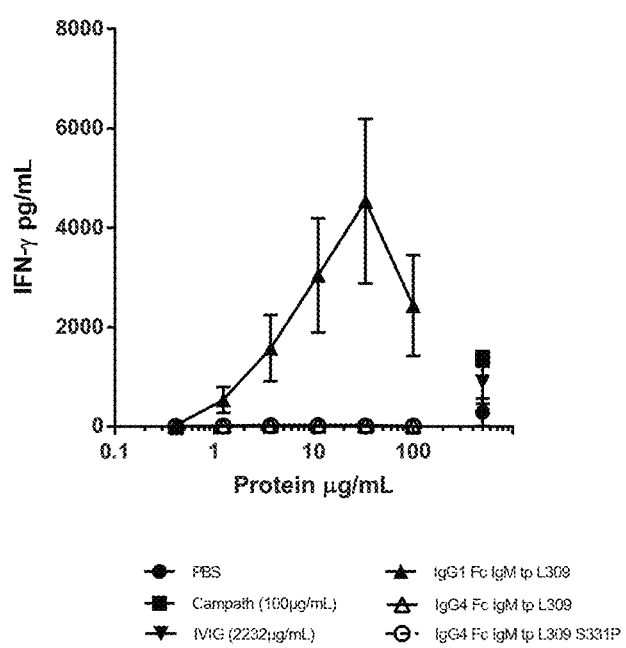
Figure 9:
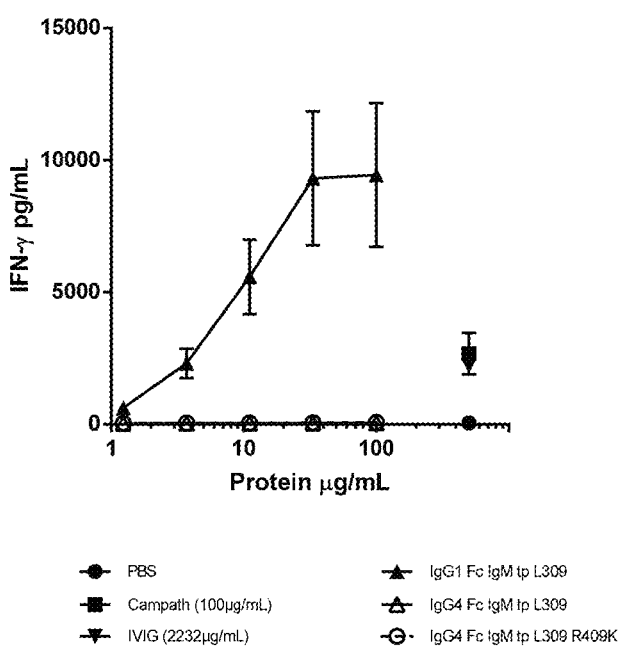

FIG. 9 Stimulation of cytokine release by Fc-multimers. The data show the effects of Fc-multimers comprising a single cross-over mutation at a selected position of difference between the IgG1 and IgG4 Fc region.

Figure 10:
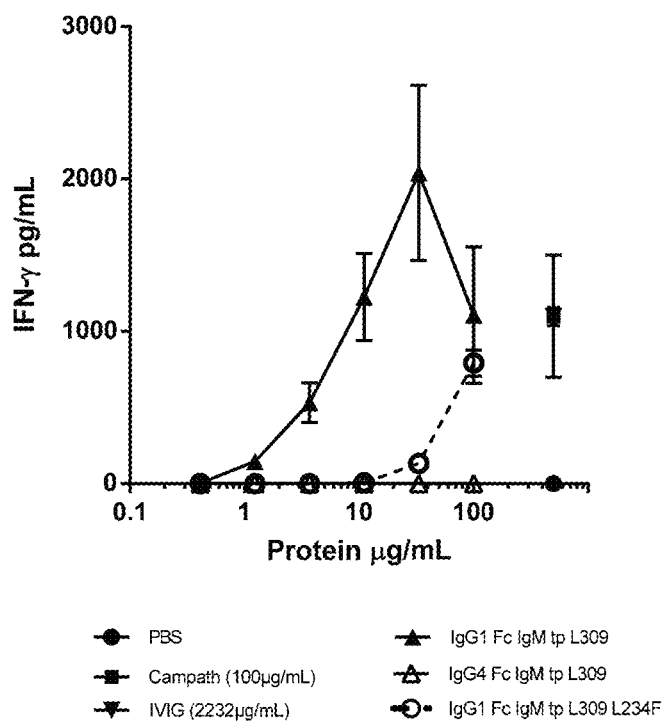
Figure 10:
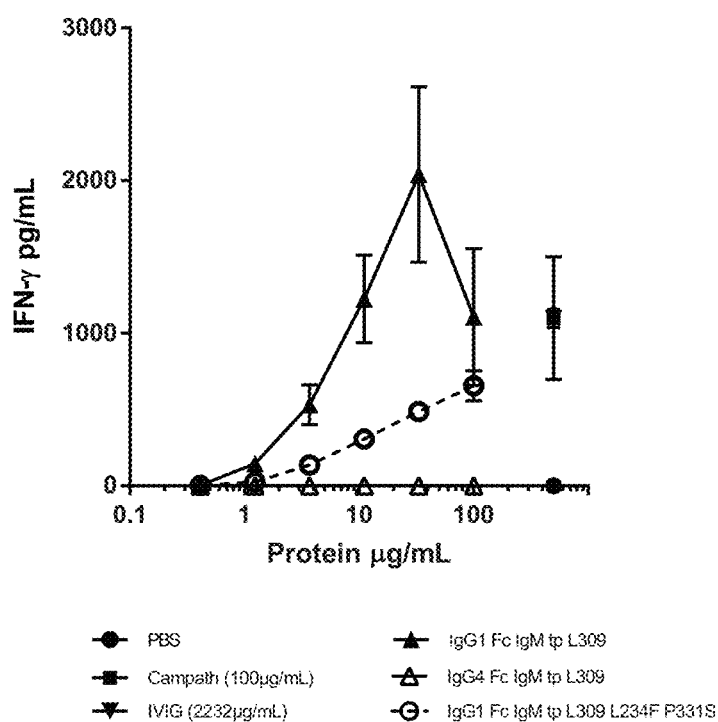
Figure 10:
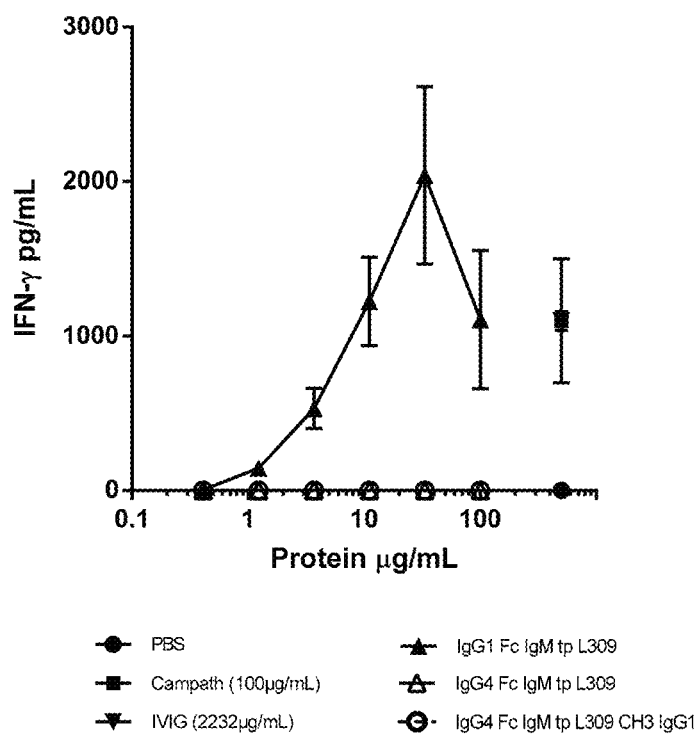
Figure 10:
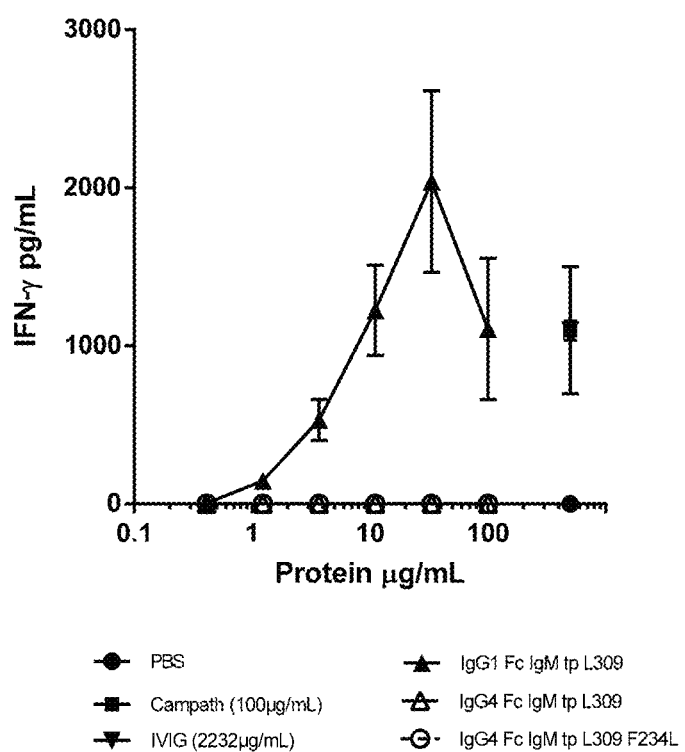
Figure 10:
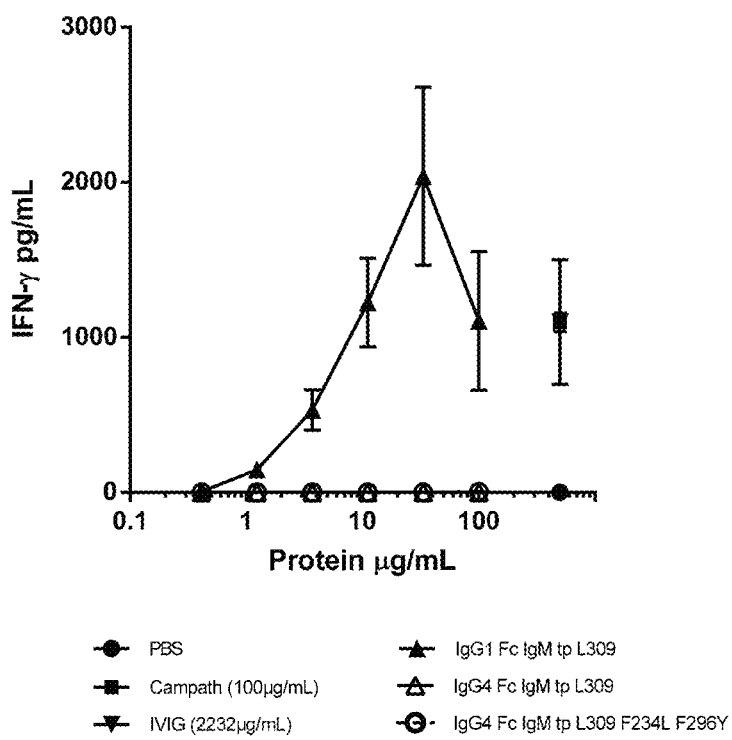
Figure 10:
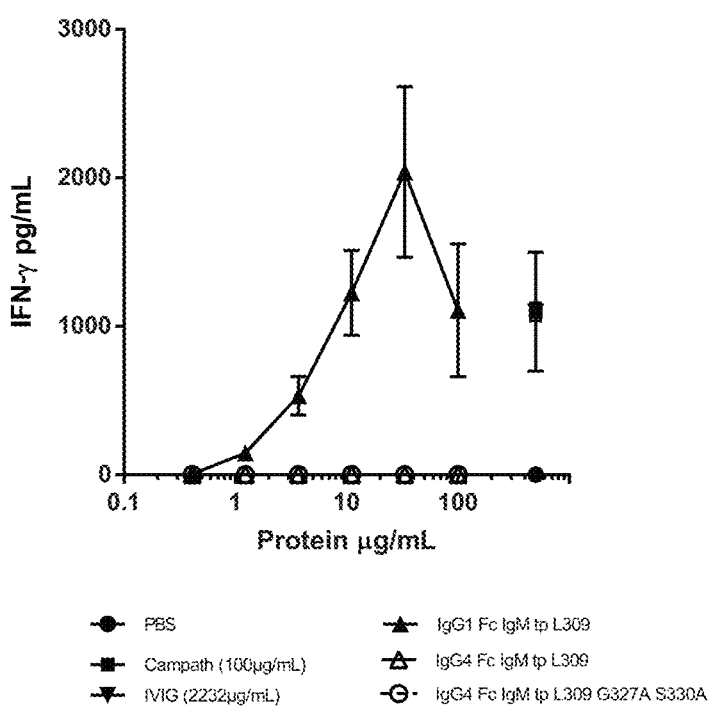
Figure 10:
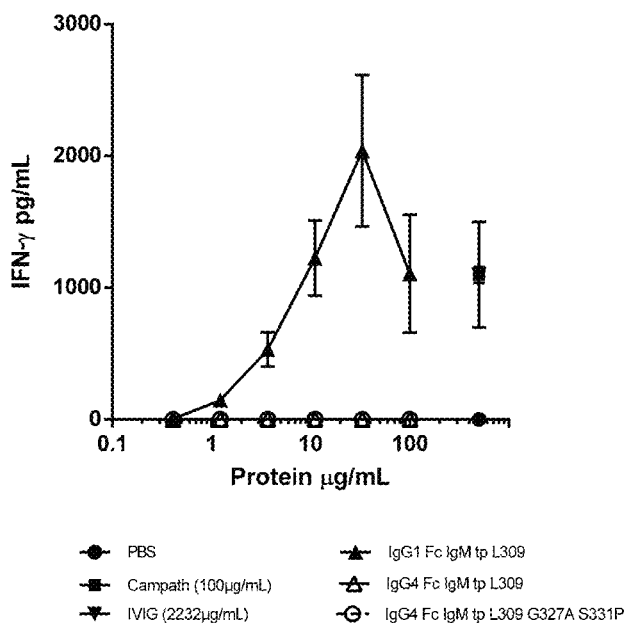
Figure 10:
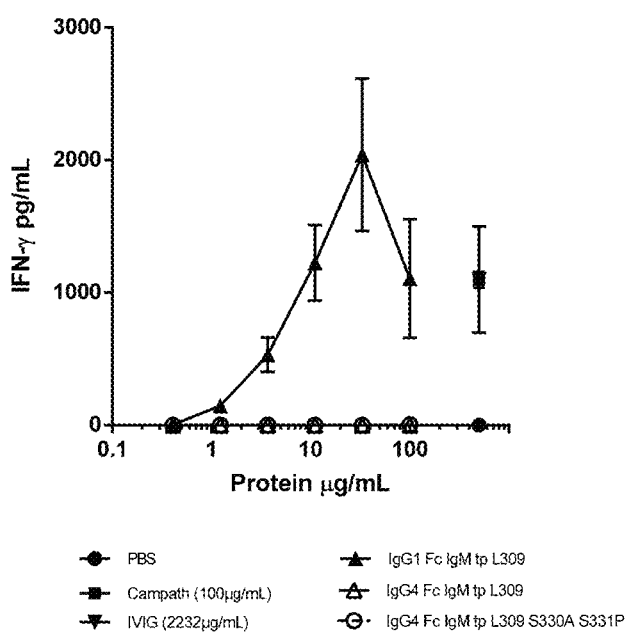

FIG. 10 Stimulation of cytokine release by Fc-multimers. The data show the effects of Fc-multimers engineered with mutations to modulate cytokine release.

Figure 11:
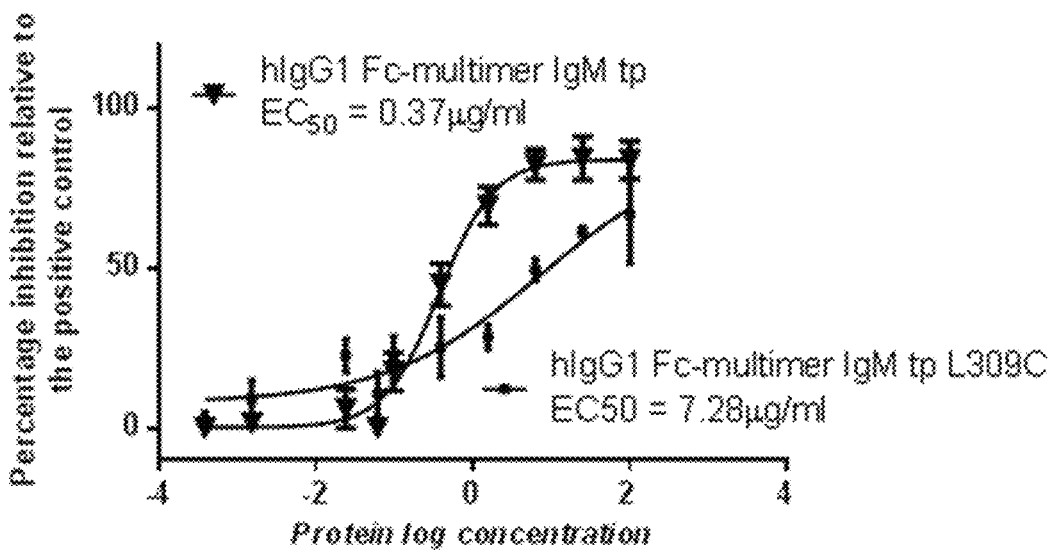
Figure 11:
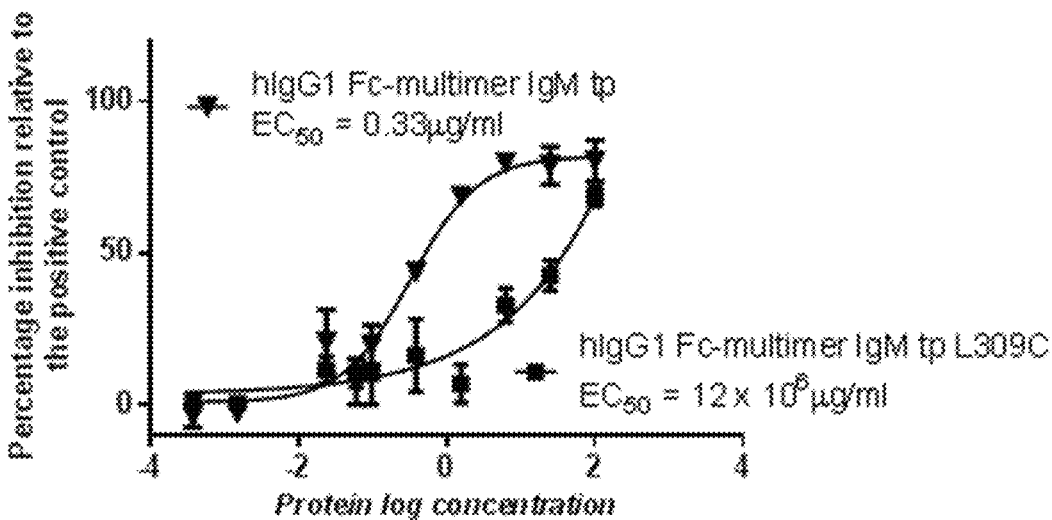

FIG. 11 Inhibition of FcRn-mediated IgG recycling by Fc-multimers.

Figure 12:
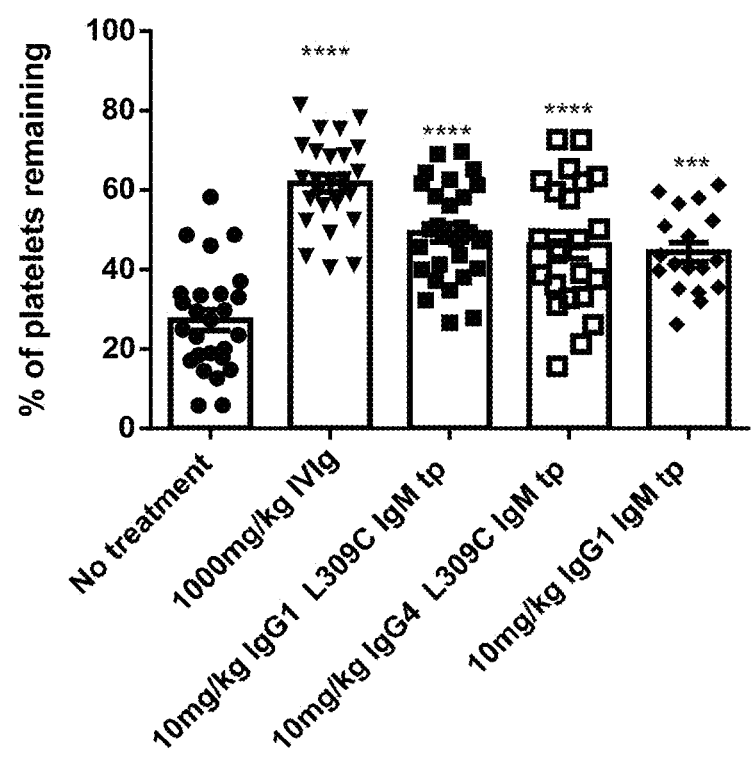

FIG. 12 Prevention of platelet loss in an in vivo model of acute thrombocytopenia by Fc-multimers. The graph shows the aggregated results for five independent experiments using Balb/c mice.

Figure 13:
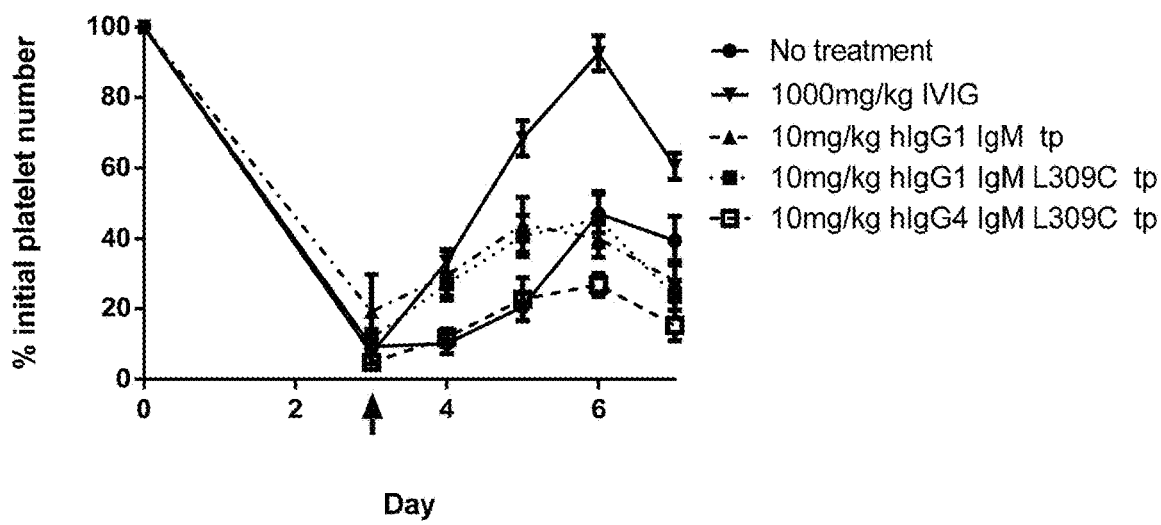
Figure 13:
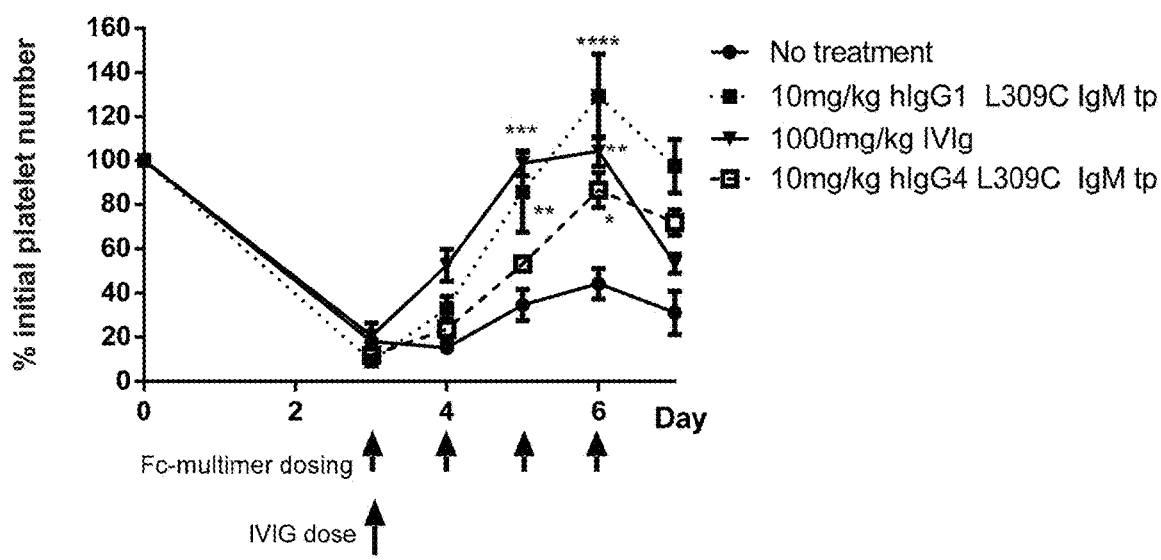

FIG. 13 Prevention of platelet loss in an in vivo model of chronic thrombocytopenia by Fc-multimers.

(a) Single dose of 10 mg/kg Fc-multimer administered on day 3.

(b) Four consecutive daily doses, 10 mg/kg per dose, administered on days 3, 4, 5, and 6.

The group size for each point on the graph was n=6.

Figure 14:
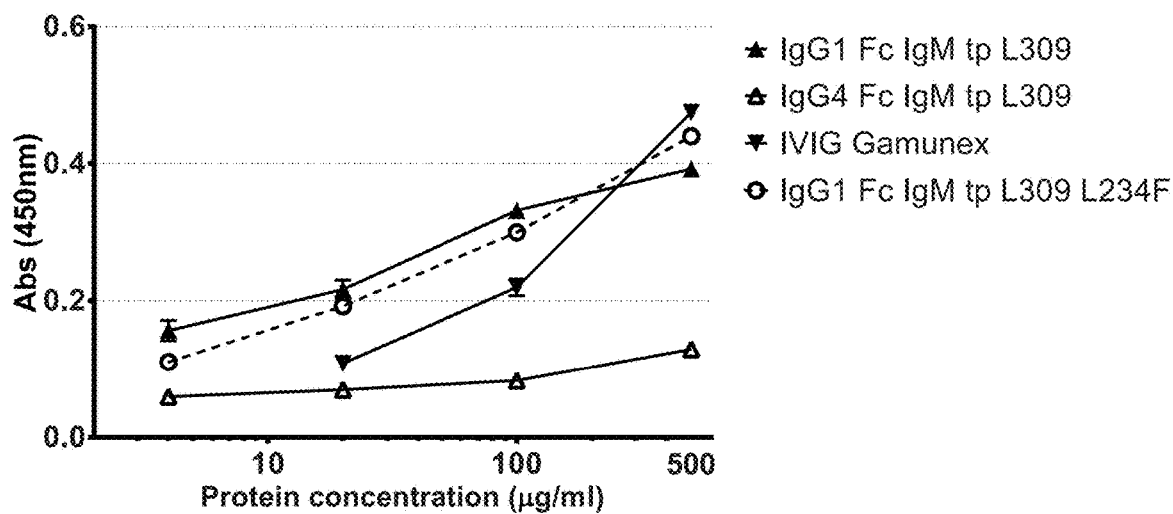
Figure 14:
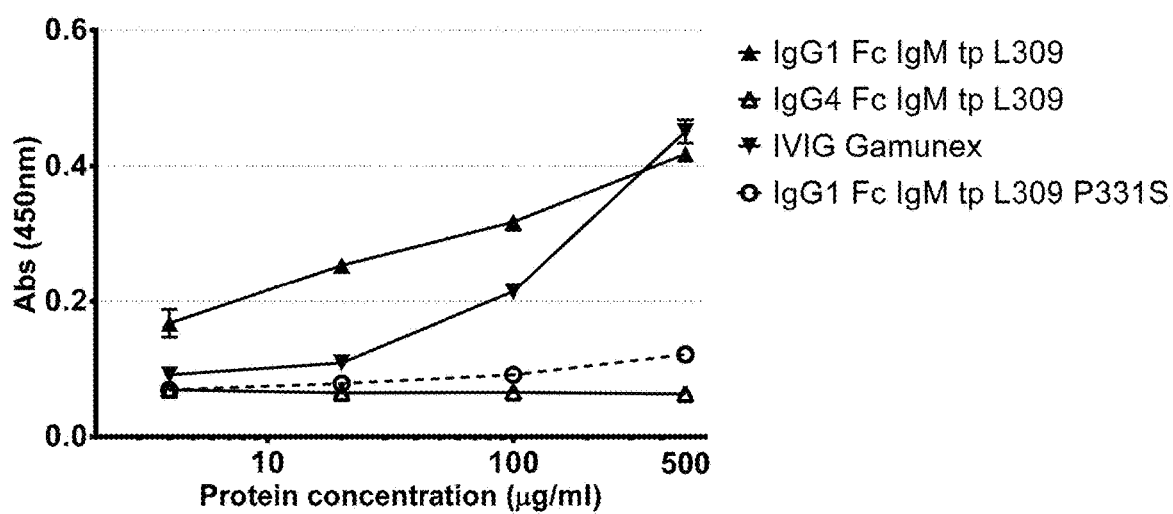
Figure 14:
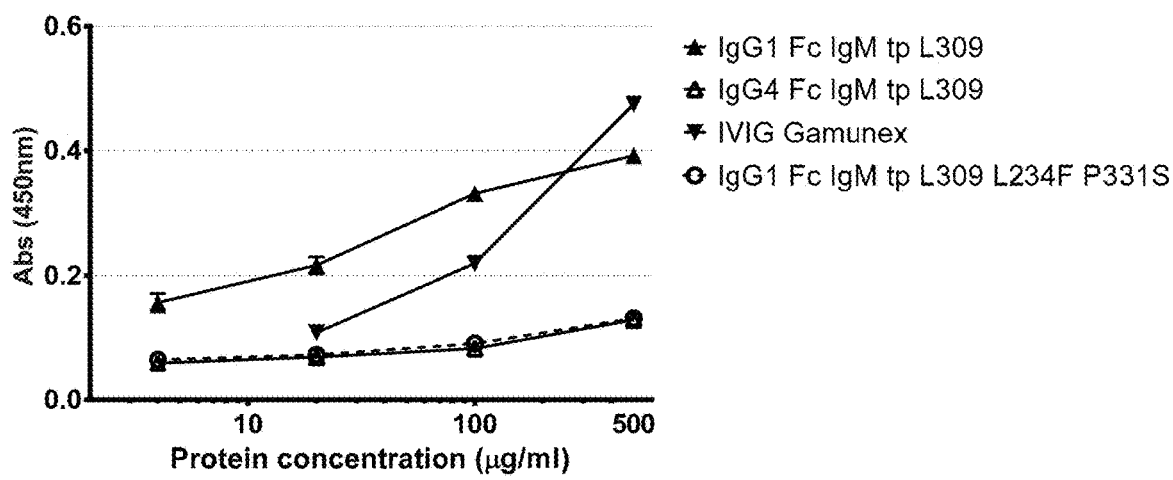
Figure 14:
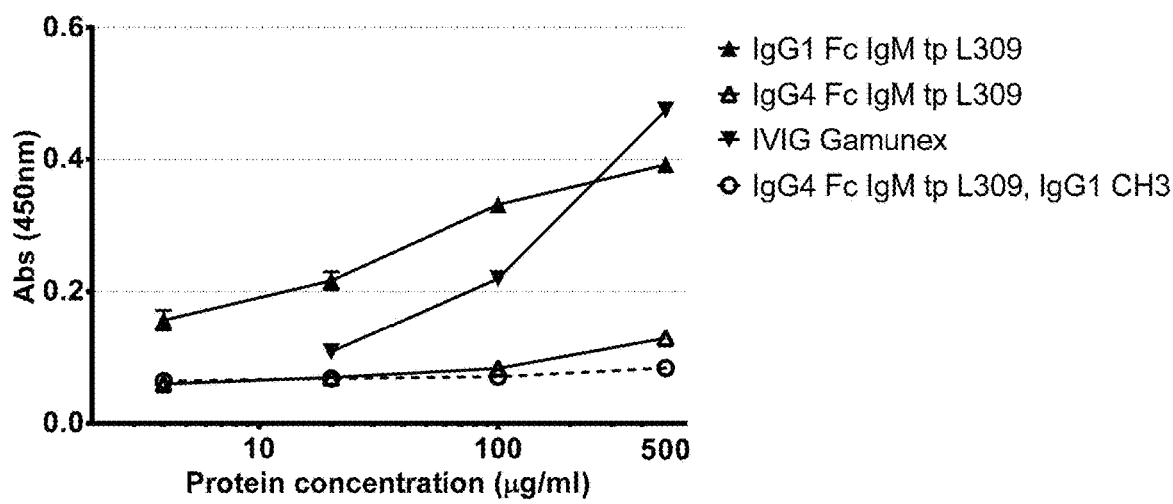
Figure 14:
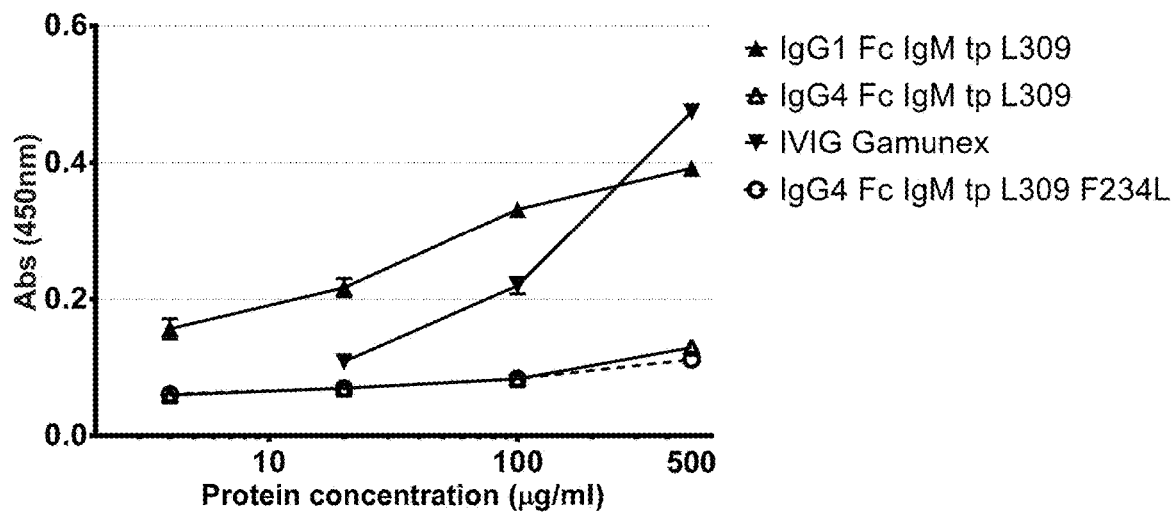
Figure 14:
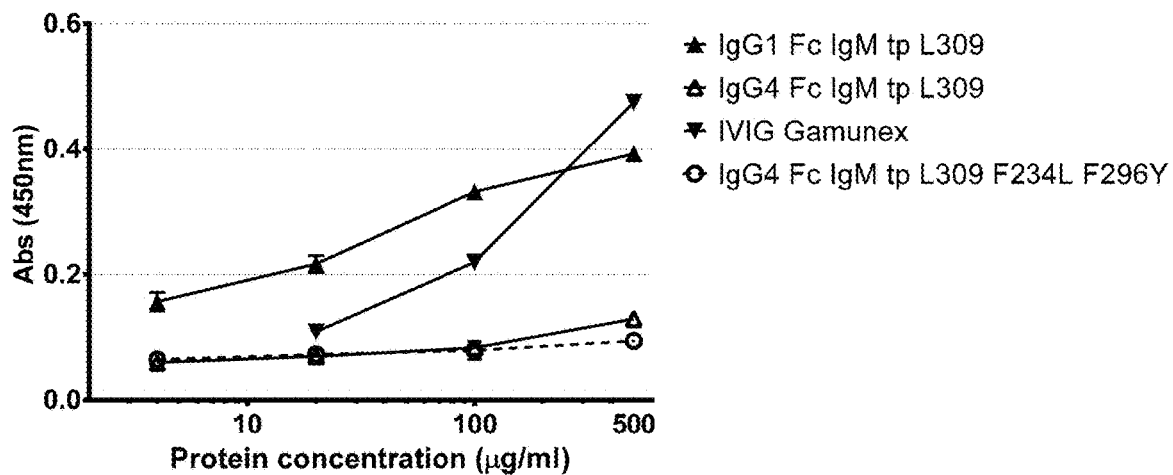
Figure 14:
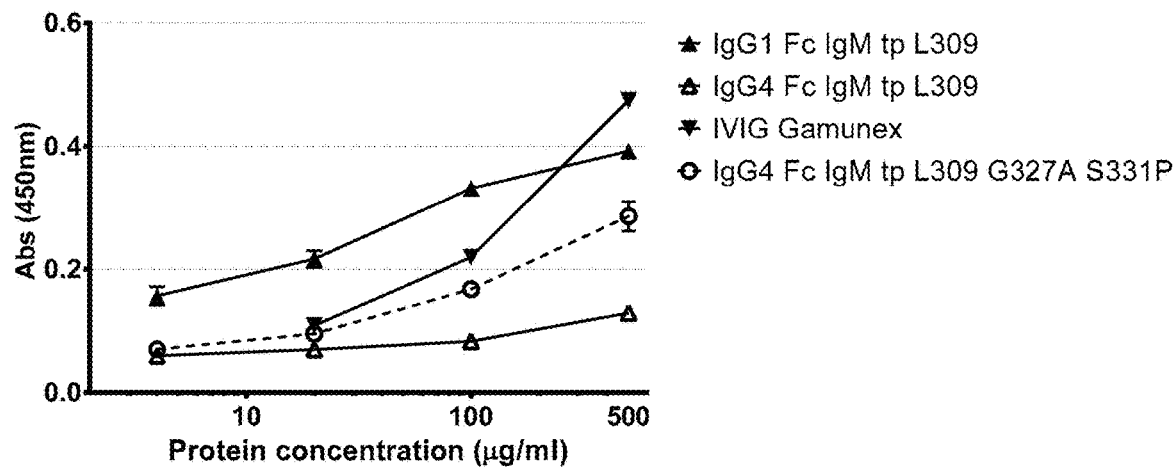
Figure 14:
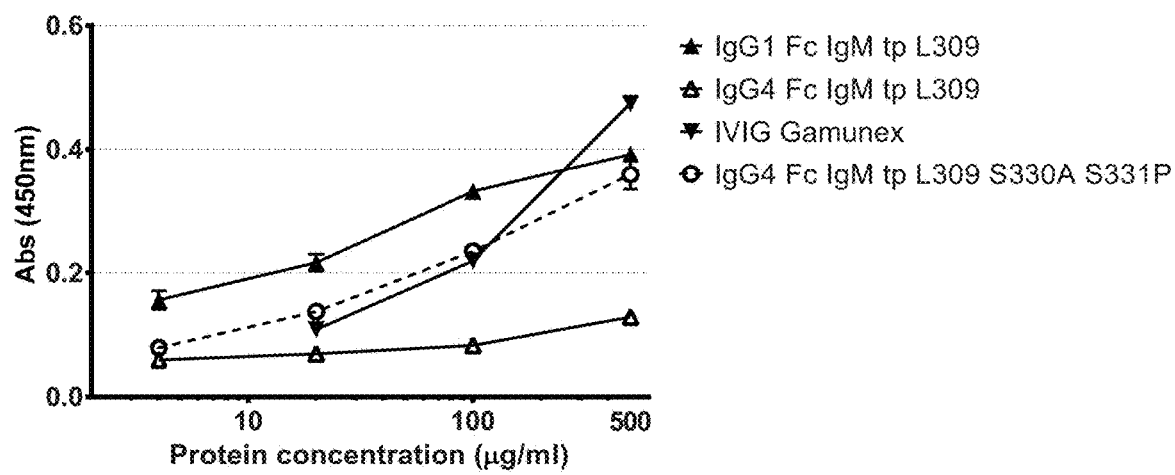
Figure 14:
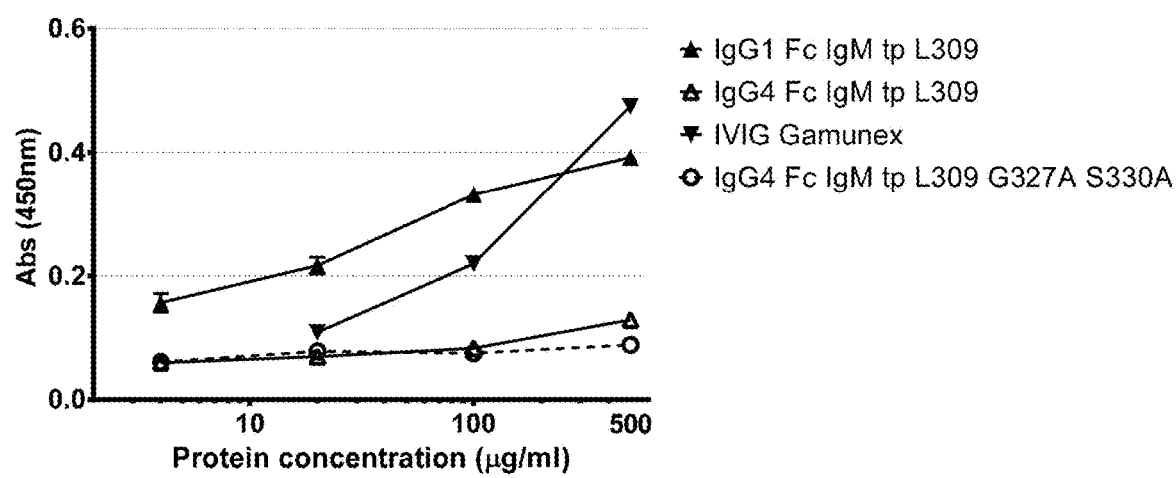

FIG. 14 Binding of Fc-multimers to C1q.

Figure 15:
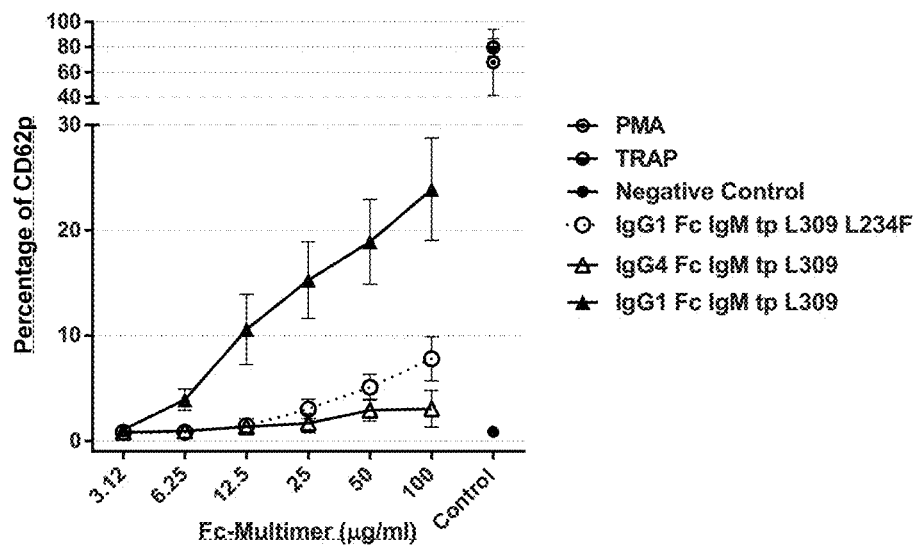
Figure 15:
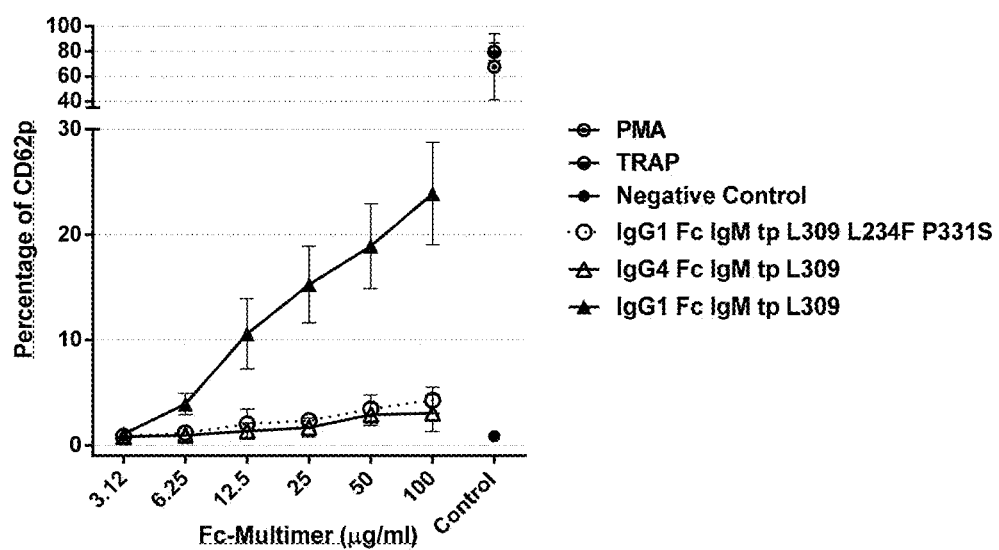
Figure 15:
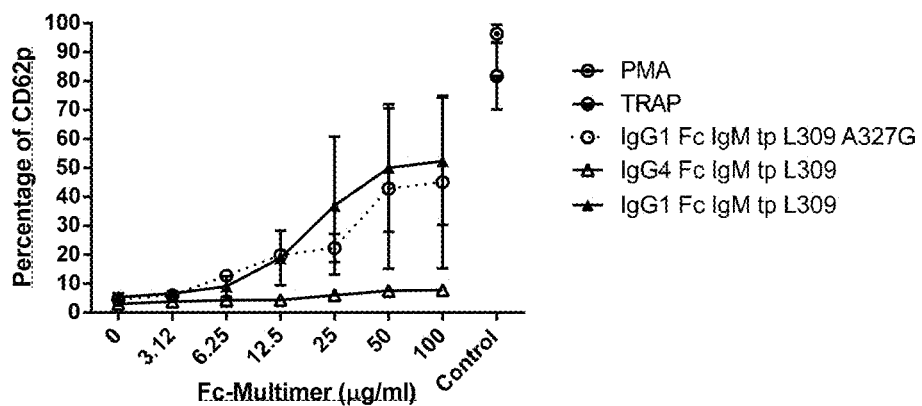
Figure 15:
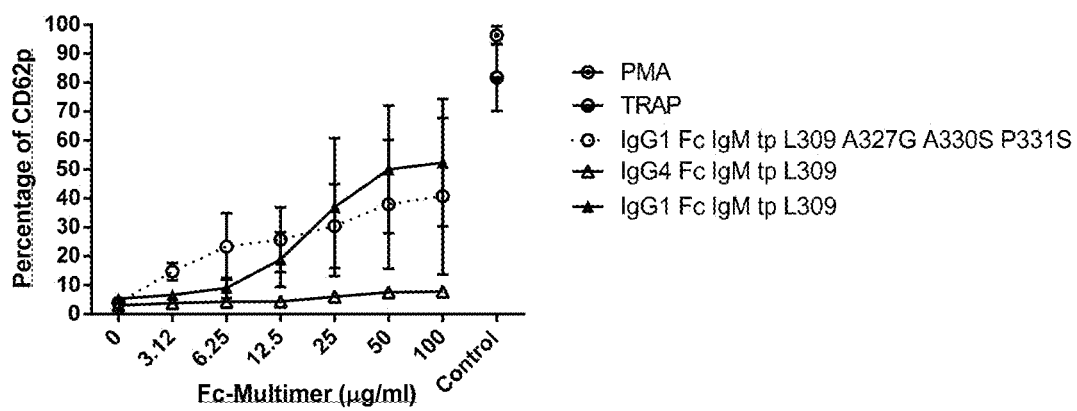
Figure 15:
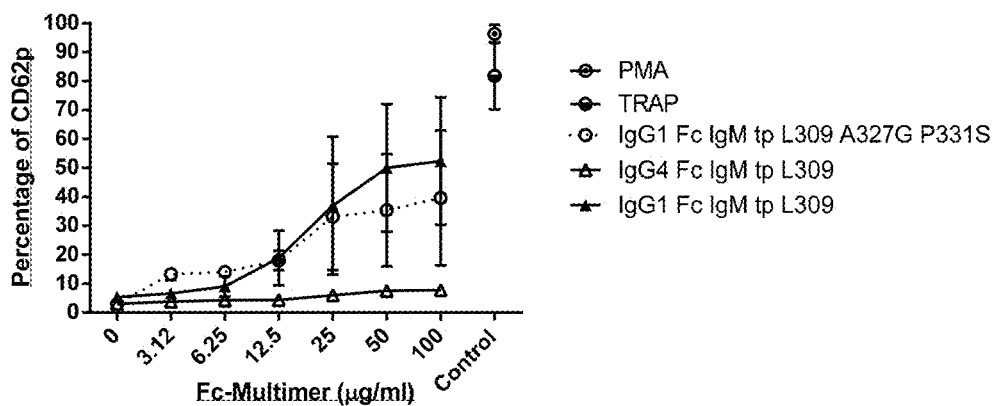
Figure 15:
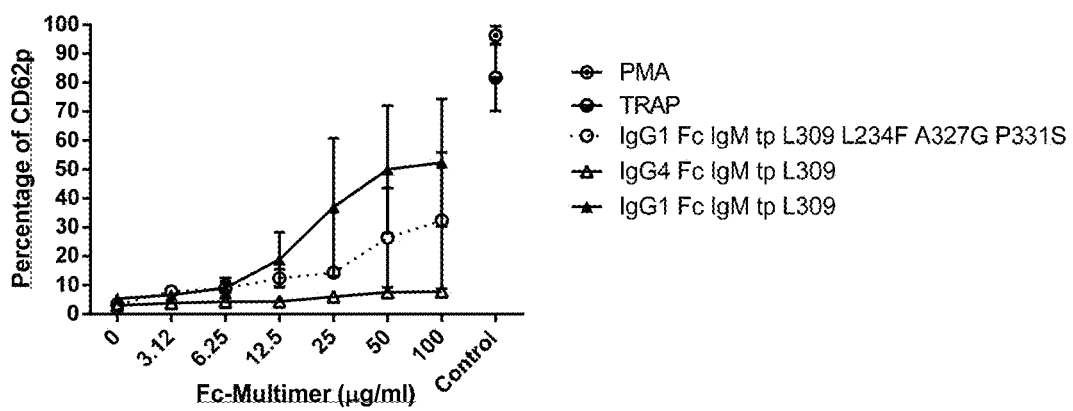
Figure 15:
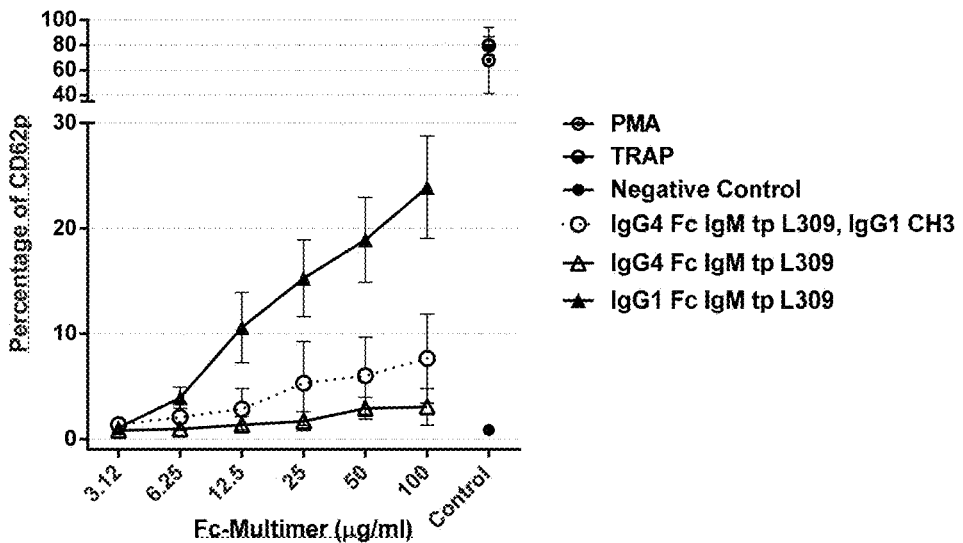
Figure 15:
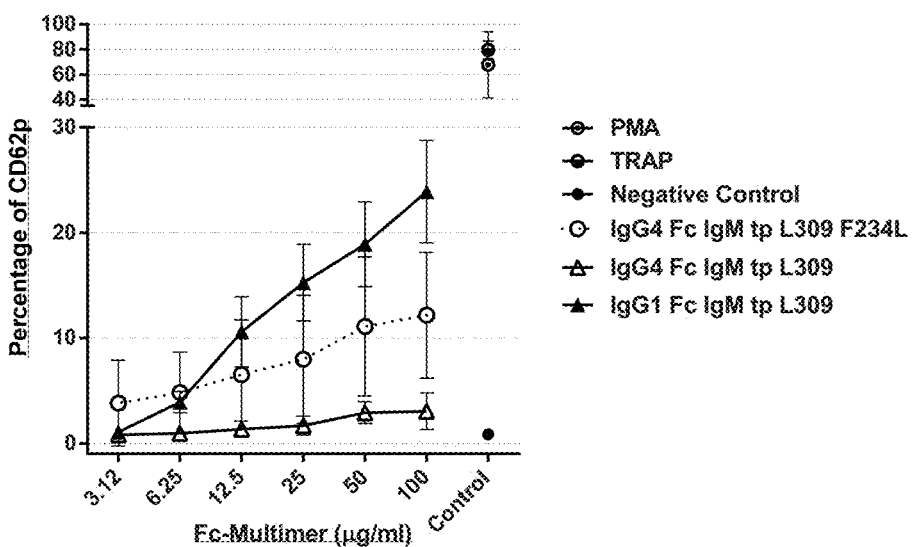
Figure 15:
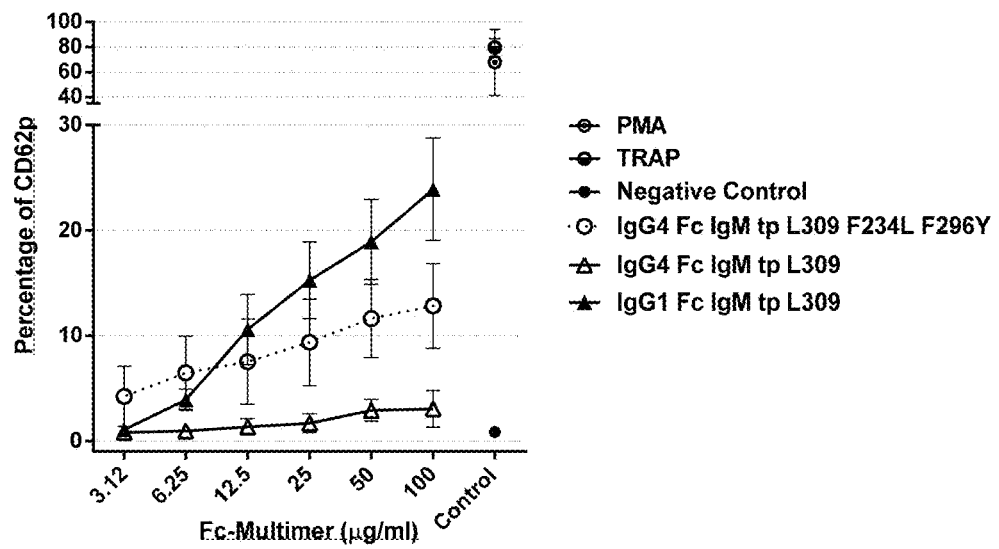
Figure 15:
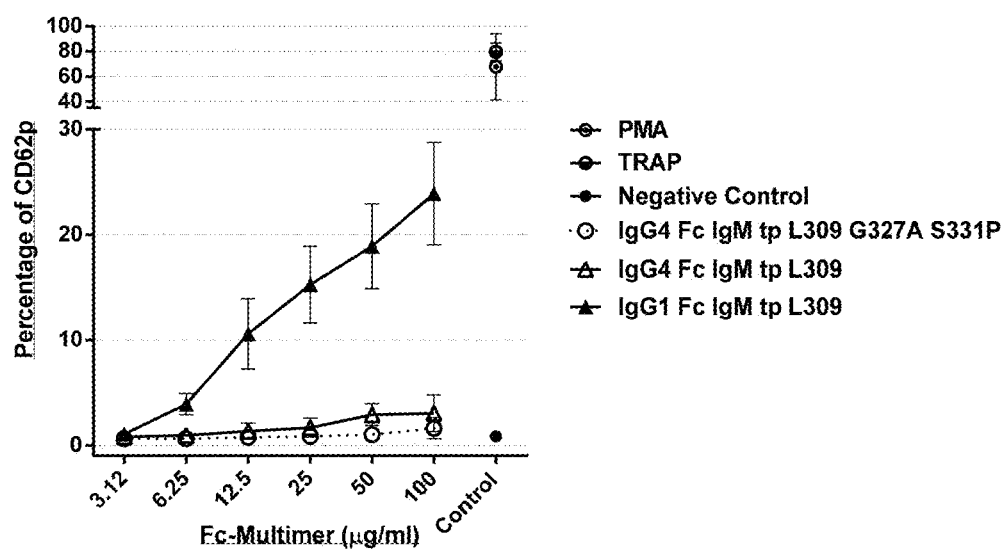
Figure 15:
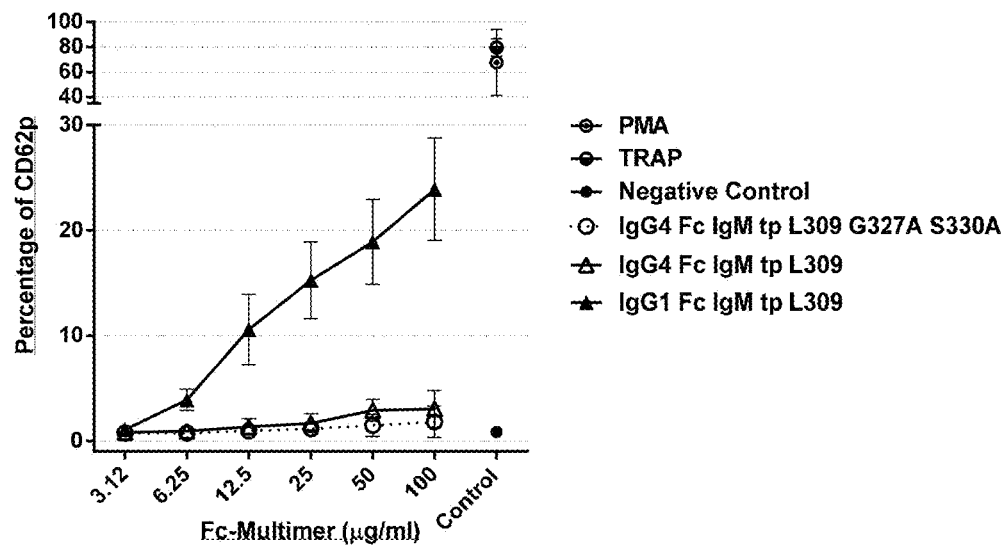
Figure 15:
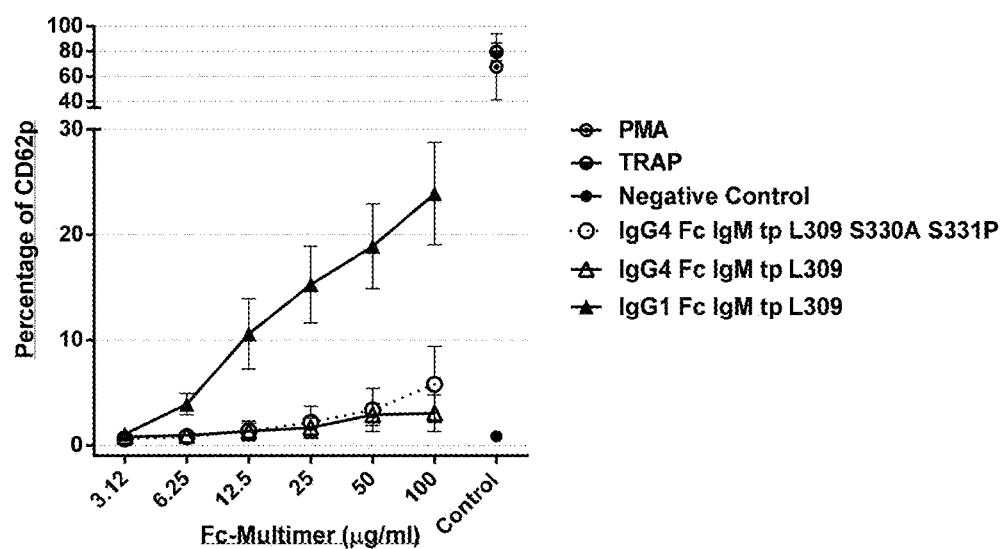

FIG. 15 Platelet activation by Fc-multimers.

EXAMPLES

Example 1: Molecular Biology

Fc-multimer DNA sequences were assembled using standard molecular biology methods, including PCR, restriction-ligation cloning, point mutagenesis (Quikchange) and Sanger sequencing. Expression constructs were cloned into expression plasmids (pNAFL, pNAFH) suitable for both transient and stable expression in CHO cells. Other examples of suitable expression vectors include pCDNA3 (Invitrogen).

A diagram of an expression construct and multimeric fusion protein according to the invention is shown in FIG. 1.

Diagrams showing example amino acid sequences of a polypeptide chain of a polypeptide monomer unit are provided in FIG. 2(a)-(e). In each sequence, the tailpiece sequence is underlined, and any mutations are shown in bold and underlined. In constructs comprising a CH4 domain from IgM, this region is shown in italics.

IgG1/IgG4 Crossover Mutations

Various Fc-multimer variants were constructed in which certain key amino acid residues in the Fc-domain were designed to match those found in IgG1, whilst other key amino acid residues were designed to match those found in IgG4. IgG1 and IgG4 differ from one another at seven positions in the CH2 domain and six positions in the CH3 domain as summarised in Table 4.

TABLE 4

| position number | IgG1 amino acid residue | IgG4 amino acid residue | mutation of IgG1 to IgG4 | mutation of IgG4 to IgG1 |
| --- | --- | --- | --- | --- |
| 234 | L | F | L234F | F234L |
| 268 | H | Q | H268Q | Q268H |
| 274 | K | Q | K274Q | Q274K |
| 296 | Y | F | Y296F | F296Y |
| 327 | A | G | A327G | G327A |
| 330 | A | S | A330S | S330A |
| 331 | P | S | P331S | S331P |
| 355 | R | Q | R355Q | Q355R |
| 356 | D | E | D356E | E356D |
| 358 | L | M | L358M | M358L |
| 409 | K | R | K409R | R409K |
| 419 | Q | E | Q419E | E419Q |
| 445 | P | L | P445L | L445P |

Diagrams showing example amino acid sequences for an Fc-multimer polypeptide chain comprising a CH2 and CH3 domain derived from IgG1 or a CH2 and CH3 domain derived from IgG4 are provided in FIG. 2(b). In each sequence, the positions of difference between IgG1 and IgG4 are in bold and highlighted.

Diagrams showing example amino acid sequences for Fc-multimers designed to combine certain selected properties of IgG1 and certain selected properties of IgG4 are provided in FIG. 2(c). The mutations are shown in bold and underlined.

It will be appreciated that a particular sequence of interest may be created using either the IgG1 or the IgG4 Fc-domain sequence as a starting point and making the relevant mutations. For example, an IgG4 CH2 domain with mutation F234L is the same as an IgG1 CH2 domain with mutations H268Q, K274Q, Y296F, A327G, A330S, and P331S.

Fc-Region Domain Exchange

Fc-multimer variants were also constructed comprising hybrid heavy chain Fc-regions in which the CH2 domain was derived from one particular IgG subclass and the CH3 domain was derived from a different IgG subclass. Diagrams showing example amino acid sequences for Fc-multimers with hybrid heavy chain Fc-regions are provided in FIG. 2(d).

Diagrams showing example amino acid sequences for Fc-multimers with hybrid heavy chain Fc-regions and additional mutations, that have been designed to combine certain selected properties of IgG1 and certain selected properties of IgG4 are provided in FIG. 2(e).

Example 2: Expression

Small scale expression was performed using 'transient' expression of HEK293 or CHO cells transfected using lipofectamine or electroporation. Cultures were grown in shaking flasks or agitated bags in CD-CHO (Lonza) or ProCHO5 (Life Technologies) media at scales ranging from 50-2000 ml for 5-10 days. Cells were removed by centrifugation and culture supernatants were stored at 4° C. until purified. Preservatives were added to some cultures after removal of cells.

The results demonstrated that the multimeric fusion proteins are expressed well.

The signal peptide used to express the multimeric fusion proteins was found to have an impact on the level of expression achieved. A signal peptide from antibody B72.3 resulted in higher expression levels than an IL-2 signal peptide sequence described in the prior art.

The DNA and amino acid sequences of the B72.3 signal peptide are shown in FIG. 2f.

Example 3: Purification and Analysis

Fc-multimers were purified from culture supernatants after checking/adjusting pH to be ≥6.5, by protein A chromatography with step elution using a pH3.4 buffer. Eluate was immediately neutralised to ~pH7.0 using 1M Tris pH8.5 before storage at 4° C. Analytical size exclusion chromatography was used to separate various multimeric forms of Fc-domains using S200 columns and fraction collection. Fractions were analysed and pooled after G3000 HPLC and reducing and non-reducing SDS-PAGE analysis. Endotoxin was tested using the limulus amoebocyte lysate (LAL) assay and samples used in assays were <1 EU/mg.

The multimeric fusion proteins were found to be expressed and purified predominantly in hexameric form, with some protein in dodecameric and other forms. The results demonstrate that the proteins assemble effectively into multimers in the absence of cysteine at position 309.

Purification of the multimeric fusion proteins in the presence of a preservative reduced the tendency to aggregate, producing improved preparations with more uniform structure. Examples of preservatives shown to be effective include thiol capping agents such as N-ethylmaleimide (NEM) and glutathione (GSH); and disulphide inhibiting agents such as ethylenediaminetetraacetic acid (EDTA).

Example 4: Role of the CH3 Domain in Fc-Multimer Assembly

Figure 3A:
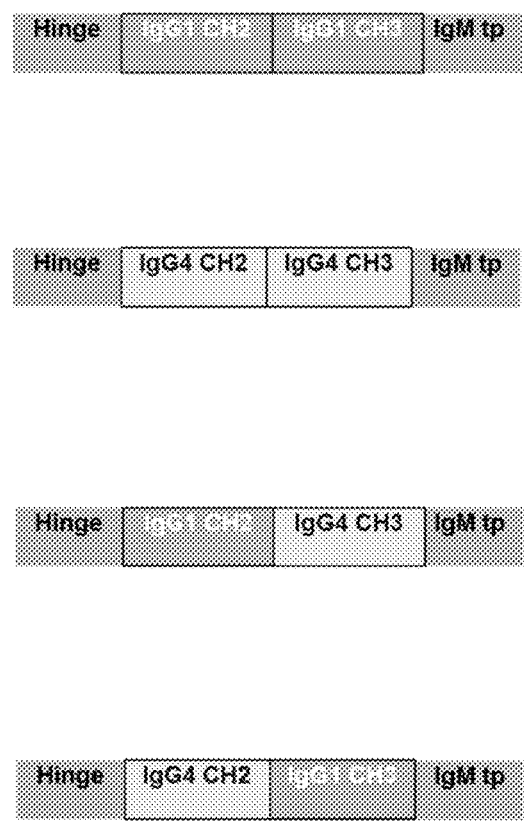
Figure 3A:
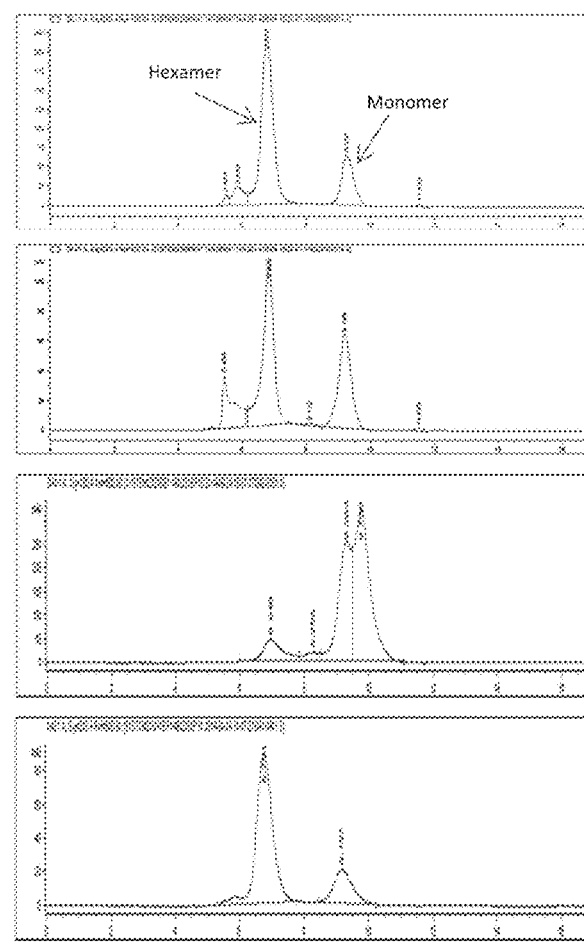

The extent of multimerisation was unexpectedly found to vary depending on the IgG subclass from which the Fc-region was derived. Fc-multimers comprising a CH2 domain and a CH3 domain derived from IgG1 assembled very efficiently into hexamers, with approximately 80% of the molecules being present in hexameric form. In contrast, Fc-multimers comprising a CH2 domain and a CH3 domain derived from IgG4 formed lower levels of hexamers. Investigation of Fc-multimers comprising hybrid Fc-regions in which the CH2 domain was derived from one particular IgG subclass and the CH3 domain was derived from a different IgG subclass revealed that the ability to form hexamers is encoded mainly by the CH3 domain. The presence of a CH3 domain derived from IgG1 significantly increases hexamerisation. Hybrid Fc-multimers in which the CH3 domain is derived from IgG1 and the CH2 domain is derived from IgG4 hexamerised just as efficiently as IgG1 wild-type, with approximately 80% of the molecules being found as hexamers. Thus, replacing the CH3 domain of IgG4 with that of IgG1 improves the levels of hexamerisation compared to wild type IgG4 Fc-multimers. The resulting hybrid has the advantage of high levels of hexamer formation whilst retaining many of the desirable properties of IgG4. FIG. 3(a).

Figure 3B:
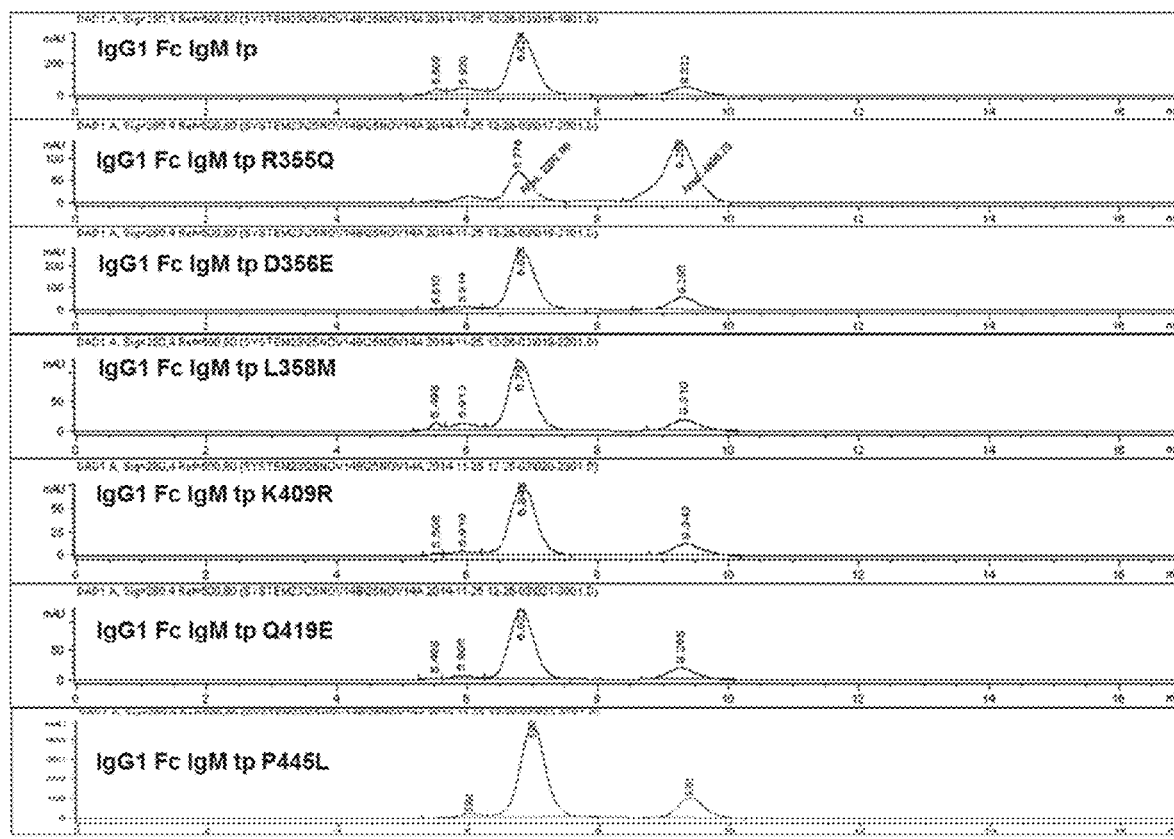

The CH3 domains of IgG1 and IgG4 differ at six positions as described in Example 1. Starting with an Fc-multimer comprising a CH2 and CH3 domain derived from IgG1, each of these positions was mutated in turn, from the IgG1 residue to the IgG4 residue. The results demonstrated that the amino acid at position 355 is critical for hexamerisation. The amino acid found at position 355 in wild type IgG1, arginine, promotes efficient hexamerisation. That found in wild type IgG4, glutamine, results in lower hexamerisation. The other positions of difference between the IgG1 and IgG4 CH3 domains did not affect hexamerisation. FIG. 3(b).

Figure 3C:
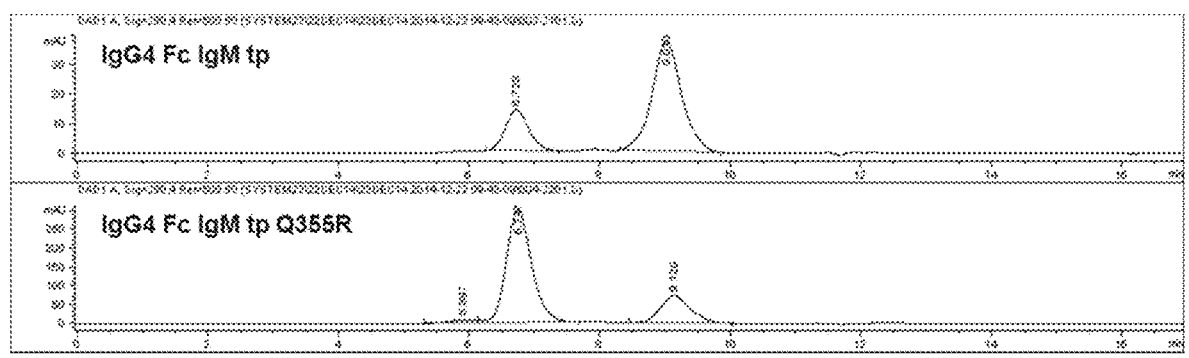

In Fc-multimers comprising a CH3 domain derived from IgG4, substitution of the glutamine residue at position 355 with an arginine residue (Q355R) resulted in high levels of hexamerisation. Thus, the problem of lower hexamerisation of IgG4 Fc-multimers can be solved by a single amino acid substitution. This has the advantage that the resulting Fc-multimer assembles into hexamers with high efficiency whilst retaining the characteristic properties of IgG4. FIG. 3(c).

Figure 3D:
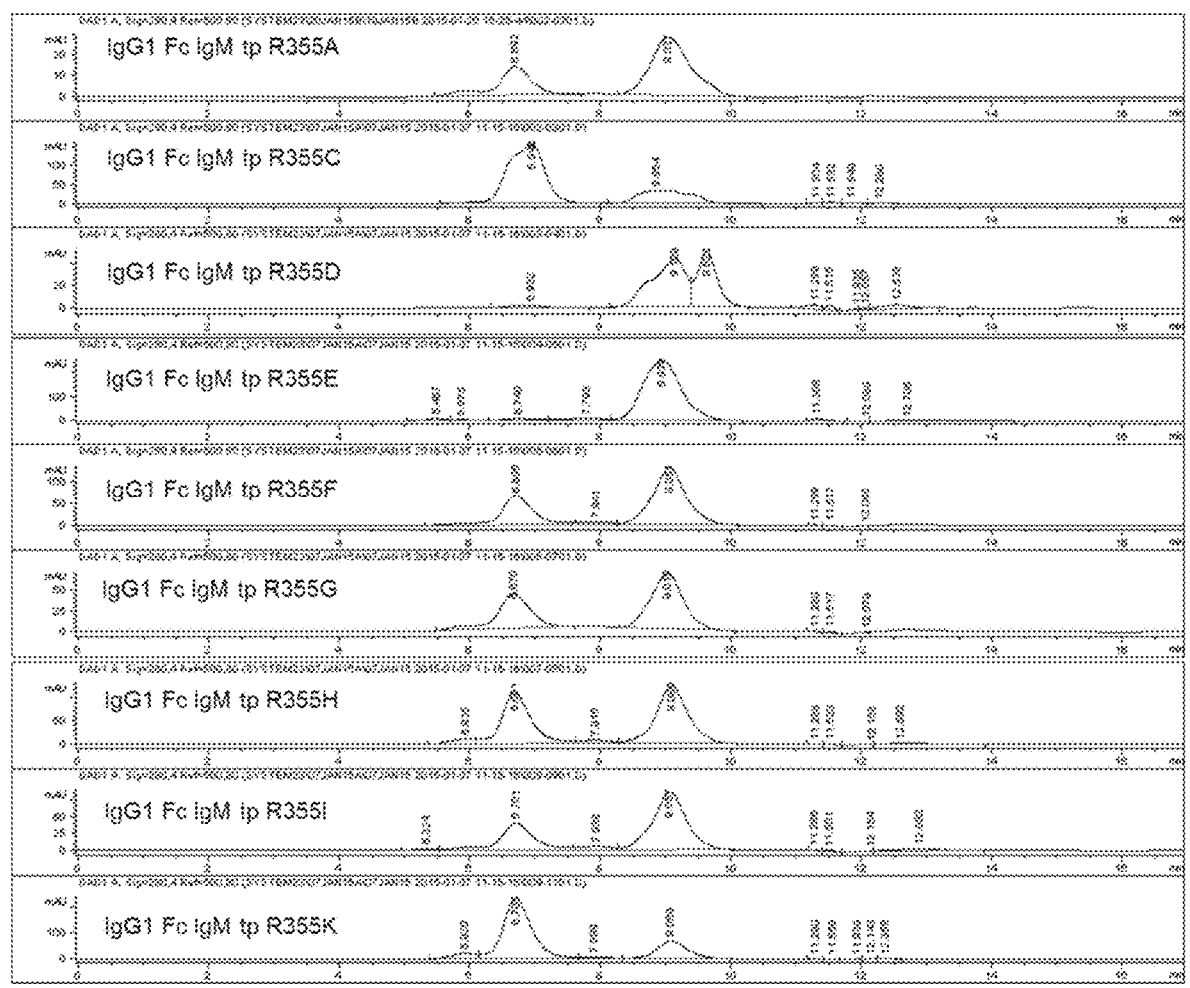
Figure 3D:
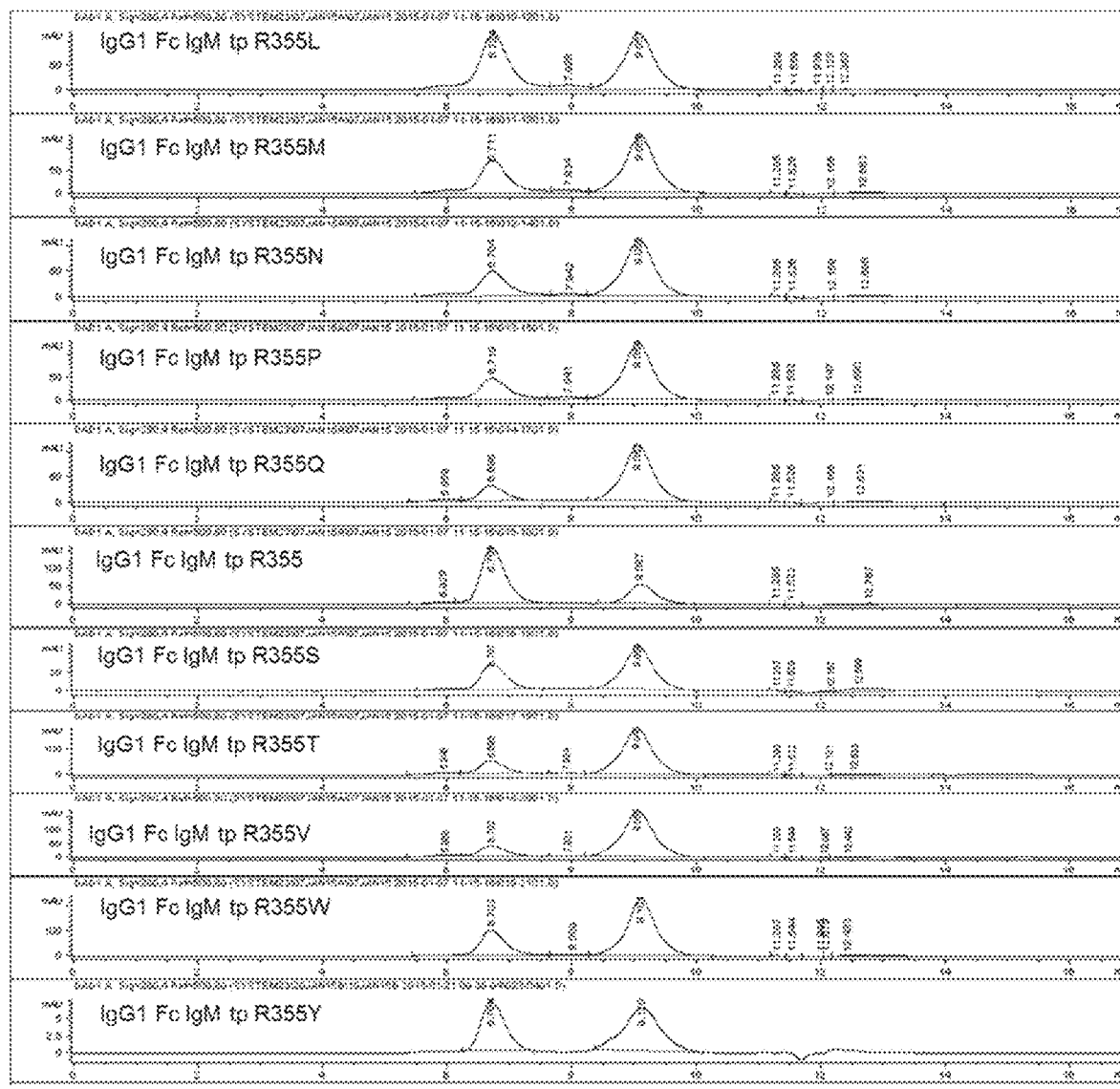

In IgG1 Fc multimers, substitution of arginine at position 355 with cysteine (R355C) increased hexamer formation beyond that of wild type IgG1. Although we do not wish to be bound by theory, this result suggests that a cysteine residue at position 355 may be capable of forming disulphide bonds with the cysteine in the tailpiece. Mutagenesis of R355 to all the other amino acids did not result in further enhancement of hexamer formation in IgG1 Fc-multimers. FIG. 3(d).

Example 5: Affinity Measurements for Interactions of Fc-Multimers and FcR

Affinity/avidity measurements for the interactions of multimeric fusion proteins and Fc receptors (FcR) including FcγR and FcRn can be performed using well known methods including surface plasmon resonance, competition ELISA and competition binding studies on FcR bearing cell lines. Soluble, extra-cellular domains (ECDs) of FcRs were used in surface plasmon resonance experiments by non-specific immobilisation or tag specific capture onto a BIAcore sensor chip on a Biacore T200. Human FcRn extracellular domain was provided as a non-covalent complex between the human FcRn alpha chain extracellular domain and β2 microglobulin. Multimeric fusion proteins were titrated over the receptors at a variety of concentrations and flow rates in order to best determine the strength of the interaction. Data was analysed using Biacore T200 Evaluation software.

FIG. 4 shows data for binding of multimeric fusion proteins to FcRn, measured by surface plasmon resonance analysis. The traces demonstrate binding for multimer concentration range: 2.5 µM, 1.25 µM, 0.625 µM, 0.3125 µM, 0.15625 µM, 0.078125 µM, 0.0390625 µM. The Fc-multimers shown all comprised histidine at position 310.

(a) human IgG1 Fc-multimer IgM tp L309C binding to low density FcRn.

(b) human IgG1 Fc-multimer IgM tp binding to low density FcRn.

(c) human IgG1 Fc-multimer IgM tp L309C binding to high density FcRn.

(d) human IgG1 Fc-multimer IgM tp binding to high density FcRn.

Constructs used in (a) and (c) contain a leucine to cysteine substitution at position 309.

The results demonstrated that Fc-multimers comprising histidine at position 310 bind to human FcRn.

A number of Fc-multimers were also generated which incorporated mutations thought to increase binding to human FcRn.

Table 5 shows the dissociation constants for the binding of mutated monomeric human IgG1 Fc fragments to human FcRn at pH6.0. The mutations resulted in increased binding to human FcRn. However, the strength of the interaction of the monomeric fragments is still weak, with dissociation constants in the micromolar range. Multimerisation of the mutated Fc-domains, as described in the present invention, may confer an avidity benefit, so greatly improving the strength of the interaction.

TABLE 5

Binding of mutated monomeric IgG1 Fc-fragments to human FcRn at pH 6.0

| Sample mutation | KD (M) | KD (µM) |
| --- | --- | --- |
| IgG1 Fc, WT | 9.78E−07 | 0.98 |
| IgG1 Fc, L309S | 1.25E−06 | 1.25 |
| IgG1 Fc, Q311A | 7.69E−07 | 0.77 |
| IgG1 Fc, T307A | 5.65E−07 | 0.57 |
| IgG1 Fc, T307P | 6.93E−07 | 0.69 |
| IgG1 Fc, V308C | 7.00E−07 | 0.70 |
| IgG1 Fc, V308F | 3.32E−07 | 0.33 |
| IgG1 Fc, V308P | 1.36E−07 | 0.14 |
| IgG1 Fc, WT | 1.07E−06 | 1.07 |

Example 6: Macrophage Phagocytosis of B Cell Targets

An assay was designed to measure antibody-dependent phagocytosis of B cells by human macrophages. To prepare macrophages, human peripheral blood mononuclear cells (PBMC) were first isolated from fresh blood by density-gradient centrifugation. Monocytes were then selected by incubating the PBMCs for 1 hour at 37° C. in 6-well tissue culture coated plates, followed by removal of non-adherent cells. Adherent monocytes were differentiated into macrophages by 5 day culture in macrophage-colony stimulating factor (MCSF). Human B cells were then prepared from a separate (allogeneic) donor by isolation of PBMC followed by purification of B cells by negative selection using MACS (B cell isolation kit II, Miltenyi Biotech). In some assays, B cells were labelled with carboxyfluorescein succinimidyl ester (CFSE) (Molecular Probes). Differentiated macrophages and B cells were co-cultured at a 1:5 ratio in the presence of anti-CD20 mAb (rituximab) to induce antibody-dependent phagocytosis of the B cells. Multimeric fusion proteins or controls were added at the indicated concentrations and the cells incubated at 37° C. 5% $CO_2$ for 1-24 hrs. At the end of each time-point, cells were centrifuged and resuspended in FACS buffer at 4° C. to stop further phagocytosis and the B cells surface-stained with anti-CD19 allophycocyanin (APC) before analysis by flow cytometry. Macrophages were distinguished by their auto-fluorescence/side-scatter properties and B cells by their CFSE/CD19 labelling. CFSE-positive macrophages negative for CD19 labelling were assumed to contain engulfed B cells.

The results demonstrated that the multimeric fusion proteins of the invention inhibit B cell depletion by human macrophages. (FIG. 5). The data show that Fc-multimers derived from human IgG1 or IgG4, polymerised into hexamer or dodecamer forms by IgM tailpiece alone, or IgM tailpiece and L309C, all exhibit potency and maximum levels of inhibition significantly better than human IVIG.

The demonstration that the dodecamer form and hexamer form are equally potent is of benefit for product manufacturing and safety, as there is no need for additional purification to remove trace amounts of dodecamer from hexamer.

Flow cytometry analysis using CFSE stained B-cells confirmed that the mechanism of action is inhibition of macrophage phagocytosis, and not B-cell killing or apoptosis by other means.

In order to assess the ability of any given Fc-multimer construct to inhibit macrophage phagocytosis, its activity was measured in the assay described herein above and compared with the activities of IgG1 and IgG4 wild type Fc-multimers. The activity of each mutant was then summarised as "IgG1-like", "high", "medium", "low", or "IgG4-like", based on a visual comparison of its concentration vs. effect curve with those obtained for IgG1 and IgG4 wild type Fc-multimers.

Results for Fc-multimers comprising single cross-over mutations at each of the eight positions of difference in the IgG1 and IgG4 Fc region are shown in FIG. 6 and summarised in Table 6.

Wild type IgG1 Fc-multimer, comprising a CH2 and a CH3 domain derived from IgG1, potently inhibits macrophage phagocytosis of antibody-coated target cells. Two of the single mutations in IgG1 Fc multimers (A330S, K409R) have no effect on the potency of inhibition of phagocytosis. Six of the single mutations (L234F, H268Q, K274Q, Y296F, A327G and P331S) result in a modest reduction in the potency of inhibition of phagocytosis. The residues L234F and A327G are of particular interest as mutating these significantly reduces cytokine release (see Example 8), whilst maintaining relatively high potency in inhibition of phagocytosis. This combination of properties will be useful for the treatment of autoimmune disorders.

Wild type IgG4 Fc-multimers inhibit macrophage phagocytosis of antibody-coated target cells, but less potently than IgG1 Fc-multimers. Two of the single mutations in IgG4 Fc-multimers (F234L and G327A) modestly increase the potency of inhibition of phagocytosis. Six of the mutations in IgG4 (Q268H, Q274K, F296Y, S330A, S331P, R409K) have no effect on inhibition of phagocytosis when mutated individually. The residues F234L and G327A are of particular interest as, whilst individually mutating either of these positions enhances potency of IgG4 Fc multimers in inhibition of phagocytosis, they have no effect on increasing cytokine production (see Example 8). This combination of properties will be useful for the treatment of autoimmune disorders.

TABLE 6

| Fc-multimer | potency of phagocytosis inhibition |
|---|---|
| IgG1 Fc IgM tp L309 | the standard for "IgG1-like" |
| IgG1 Fc IgM tp L309 L234F | high |
| IgG1 Fc IgM tp L309 H268Q | high |
| IgG1 Fc IgM tp L309 K274Q | high |
| IgG1 Fc IgM tp L309 Y296F | high |
| IgG1 Fc IgM tp L309 A327G | high |
| IgG1 Fc IgM tp L309 A330S | IgG1-like |
| IgG1 Fc IgM tp L309 P331S | high |
| IgG1 Fc IgM tp L309 K409R | IgG1-like |
| IgG4 Fc IgM tp L309 | the standard for "IgG4-like" |
| IgG4 Fc IgM tp L309 F234L | medium |
| IgG4 Fc IgM tp L309 Q268H | IgG4-like |
| IgG4 Fc IgM tp L309 Q274K | IgG4-like |
| IgG4 Fc IgM tp L309 F296Y | IgG4-like |
| IgG4 Fc IgM tp L309 G327A | low |
| IgG4 Fc IgM tp L309 S330A | IgG4-like |
| IgG4 Fc IgM tp L309 S331P | IgG4-like |
| IgG4 Fc IgM tp L309 R409K | IgG4-like |

Results for further Fc-multimer constructs designed for use in the treatment of immune disorders are shown in FIG. 7 and summarised in Table 7.

Wild type IgG1 and IgG4 Fc-multimers inhibit macrophage phagocytosis of antibody-coated target cells more potently than IVIG.

IgG1 Fc-multimers comprising L234F (which reduces cytokine production) or L234F and P331S (reduces cytokine production and C1Q binding, see Examples 8 and 15) have modestly reduced potency in inhibition of phagocytosis relative to wild type IgG1 Fc-multimers, but are still highly potent relative to wild type IgG4 Fc-multimers or IVIG.

IgG4 Fc-multimers comprising the mutations F234L; F234L and F296Y; G327A and S331P; S330A and S331P; or G327A and S330A; have enhanced potency in inhibition of phagocytosis compared to wild type IgG4 Fc-multimers.

TABLE 7

| Fc-multimer | potency of phagocytosis inhibition |
|---|---|
| IgG1 Fc IgM tp L309 | the standard for "IgG1-like" |
| IgG4 Fc IgM tp L309 | the standard for "IgG4-like" |
| IgG1 Fc IgM tp L309 L234F | high |
| IgG1 Fc IgM tp L309 L234F P331S | high |
| Hybrid Fc IgG4-CH2 IgG1-CH3 IgM tp L309 | medium |
| IgG4 Fc IgM tp L309 F234L | medium |
| IgG4 Fc IgM tp L309 F234L F296Y | medium |
| IgG4 Fc IgM tp L309 G327A S330A | medium |
| IgG4 Fc IgM tp L309 G327A S331P | medium |
| IgG4 Fc IgM tp L309 S330A S331P | medium |

Example 7: THP1 Cell Phagocytosis of IgG FITC Beads

THP1 cells were plated out at passage 7, counted and re-suspended at 5×10$^5$ cells/ml. 200 µl of cells were added to each well of a 96-well flat bottom plate (1×10$^5$ cells per well). Beads coated with rabbit IgG (Cambridge bioscience CAY500290-1 ea) were added directly to each well, mixed (1 in 10 dilution, 10 µl/well) and left for the time points: 1 h, 2 h, 4 h, 8 h. Zero time points were effected by adding beads to cells in ice cold buffer on ice. At the end of each time point, cells were centrifuged at 300 g for 3 mins. The cells were resuspended in FACS buffer containing a 1:20 dilution of trypan blue stock solution for 2 minutes. Cells were washed with 150 µl FACS buffer, centrifuged and resuspended in 200 µl FACS buffer and transferred to a round bottom plate ready for FACS. Cells were centrifuged once more and resuspended in 200 µl of FACS buffer before analysis by flow cytometry. THP1 cells were gated on forward and side-scatter and uptake of beads measured as FITC fluorescence.

Example 8: Human Whole Blood Cytokine Release Assay

Fresh blood was collected from donors in lithium heparin vacutainers. The Fc-multimer constructs of interest or controls were serially diluted in sterile PBS to the indicated concentrations. 12.5 µl of Fc-multimer or control was added to the assay plates, followed by 237.5 µl of whole blood. The plate was incubated at 37° C. without $CO_2$ supplementation for 24 hrs. Plates were centrifuged at 1800 rpm for 5 minutes and the serum removed for cytokine analysis. Cytokine analysis was performed by Meso Scale Discovery cytokine multiplex according to the manufacturer's protocol and read on a Sector Imager 6000.

Results are shown in FIG. 8. The data demonstrated that wild type IgG1 Fc-multimers, both with and without L309C, stimulate very high levels of cytokine release. The observed levels of cytokines were higher than those produced by the positive control, Campath. In marked contrast, IgG4 Fc-multimers, and IgG1 Fc-multimers comprising the FcγR and C1q inert "LALA" mutation (L234A L235A), produced virtually zero cytokine release.

In order to assess the effect of any given Fc-multimer construct on cytokine release its activity was measured in the assay described herein above and compared with the activities of IgG1 and IgG4 wild type Fc-multimers. The activity of the mutant was then summarised as "IgG1-like", "high", "medium", "low", or "IgG4-like", based on a visual comparison of its concentration vs. effect curve with those obtained for IgG1 and IgG4 wild type Fc-multimers.

Results for Fc-multimers comprising single cross-over mutations at selected positions of difference in the IgG1 and IgG4 Fc region are shown in FIG. 9 and summarised in Table 8.

The results demonstrated that wild type IgG1 Fc-multimer, comprising a CH2 and a CH3 domain derived from IgG1, stimulates the release of very significant levels of cytokines. The results shown are for IFNγ. Similar results were observed for TNFα.

Two of the single mutations (L234F, A327G) significantly reduced cytokine release in IgG1 Fc-multimers. One of the single mutations (Y296F) produced a moderate reduction of cytokine release. One of the mutations (P331S) significantly increased cytokine release. Three of the mutations (H268Q, K274Q, A330S) had no effect on cytokine release.

In marked contrast, wild type IgG4 Fc-multimer, comprising a CH2 and a CH3 domain derived from IgG4, produced virtually no cytokine release. None of the single cross-over mutations had any effect on cytokine release by IgG4 Fc-multimers, not even those at positions shown to be important for cytokine release in the IgG1 Fc-multimers.

TABLE 8

| Fc-multimer | stimulation of IFNγ release |
| --- | --- |
| IgG1 Fc IgM tp L309 | the standard for "IgG1-like" |
| IgG1 Fc IgM tp L309 L234F | low |
| IgG1 Fc IgM tp L309 H268Q | IgG1-like |
| IgG1 Fc IgM tp L309 K274Q | IgG1-like |
| IgG1 Fc IgM tp L309 Y296F | medium |
| IgG1 Fc IgM tp L309 A327G | low |
| IgG1 Fc IgM tp L309 A330S | IgG1-like |
| IgG1 Fc IgM tp L309 P331S | higher than IgG1 |
| IgG1 Fc IgM tp L309 K409R | higher than IgG1 |
| IgG4 Fc IgM tp L309 | the standard for "IgG4-like" |
| IgG4 Fc IgM tp L309 F234L | IgG4-like |
| IgG4 Fc IgM tp L309 Q268H | IgG4-like |
| IgG4 Fc IgM tp L309 Q274K | IgG4-like |
| IgG4 Fc IgM tp L309 F296Y | IgG4-like |
| IgG4 Fc IgM tp L309 G327A | IgG4-like |
| IgG4 Fc IgM tp L309 S330A | IgG4-like |
| IgG4 Fc IgM tp L309 S331P | IgG4-like |
| IgG4 Fc IgM tp L309 R409K | IgG4-like |

Results for further Fc-multimer constructs designed to modulate cytokine release are shown in FIG. 10 and summarised in Table 9.

The data shows that cytokine release by IgG1 Fc-multimers can be reduced to levels approximately equivalent to IVIG by inclusion of L234F alone or in combination with P331S. Such Fc-multimers may be useful for the treatment of immune disorders. All the IgG4 Fc-multimers containing mutations shown to have other useful properties, for example enhanced potency in phagocytosis (Example 6), retain virtually zero levels of cytokine release, and may thus be useful for the treatment of immune disorders.

TABLE 9

Cytokine release by Fc-multimers

| Fc-multimer | stimulation of IFNγ release |
| --- | --- |
| IgG1 Fc IgM tp L309 | the standard for "IgG1-like" |
| IgG4 Fc IgM tp L309 | the standard for "IgG4-like" |
| IgG1 Fc IgM tp L309 L234F | low |
| IgG1 Fc IgM tp L309 L234F P331S | medium |
| Hybrid Fc IgG4-CH2 IgG1-CH3 IgM tp L309 | IgG4-like |
| IgG4 Fc IgM tp L309 F234L | IgG4-like |
| IgG4 Fc IgM tp L309 F234L F296Y | IgG4-like |
| IgG4 Fc IgM tp L309 G327A S330A | IgG4-like |
| IgG4 Fc IgM tp L309 G327A S331P | IgG4-like |
| IgG4 Fc IgM tp L309 S330A S331P | IgG4-like |

Example 9: Effect on IgG Recycling in Cells in Culture

Cell-based assays were performed using Madin-Darby Canine Kidney (MDCK) II cells which had been stably transfected with a human FcRn and human β2M double gene vector with a Geneticin selection marker. A stable cell clone was selected that was able to recycle and transcytose human IgG and this was used for all subsequent studies. It will be referred to as MDCK II clone 15. Equivalent MDCK cell lines, transfected with either cynomolgus monkey ("clone 40") or mouse FcRn have been generated in a similar way, for use in assays equivalent to the above.

An in vitro assay was established to examine the ability of a multimeric fusion protein of the present invention to inhibit the IgG-recycling capabilities of FcRn. Briefly, MDCK II clone 15 cells were incubated with biotinylated human IgG (1 µg/ml) in the presence or absence of the multimeric fusion protein in an acidic buffer (pH 5.9) to allow binding to FcRn. After a pulse time of 60 mins, all excess protein was removed and the cells incubated in a neutral pH buffer (pH 7.2) which allowed release of surface-exposed, bound IgG into the supernatant. The inhibition of FcRn was followed using an MSD assay to detect the amount of IgG recycled and thus released into the supernatant.

MDCK II clone 15 cells were plated at 15,000 cells per well in a 96 well plate and incubated overnight at 37° C., 5% $CO_2$. The cells were incubated with 1 µg/ml of biotinylated human IgG (Jackson) in the presence and absence of the multimeric fusion protein in HBSS+(Ca/Mg) pH 5.9+1% BSA for 1 hour at 37° C., 5% $CO_2$. The cells were washed with HBSS+pH 5.9 then incubated at 37° C., 5% CO2 for 2 hours in HBSS+pH 7.2. The lysates and supernatant were removed and analysed for total IgG using an MSD assay (using an anti-human IgG capture antibody (Jackson) and a streptavidin-sulpho tag reveal antibody (MSD)). The inhibition curve was analysed by non-linear regression (Graphpad Prism) to determine the $EC_{50}$.

The results demonstrated that the multimeric fusion proteins of the invention inhibit FcRn-mediated IgG recycling. (FIG. 11). Human IgG1 Fc/IgM tailpiece multimers which retain the native histidine residue at position 310 block FcRn-mediated IgG transcytosis and recycling in a concentration-dependent manner, both with and without cysteine at position 309. The data clearly shows that the form lacking L309C is more potent than that with L309C. Although we do not wish to be bound by theory, it is likely that this difference is due to steric hindrance by L3090 disulphide bonds adjacent to the histidine residue at position 310 which is critically involved in FcRn binding.

Table 10 shows the effects of mutations on the blocking activity of Fc-multimers. Three mutations that increase binding to FcRn, V308F, V308P and T307A, were tested in Fc-multimers comprising IgG1 Fc/IgM tailpiece or IgG4 Fc/IgM tailpiece. The results showed significant improvements in the ability of the Fc-multimers to block FcRn-mediated IgG intracellular uptake and IgG recycling. The data demonstrates the utility of these mutations for improving the potency of Fc-multimers comprising either IgG1 or IgG4 Fc-regions.

Substitution of histidine at position 310 with leucine (H310L) was shown to destroy the ability of the Fc-multimers to block FcRn-mediated IgG intracellular uptake and IgG recycling. The results demonstrate that Fc-multimers which retain the histidine residue at position 310 have much better binding to FcRn, and are more potent blockers of IgG intracellular uptake and IgG recycling. The data confirms that the Fc-multimers of the invention may provide new improved therapeutic compositions with longer half-life and greater efficacy.

TABLE 10

| Effects of mutations on Fc-multimer blockade of IgG intracellular uptake and IgG recycling | | |
|---|---|---|
| Fc-multimer mutants | Blockade of IgG intracellular uptake $EC_{50}$ (μg/ml) | Blockade of IgG recycling $EC_{50}$ (μg/ml) |
| IgG1 IgM tail-piece, Wild-type | 4.4 | 0.33 |
| IgG1 IgM tail-piece, V308F | 0.12 | 0.073 |
| IgG1 IgM tail-piece, V308P | 0.34 | 0.55 |
| IgG1 IgM tail-piece, T307A | 0.54 | 0.35 |

TABLE 10-continued

Effects of mutations on Fc-multimer blockade of IgG intracellular uptake and IgG recycling

| Fc-multimer mutants | Blockade of IgG intracellular uptake EC$_{50}$ (µg/ml) | Blockade of IgG recycling EC$_{50}$ (µg/ml) |
|---|---|---|
| IgG1 IgM tail-piece, H310L | No detectable inhibition | Maximal 45% inhibition at 100 µg/ml |
| IgG4 IgM tail-piece, Wild-type | 5.9 | 1.0 |
| IgG4 IgM tail-piece, V308F | 0.42 | 0.56 |
| IgG4 IgM tail-piece, V308P | 0.51 | 0.42 |
| IgG4 IgM tail-piece, T307A | 0.50 | Not tested |

Example 10: Efficacy of Fc-Multimers in Acute ITP

Efficacy of Fc-multimers was studied in a mouse model of ITP, in which platelet loss is induced by administration of anti-CD41. This antibody binds to glycoprotein IIb on the surface of the platelets, targeting them for destruction.

ITP In Vivo Protocol

A 5 µl blood sample was taken from the tails of the mice prior to dosing to obtain baseline platelet numbers.

Mice were dosed i.v. with 1 mg/kg or 10 mg/kg Fc-multimers.

An hour later 1 µg/mouse rat anti-mouse CD41 IgG1 antibody (MWReg30) was dosed i.p.

Terminal cardiac puncture was performed 24 hours after anti-CD41 administration.

FACs Staining Protocol

5 µl of blood was taken from the tail vein. For terminal samples blood was taken by cardiac puncture into a heparin tube and 5 µl was taken for staining. 100 µl of antibody cocktail was added to the 5 µl blood sample and was incubated at 4° C. in the dark for 20 minutes. 5 mls of FACs buffer was added.

Each sample was diluted 1:4 to make a final volume of 200 µl in a 'vee' bottom plate and kept on ice until ready to acquire on the Becton Dickinson FACs Canto.

TABLE 11

| Antibody name/Clone | Antibody Colour | Dilution | Supplier/Lot number |
|---|---|---|---|
| CD45 (30-F11) | PerCPCy5.5 | 1/400 | Ebio E08336-1633 |
| CD42d (1C2) | PE | 1/200 | Ebio E14346-104 |
| Fc block | | 1/200 | |

FACS Acquisition

A set volume of 150 µl of sample was collected at a flow rate of 1.5 µl/sec. The threshold was set at 200.

Analysis was performed on FlowJo software. Platelet counts were derived from the CD45−/CD42d+ gated cells.

Cell counts were corrected for sample dilution based on the fact that the initial 5 µl blood sample is diluted 1/4000 and 150 µl of this is run through the FACs machine which equates to 0.1875 µl of the original sample being analysed. 5/0.1875=multiplication factor of ×26.7 for platelet/µl.

Reagents

Rat anti mouse CD41 Functional grade purified (Ebiosciences, MWReg30, lot #E11914-1632)

Endotoxin free PBS (Sigma, D8537)

FACs buffer: 0.1% FCS, 2 mM EDTA

Results

Human multimeric fusion proteins ('Fc-multimers') at 1 mg/kg dose were well tolerated. However they were not efficacious at this dose in the model. Positive results were observed using 10 mg/kg human Fc-multimers.

Fc-multimers with either an IgM or an IgA tailpiece significantly inhibited platelet decrease caused by the injection of 1 µg/mouse anti-CD41.

The results demonstrated that Fc-multimers prevent platelet loss in an in vivo model of acute immune thrombocytopenia. Statistically significant reductions in platelet loss were achieved using human IgG1 Fc/IgM tailpiece multimers, both with and without L309C, and human IgG4 Fc/IgM tailpiece multimers with L309C, at a dose of 10 mg/kg. (FIG. 12) Thus, multimeric fusion proteins hexamerised through the tailpiece alone, or via L309C disulphide and tailpiece, are efficacious in vivo. Human IVIG is active in this model only at a much higher dose of 1000 mg/kg. At the equivalent dose of 10 mg/kg, IVIG was found to be inactive in preventing platelet loss.

Example 11: Efficacy of Fc-Multimers in Chronic ITP

Efficacy of Fc-multimers was studied in a mouse model of chronic ITP, in which platelet loss is induced by administration of anti-CD41 for a sustained period of time using minipumps.

ITP In Vivo Protocol

A 5 ul tail bleed was taken prior to dosing to obtain baseline platelet numbers. An alzet mini pump containing rat anti-mouse CD41 at a concentration of 82.5 ug/ml (57.75 ul rat anti-mouse CD41 Ab+642.25 ul PBS/BSA (1.5 mg/ml)) was implanted subcutaneously. The pumps have a flow rate of 0.5 ul/hour, dosing the equivalent of 0.99 ug of anti-CD41 per day.

5 ul tail bleeds to obtain platelet counts were done daily.

At a time point when a steady state platelet count has been reached mice are dosed intravenously with 1 g/kg IVIg, or Fc-multimers at a range of doses.

At 7 days a terminal cardiac puncture was performed.

FACs Staining Protocol

Take 5 ul of blood via the tail vein. For terminal samples take blood by cardiac puncture into a heparin tube and take 5 ul for staining.

Add 100 ul of antibody cocktail and incubate at 4° C. in the dark for 20 minutes. Add 5 mls of FACs buffer Dilute each sample 1:4 to make a final volume of 200 ul in a v-bottom plate and keep on ice until ready to acquire on the BD FACs Canto.

TABLE 12

| Antibody name/Clone | Antibody Colour | Dilution | Supplier/Lot number |
|---|---|---|---|
| CD45 (30-F11) | PerCPCy5.5 | 1/400 | Ebio E08336-1633 |
| CD42d (1C2) | PE | 1/200 | Ebio E14346-104 |
| Fc block | | 1/200 | |

FACS Acquisition

A set volume of 150 ul of sample will be collected at a flow rate of 1.5 ul/sec. The threshold will be set at 200.

Analysis will be performed on FlowJo software. Platelet counts will be derived from the CD45−CD42d+ gated cells.

Cell counts will be corrected for sample dilution based on the initial 5 ul blood sample is diluted 1/4000 and 150 ul of this is run through the FACs machine which equates to 0.1875 ul of the original sample being analysed. 5/0.1875=multiplication factor of ×26.7 for platelet/ul.
Reagents
Rat anti mouse CD41 Functional grade purified (Ebiosciences, MWReg30, lot #E11914-1632)
Endotoxin free PBS (Sigma, D8537)
FACs buffer: 0.1% FCS, 2 mM EDTA
10 mg/kg IgG1 IgM tp, (ID:PB0000238), EWBE-017553, 5.69 mg/mg,
Endototoxin<0.35 EU/mg
IgG1 Fc IgM tp L309C, (ID:PB0000198), EWBE-017400, 6.49 mg/ml, Endotoxin<0.46 EU/mg
IVIg: Gammunex lot #26NK1 N1.

The results demonstrated that the multimeric fusion proteins prevent platelet loss in an in vivo model of chronic thrombocytopenia. FIG. 13 shows the effects achieved using (a) a single dose of 10 mg/kg Fc-multimer, administered on day 3; and (b) four consecutive daily doses, 10 mg/kg per dose, administered on days 3, 4, 5, and 6. Multiple doses of Fc-multimer increased their effectiveness in preventing platelet loss. Human IVIG was effective only at a much higher dose of 1000 mg/kg.

Example 12: Disulphide Bond and Glycan Analysis of Hexameric Fc-Multimers by Mass Spectrometry Method Purified samples of hexameric Fc-multimers (100 ug) were denatured in the presence of 8M urea in 55 mM Tris-HCl pH8.0 and free thiols were capped by incubating with 22 mM iodoacetamide (IAM) for 60 minutes at 37° C. The urea concentration was reduced to 6M using ultrafiltration and protein was digested with a LysC/trypsin mix (Promega) for 3 hours at 37° C. The sample was further diluted with 5 volumes of buffer and the digestion continued overnight at 37° C. Peptides were collected, desalted with Waters Oasis HLB cartridges, dried using a centrifugal evaporator and reconstituted in water containing 0.2% formic acid (solvent A).

Samples (7.5 uL, ~7 ug) were loaded at 150 uL/min onto a 2.1×150 mm C18 column (Waters 1.7u PST 300A) equilibrated with solvent A and operated at 40° C. Peptides were eluted by a 60 min gradient to 50% solvent B (4:4:1 acetonitrile:1-propanol:water/0.2% formic acid) into a Waters Xevo mass spectrometer operated in MS$^E$+ve-ion mode. MS$^E$ data, which consists of alternating scans of low and high collision energy, was collected over the range 100-1900 m/z. during elution. After running, the digests were reduced by adding 10 mM Tris(hydroxypropyl)phosphine (THP) solution directly to the autosampler vial and incubating for >1 hr at room temperature. Reduced samples were then analysed a second time.

MS$^E$ data was searched against the relevant Fc-multimer sequence using Waters BiopharmaLynx™ (BPL). The proportion of free disulphide thiols was calculated from the ratio of IAM-labelled to free peptide in the THP reduced digest. Glycan profiles were determined from the various glycopeptide isoforms detected in the digests.

Results

The results for glycan analysis of Fc-multimers (IgG1 Fc/IgM tailpiece), with and without L309C, are shown in Table 13. Glycan structures are shown in Table 8.

The data demonstrates high occupancy of N297, the glycosylation site in the IgG1 Fc-region, with less than 10% free asparagine residues being found at this position. Glycosylation at N297 was mainly fucosylated biantennary complex, primarily G0F. Occupancy of the IgM tailpiece site, N563, was about 50%, higher than the level of about 20% found in native IgM. Glycosylation at N563 was mainly high mannose.

TABLE 13

| | | Glycan analysis | | | | | | |
|---|---|---|---|---|---|---|---|---|
| | | Occupancy | G0F-N | G2-F | G1-F | G0-F | M6 | M5 |
| IgG1 Fc IgM tp L309C | CH2 N297 | 93% | 14% | 5% | 20% | 38% | 1% | 15% |
| | Tail piece N563 | 59% | <1% | 7% | 5% | 2% | 24% | 20% |
| IgG1 Fc IgM tp | CH2 N297 | 91% | 14% | <1% | 26% | 34% | <1% | 15% |
| | Tail piece N563 | 45% | 1% | 4% | 3% | <1% | 14% | 22% |

Results for analysis of interchain disulphide bonds are shown in Table 14. Similar results were also obtained for intrachain disulphide bonds. The data demonstrated that a high proportion of the cysteine residues in the Fc-multimers are disulphide bonded. There was no evidence for significant amounts of scrambled disulphide bonding, and all expected dipeptides were found at high levels before reduction.

TABLE 14

| | Interchain Disulphide bonds | | |
|---|---|---|---|
| | | DSB (%) | 'Free' thiol (%) |
| IgG1 Fc IgM tp L309C | Hinge | 97 | 3 |
| | CH2 L309C-L309C | 89 | 10 |
| | Tail piece C575-C575 | 84 | 14 |
| IgG1 IgM tp | Hinge | 96 | 4 |
| | Tail piece C575-C575 | 80 | 19 |

Example 13: Binding of Fc-Multimers to C1q

Binding of Fc-multimers to C1q was measured by enzyme-linked immunosorbent assay (ELISA), using a C1q ELISA kit from Abnova Corporation, catalogue number: KA1274, lot number: V14-111723527. The Fc-multimer constructs were titrated in five-fold dilutions from 500 μg/ml through to 4 μg/ml. 100 μl of each Fc-multimer construct was added to the appropriate well, and agitated for one hour to enable binding. The assay was then carried out according to the manufacturer's protocol and analysed on a plate reader at an absorbance of 450 nm.

In order to assess the binding of any given Fc-multimer construct to C1q, its activity was measured and compared with the activities of IgG1 and IgG4 wild type Fc-multimers. The activity of the mutant was then summarised as "IgG1-like", "high", "medium", "low", or "IgG4-like", based on a visual comparison of its concentration vs. effect curve with those obtained for IgG1 and IgG4 wild type Fc-multimers.

The results are shown in FIG. 14 and summarised in Table 15.

The results demonstrated that wild type IgG1 Fc-multimer, comprising a CH2 and a CH3 domain derived from IgG1, binds strongly to C1 q. In contrast, wild type IgG4 Fc-multimer, comprising a CH2 and a CH3 domain derived from IgG4, binds very poorly to C1 q. The dominant residue defining C1q binding in the Fc-multimers was found to be proline at position 331 (P331). Substitution of this proline residue with serine (P331S) effectively reduced C1q binding in Fc-multimers with a CH2 domain derived from IgG1. The converse mutant, S331P, increased C1q binding in Fc-multimers with a CH2 domain derived from IgG4.

TABLE 15

Binding of Fc-multimers to C1q

| Fc-multimer | C1q binding |
| --- | --- |
| IgG1 Fc IgM tp L309 | the standard for "IgG1-like" |
| IgG4 Fc IgM tp L309 | the standard for "IgG4-like" |
| IgG1 Fc IgM tp L309 L234F | IgG1-like |
| IgG1 Fc IgM tp L309 P331S | low |
| IgG1 Fc IgM tp L309 L234F P331S | IgG4-like |
| Hybrid Fc IgG4-CH2 IgG1-CH3 IgM tp L309 | IgG4-like |
| IgG4 Fc IgM tp L309 F234L | IgG4-like |
| IgG4 Fc IgM tp L309 F234L F296Y | IgG4-like |
| IgG4 Fc IgM tp L309 G327A S330A | IgG4-like |
| IgG4 Fc IgM tp L309 G327A S331P | medium |
| IgG4 Fc IgM tp L309 S330A S331P | medium |

Example 14: Platelet Activation

Platelet activation by Fc-multimers was analysed by flow cytometry. Two-fold dilutions of Fc-multimer were prepared in RMPI medium and transferred to FACS tubes. The final concentration was from 100 µg/ml down to 3.12 µg/ml. 5 µl fresh whole blood (from a minimum of 2 human donors) was added per tube. Platelets were gated using anti-CD42b labelled Mab and activation followed with Mabs against markers: CD62p, CD63 and PAC-1. (Becton Dickinson, BD CD42b APC Cat:551061, BD CD62p PE Cat:550561, BD CD63 PE-Cy-7 Cat:561982, BD PAC-1 FITC Cat:340507). Cells were fixed by addition of 500 µl paraformaldehyde 1% before analysis by flow-cytometry.

CD62p was found to be the most sensitive of the three markers tested.

In order to assess the platelet activation by any given Fc-multimer construct, its activity was measured and compared with the activities of IgG1 and IgG4 wild type Fc-multimers. The activity of the mutant was then summarised as "IgG1-like", "high", "medium", "low", or "IgG4-like", based on a visual comparison of its concentration vs. effect curve with those obtained for IgG1 and IgG4 wild type Fc-multimers.

Results for induction of CD62p expression are shown in FIG. 15 and summarised in Table 16.

The results demonstrated that wild type IgG1 Fc-multimer, comprising a CH2 and a CH3 domain derived from IgG1, results in significant levels of platelet activation.

We have shown in Example 8 that two mutations are useful for reducing cytokine release from IgG1 Fc-multimer, L234F and A327G. Of these two mutations, L234F has much reduced levels of platelet activation compared to IgG1 wild-type Fc-domain, whereas an Fc-multimer with the A327G mutation retains significant levels of platelet activation. Thus L234F is a very useful mutation—it reduces cytokine release and platelet activation with only minor loss of potency in the inhibition of macrophage phagocytosis.

Addition of P331S (shown in Example 13 to be a useful C1q reducing mutation) to L234F (L234F P331 S) results in low levels of platelet activation. This double mutant is a means of achieving low cytokine, low platelet activation and zero C1q binding. Thus this combination of mutations is particularly useful and is expected to provide new therapies for the treatment of immune disorders.

L234F may be dominant over A327G since the triple L234F A327G P331S mutant has low platelet activation.

Wild type IgG4 Fc-multimer, comprising a CH2 and a CH3 domain derived from IgG4, results in virtually no platelet activation.

Switching the CH3 domain to that of IgG1 retains these reduced levels of platelet activation.

The F234L mutation has low levels of platelet activation (and enhanced potency)—but the platelet activation is increased in comparison with wild type IgG4 Fc-multimer.

F296Y can be combined with F234L without additionally increasing platelet activation. This observation is important since F234L F296Y has increased potency compared to IgG4 wild type Fc-multimers. Thus this combination of mutations is particularly useful and is expected to provide new therapies for the treatment of immune disorders.

G327A mutation does not increase platelet activation. This observation is surprising in view of the results for the reverse mutation A327G in IgG1 Fc-multimers, which retained high levels of platelet activation.

Certain double mutants (G327A S330A, G327A S331P and S330A S331P) which also have enhanced potency over IgG4 WT have very low levels of platelet activation (IgG4 like) and are expected to provide new therapies for the treatment of immune disorders.

TABLE 16

Platelet activation by Fc-multimers

| Fc-multimer | CD62p |
| --- | --- |
| IgG1 Fc IgM tp L309 | the standard for "IgG1-like" |
| IgG4 Fc IgM tp L309 | the standard for "IgG4-like" |
| IgG1 Fc IgM tp L309 L234F | low |
| IgG1 Fc IgM tp L309 L234F P331S | IgG4-like |
| IgG1 Fc IgM tp L309 A327G | IgG1-like |
| IgG1 Fc IgM tp L309 A327G A330S P331S | IgG1-like |
| IgG1 Fc IgM tp L309 A327G P331S | IgG1-like |
| IgG1 Fc IgM tp L309 L234F A327G P331S | medium |
| Hybrid Fc IgG4-CH2 IgG1-CH3 IgM tp L309 | low |
| IgG4 Fc IgM tp L309 F234L | medium |
| IgG4 Fc IgM tp L309 F234L F296Y | medium |
| IgG4 Fc IgM tp L309 G327A S330A | IgG4-like |
| IgG4 Fc IgM tp L309 G327A S331P | IgG4-like |
| IgG4 Fc IgM tp L309 S330A S331P | low |

Example 15: Engineering of Fc-Multimer Variants

The previous examples illustrate that Fc-multimers have been created that are particularly suitable for use in the treatment of immune disorders. The Fc-multimers were engineered with the aim of generating Fc multimers which possess the following properties:

Inhibition of Macrophage Phagocytosis of Antibody Coated Target Cells.

The potency of the Fc-multimer should be as high as possible.

Cytokine Release.

Stimulation of cytokine release by the Fc-multimer should be as low as possible.

C1q Binding.

Binding of the Fc-multimer to C1q should be as low as possible.

Platelet Activation.

Platelet activation by the Fc-multimer should be as low as possible.

However, the work in the previous examples has illustrated that it may be necessary to compromise between maximum potency and slightly lower potency in order to achieve reduced side effects.

Wild type IgG1 Fc-multimer comprising a CH2 and CH3 domain derived from IgG1 without any additional mutations may be less suitable for use in the treatment of immune disorders because, although it displays high potency of phagocytosis inhibition, it also shows high levels of unwanted side effects, measured by cytokine release, C1q binding and platelet activation.

Wild type IgG4 Fc-multimer comprising a CH2 and CH3 domain derived from IgG4, produces very low levels of unwanted side effects although its potency is low relative to that of IgG1. Notwithstanding, the potency of wild type IgG4 Fc-multimer is still significantly higher than that of IVIG, as shown in FIG. 7.

Fc-multimers have been designed which combine the desirable properties of both IgG1 and IgG4 wild type Fc-multimers, without the undesirable properties. These Fc-multimers display effective levels of potency, whilst reducing unwanted side effects to a tolerable level as shown below in Table 17. These Fc-multimers are expected to be particularly useful for use in the treatment of immune disorders.

TABLE 17

| Fc-multimer | phagocytosis inhibition | IFNγ release | C1q binding | platelet activation |
|---|---|---|---|---|
| wild type IgG1 Fc-multimer | the standard for "IgG1-like" | the standard for "IgG1-like" | the standard for "IgG1-like" | the standard for "IgG1-like" |
| wild type IgG4 Fc-multimer | the standard for "IgG4-like" | the standard for "IgG4-like" | the standard for "IgG4-like" | the standard for "IgG4-like" |
| IgG1 Fc IgM tp L309 L234F P331S | high | medium | IgG4-like | IgG4-like |
| Hybrid Fc IgG4-CH2 IgG1-CH3 IgM tp L309 | medium | IgG4-like | IgG4-like | low |
| IgG4 Fc IgM tp L309 F234L | medium | IgG4-like | IgG4-like | medium |
| IgG4 Fc IgM tp L309 F234L F296Y | medium | IgG4-like | IgG4-like | medium |
| IgG4 Fc IgM tp L309 G327A S330A | medium | IgG4-like | IgG4-like | IgG4-like |
| IgG4 Fc IgM tp L309 G327A S331P | medium | IgG4-like | medium | IgG4-like |
| IgG4 Fc IgM tp L309 S330A S331P | medium | IgG4-like | medium | IgG4-like |

The invention claimed is:

1. A multimeric fusion protein comprising two or more polypeptide monomer units;
   wherein each polypeptide monomer unit comprises an antibody Fc-domain comprising two heavy chain Fc-regions;
   wherein each heavy chain Fc-region comprises any amino acid residue other than cysteine at position 309, and is fused at its C-terminal to a tailpiece of a naturally occurring IgM which causes the monomer units to assemble into a multimer;
   wherein each polypeptide monomer unit does not comprise an antibody variable region or an N-terminal fusion partner; and
   wherein each heavy chain Fc-region comprises either:
   IgG1 CH2 and CH3 domains comprising SEQ ID NO: 36, in which the leucine residue at position 234 has been substituted with a phenylalanine residue and the proline residue at position 331 has been substituted with a serine residue (L234F/P331S),
   IgG4 CH2 and CH3 domains comprising SEQ ID NO: 37, in which the phenylalanine residue at position 234 has been substituted with a leucine residue (F234L),
   IgG4 CH2 and CH3 domains comprising SEQ ID NO: 38, in which the phenylalanine residue at position 234 has been substituted with a leucine residue and the phenylalanine residue at position 296 has been substituted with a tyrosine residue (F234L/F296Y),
   IgG4 CH2 and CH3 domains comprising SEQ ID NO: 39, in which the glycine residue at position 327 has been substituted with an alanine residue and the serine residue at position 330 has been substituted with an alanine residue (G327A/S330A),
   IgG4 CH2 and CH3 domains comprising SEQ ID NO: 40, in which the glycine residue at position 327 has been substituted with an alanine residue and the serine residue at position 331 has been substituted with a proline residue (G327A/S331P),
   IgG4 CH2 and CH3 domains comprising SEQ ID NO: 41, in which the serine residue at position 330 has been substituted with an alanine residue and the serine residue at position 331 has been substituted with a proline residue (S330A/S331P), or
   an IgG4 CH2 domain and an IgG1 CH3 domain comprising SEQ ID NO: 43, and wherein the EU numbering system is used for residue numbering, and further wherein the residue substitutions identified above are the only residue substitutions made.

2. The multimeric fusion protein of claim 1, wherein each heavy chain Fc-region comprises CH2 and CH3 domains from IgG1 in which the leucine residue at position 234 has been substituted with a phenylalanine residue and the proline residue at position 331 has been substituted with a serine residue (L234F/P331S).

3. The multimeric fusion protein of claim 1, wherein each heavy chain Fc-region comprises CH2 and CH3 domains comprising SEQ ID NO: 37, derived from IgG4 in which the phenylalanine residue at position 234 has been substituted with a leucine residue (F234L).

4. The multimeric fusion protein of claim 1, wherein each heavy chain Fc-region comprises CH2 and CH3 domains comprising SEQ ID NO: 38, derived from IgG4 in which the phenylalanine residue at position 234 has been substituted with a leucine residue and the phenylalanine residue at position 296 has been substituted with a tyrosine residue (F234L/F296Y).

5. The multimeric fusion protein of claim 1, wherein each heavy chain Fc-region comprises CH2 and CH3 domains comprising SEQ ID NO: 39, derived from IgG4 in which the glycine residue at position 327 has been substituted with an alanine residue and the serine residue at position 330 has been substituted with an alanine residue (G327A/S330A).

6. The multimeric fusion protein of claim 1, wherein each heavy chain Fc-region comprises CH2 and CH3 domains comprising SEQ ID NO: 40, derived from IgG4 in which the glycine residue at position 327 has been substituted with an alanine residue and the serine residue at position 331 has been substituted with a proline residue (G327A/S331P).

7. The multimeric fusion protein of claim 1, wherein each heavy chain Fc-region comprises CH2 and CH3 domains comprising SEQ ID NO: 41, derived from IgG4 in which the serine residue at position 330 has been substituted with an alanine residue and the serine residue at position 331 has been substituted with a proline residue (S330A/S331P).

8. A pharmaceutical composition comprising the multimeric fusion protein of claim 1, in combination with a pharmaceutically acceptable excipient, diluent or carrier.

9. The pharmaceutical composition according to claim 8 additionally comprising other active ingredients.

* * * * *

SEQUENCE LISTING

```
<160> NUMBER OF SEQ ID NOS: 59

<210> SEQ ID NO 1
<211> LENGTH: 18
<212> TYPE: PRT
<213> ORGANISM: Artificial Sequence
<220> FEATURE:
<223> OTHER INFORMATION: Tailpiece IgM

<400> SEQUENCE: 1

Pro Thr Leu Tyr Asn Val Ser Leu Val Met Ser Asp Thr Ala Gly Thr
1               5                   10                  15

Cys Tyr

<210> SEQ ID NO 2
<211> LENGTH: 18
<212> TYPE: PRT
<213> ORGANISM: Artificial Sequence
<220> FEATURE:
<223> OTHER INFORMATION: Tailpiece IgA

<400> SEQUENCE: 2

Pro Thr His Val Asn Val Ser Val Val Met Ala Glu Val Asp Gly Thr
1               5                   10                  15

Cys Tyr

<210> SEQ ID NO 3
<211> LENGTH: 19
<212> TYPE: PRT
<213> ORGANISM: Artificial Sequence
<220> FEATURE:
<223> OTHER INFORMATION: Hinge Human IgA1

<400> SEQUENCE: 3

Val Pro Ser Thr Pro Pro Thr Pro Ser Pro Ser Thr Pro Pro Thr Pro
1               5                   10                  15
```

Ser Pro Ser

<210> SEQ ID NO 4
<211> LENGTH: 6
<212> TYPE: PRT
<213> ORGANISM: Artificial Sequence
<220> FEATURE:
<223> OTHER INFORMATION: Hinge Human IgA2

<400> SEQUENCE: 4

Val Pro Pro Pro Pro Pro
1               5

<210> SEQ ID NO 5
<211> LENGTH: 58
<212> TYPE: PRT
<213> ORGANISM: Artificial Sequence
<220> FEATURE:
<223> OTHER INFORMATION: Hinge Human IgD

<400> SEQUENCE: 5

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro
    50                  55

<210> SEQ ID NO 6
<211> LENGTH: 15
<212> TYPE: PRT
<213> ORGANISM: Artificial Sequence
<220> FEATURE:
<223> OTHER INFORMATION: Hinge Human IgG1

<400> SEQUENCE: 6

Glu Pro Lys Ser Cys Asp Lys Thr His Thr Cys Pro Pro Cys Pro
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: Hinge Human IgG2

<400> SEQUENCE: 7

Glu Arg Lys Cys Cys Val Glu Cys Pro Pro Cys Pro
1               5                   10

<210> SEQ ID NO 8
<211> LENGTH: 62
<212> TYPE: PRT
<213> ORGANISM: Artificial Sequence
<220> FEATURE:
<223> OTHER INFORMATION: Hinge Human IgG3

<400> SEQUENCE: 8

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

```
Glu Pro Lys Ser Cys Asp Thr Pro Pro Cys Pro Arg Cys Pro Glu
    35                  40                  45

Pro Lys Ser Cys Asp Thr Pro Pro Cys Pro Arg Cys Pro
    50                  55                  60
```

<210> SEQ ID NO 9
<211> LENGTH: 12
<212> TYPE: PRT
<213> ORGANISM: Artificial Sequence
<220> FEATURE:
<223> OTHER INFORMATION: Hinge Human IgG4

<400> SEQUENCE: 9

```
Glu Ser Lys Tyr Gly Pro Pro Cys Pro Ser Cys Pro
1               5                   10
```

<210> SEQ ID NO 10
<211> LENGTH: 12
<212> TYPE: PRT
<213> ORGANISM: Artificial Sequence
<220> FEATURE:
<223> OTHER INFORMATION: Hinge Human IgG4(P)

<400> SEQUENCE: 10

```
Glu Ser Lys Tyr Gly Pro Pro Cys Pro Pro Cys Pro
1               5                   10
```

<210> SEQ ID NO 11
<211> LENGTH: 4
<212> TYPE: PRT
<213> ORGANISM: Artificial Sequence
<220> FEATURE:
<223> OTHER INFORMATION: Hinge Recombinant v1

<400> SEQUENCE: 11

```
Cys Pro Pro Cys
1
```

<210> SEQ ID NO 12
<211> LENGTH: 4
<212> TYPE: PRT
<213> ORGANISM: Artificial Sequence
<220> FEATURE:
<223> OTHER INFORMATION: Hinge Recombinant v2

<400> SEQUENCE: 12

```
Cys Pro Ser Cys
1
```

<210> SEQ ID NO 13
<211> LENGTH: 4
<212> TYPE: PRT
<213> ORGANISM: Artificial Sequence
<220> FEATURE:
<223> OTHER INFORMATION: Hinge Recombinant v3

<400> SEQUENCE: 13

```
Cys Pro Arg Cys
1
```

<210> SEQ ID NO 14
<211> LENGTH: 4
<212> TYPE: PRT
<213> ORGANISM: Artificial Sequence
<220> FEATURE:
<223> OTHER INFORMATION: Hinge Recombinant v4

<400> SEQUENCE: 14

Ser Pro Pro Cys
1

<210> SEQ ID NO 15
<211> LENGTH: 4
<212> TYPE: PRT
<213> ORGANISM: Artificial Sequence
<220> FEATURE:
<223> OTHER INFORMATION: Hinge Recombinant v5

<400> SEQUENCE: 15

Cys Pro Pro Ser
1

<210> SEQ ID NO 16
<211> LENGTH: 4
<212> TYPE: PRT
<213> ORGANISM: Artificial Sequence
<220> FEATURE:
<223> OTHER INFORMATION: Hinge Recombinant v6

<400> SEQUENCE: 16

Ser Pro Pro Ser
1

<210> SEQ ID NO 17
<211> LENGTH: 8
<212> TYPE: PRT
<213> ORGANISM: Artificial Sequence
<220> FEATURE:
<223> OTHER INFORMATION: Hinge Recombinant v7

<400> SEQUENCE: 17

Asp Lys Thr His Thr Cys Ala Ala
1               5

<210> SEQ ID NO 18
<211> LENGTH: 11
<212> TYPE: PRT
<213> ORGANISM: Artificial Sequence
<220> FEATURE:
<223> OTHER INFORMATION: Hinge Recombinant v8

<400> SEQUENCE: 18

Asp Lys Thr His Thr Cys Pro Pro Cys Pro Ala
1               5                   10

<210> SEQ ID NO 19
<211> LENGTH: 18
<212> TYPE: PRT
<213> ORGANISM: Artificial Sequence
<220> FEATURE:
<223> OTHER INFORMATION: Hinge Recombinant v9

<400> SEQUENCE: 19

Asp Lys Thr His Thr Cys Pro Pro Cys Pro Ala Thr Cys Pro Pro Cys
1               5                   10                  15

Pro Ala

<210> SEQ ID NO 20
<211> LENGTH: 25
<212> TYPE: PRT
<213> ORGANISM: Artificial Sequence
<220> FEATURE:

<223> OTHER INFORMATION: Hinge Recombinant v10

<400> SEQUENCE: 20

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 21
<211> LENGTH: 30
<212> TYPE: PRT
<213> ORGANISM: Artificial Sequence
<220> FEATURE:
<223> OTHER INFORMATION: Hinge Recombinant v11

<400> SEQUENCE: 21

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Hinge Recombinant v12

<400> SEQUENCE: 22

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 23
<211> LENGTH: 15
<212> TYPE: PRT
<213> ORGANISM: Artificial Sequence
<220> FEATURE:
<223> OTHER INFORMATION: Hinge Recombinant v13

<400> SEQUENCE: 23

Asp Lys Thr His Thr Cys Cys Val Glu Cys Pro Pro Cys Pro Ala
1               5                   10                  15

<210> SEQ ID NO 24
<211> LENGTH: 26
<212> TYPE: PRT
<213> ORGANISM: Artificial Sequence
<220> FEATURE:
<223> OTHER INFORMATION: Hinge Recombinant v14

<400> SEQUENCE: 24

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 25
<211> LENGTH: 11
<212> TYPE: PRT
<213> ORGANISM: Artificial Sequence
<220> FEATURE:
<223> OTHER INFORMATION: Hinge Recombinant v15

```
<400> SEQUENCE: 25

Asp Lys Thr His Thr Cys Pro Ser Cys Pro Ala
1               5                   10

<210> SEQ ID NO 26
<211> LENGTH: 240
<212> TYPE: PRT
<213> ORGANISM: Artificial Sequence
<220> FEATURE:
<223> OTHER INFORMATION: Human IgG1 Fc-multimer IgM tp

<400> SEQUENCE: 26

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys Pro Thr
    210                 215                 220

Leu Tyr Asn Val Ser Leu Val Met Ser Asp Thr Ala Gly Thr Cys Tyr
225                 230                 235                 240

<210> SEQ ID NO 27
<211> LENGTH: 240
<212> TYPE: PRT
<213> ORGANISM: Artificial Sequence
<220> FEATURE:
<223> OTHER INFORMATION: Human IgG4 Fc-multimer IgM tp

<400> SEQUENCE: 27

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser Gln Glu Asp Pro Glu Val
            35                  40                  45
```

```
Gln Phe Asn Trp Tyr Val Asp Gly Val Glu Val His Asn Ala Lys Thr
 50                  55                  60

Lys Pro Arg Glu Glu Gln Phe Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Pro Thr
        210                 215                 220

Leu Tyr Asn Val Ser Leu Val Met Ser Asp Thr Ala Gly Thr Cys Tyr
225                 230                 235                 240

<210> SEQ ID NO 28
<211> LENGTH: 240
<212> TYPE: PRT
<213> ORGANISM: Artificial Sequence
<220> FEATURE:
<223> OTHER INFORMATION: Human IgG1 Fc-multimer IgA tp

<400> SEQUENCE: 28

Cys Pro Pro Cys Pro Ala Pro Glu Leu Leu Gly Gly Pro Ser Val Phe
 1               5                  10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
 50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175
```

```
Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys Pro Thr
    210                 215                 220

His Val Asn Val Ser Val Val Met Ala Glu Val Asp Gly Thr Cys Tyr
225                 230                 235                 240
```

<210> SEQ ID NO 29
<211> LENGTH: 240
<212> TYPE: PRT
<213> ORGANISM: Artificial Sequence
<220> FEATURE:
<223> OTHER INFORMATION: Human IgG4 Fc-multimer IgA tp

<400> SEQUENCE: 29

```
Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Pro Thr
    210                 215                 220

His Val Asn Val Ser Val Val Met Ala Glu Val Asp Gly Thr Cys Tyr
225                 230                 235                 240
```

<210> SEQ ID NO 30
<211> LENGTH: 351
<212> TYPE: PRT
<213> ORGANISM: Artificial Sequence
<220> FEATURE:
<223> OTHER INFORMATION: Human IgG1 Fc-multimer C 4-IgM tp

<400> SEQUENCE: 30

```
Cys Pro Pro Cys Pro Ala Pro Glu Leu Leu Gly Gly Pro Ser Val Phe
1               5                   10                  15
```

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
 50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys Val Ala
    210                 215                 220

Leu His Arg Pro Asp Val Tyr Leu Leu Pro Pro Ala Arg Glu Gln Leu
225                 230                 235                 240

Asn Leu Arg Glu Ser Ala Thr Ile Thr Cys Leu Val Thr Gly Phe Ser
                245                 250                 255

Pro Ala Asp Val Phe Val Gln Trp Met Gln Arg Gly Gln Pro Leu Ser
            260                 265                 270

Pro Glu Lys Tyr Val Thr Ser Ala Pro Met Pro Glu Pro Gln Ala Pro
        275                 280                 285

Gly Arg Tyr Phe Ala His Ser Ile Leu Thr Val Ser Glu Glu Glu Trp
290                 295                 300

Asn Thr Gly Glu Thr Tyr Thr Cys Val Ala His Glu Ala Leu Pro Asn
305                 310                 315                 320

Arg Val Thr Glu Arg Thr Val Asp Lys Ser Thr Gly Lys Pro Thr Leu
                325                 330                 335

Tyr Asn Val Ser Leu Val Met Ser Asp Thr Ala Gly Thr Cys Tyr
            340                 345                 350

<210> SEQ ID NO 31
<211> LENGTH: 351
<212> TYPE: PRT
<213> ORGANISM: Artificial Sequence
<220> FEATURE:
<223> OTHER INFORMATION: Human IgG4 Fc-multimer C 4-IgM tp

<400> SEQUENCE: 31

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
                35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Val Ala
    210                 215                 220

Leu His Arg Pro Asp Val Tyr Leu Leu Pro Pro Ala Arg Glu Gln Leu
225                 230                 235                 240

Asn Leu Arg Glu Ser Ala Thr Ile Thr Cys Leu Val Thr Gly Phe Ser
                245                 250                 255

Pro Ala Asp Val Phe Val Gln Trp Met Gln Arg Gly Gln Pro Leu Ser
            260                 265                 270

Pro Glu Lys Tyr Val Thr Ser Ala Pro Met Pro Glu Pro Gln Ala Pro
        275                 280                 285

Gly Arg Tyr Phe Ala His Ser Ile Leu Thr Val Ser Glu Glu Glu Trp
    290                 295                 300

Asn Thr Gly Glu Thr Tyr Thr Cys Val Ala His Glu Ala Leu Pro Asn
305                 310                 315                 320

Arg Val Thr Glu Arg Thr Val Asp Lys Ser Thr Gly Lys Pro Thr Leu
                325                 330                 335

Tyr Asn Val Ser Leu Val Met Ser Asp Thr Ala Gly Thr Cys Tyr
            340                 345                 350

<210> SEQ ID NO 32
<211> LENGTH: 240
<212> TYPE: PRT
<213> ORGANISM: Artificial Sequence
<220> FEATURE:
<223> OTHER INFORMATION: Human IgG1 Fc-multimer IgM tp S267A

<400> SEQUENCE: 32

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ala His Glu Asp Pro Glu Val
                35                  40                  45

```
Lys Phe Asn Trp Tyr Val Asp Gly Val Glu Val His Asn Ala Lys Thr
 50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys Pro Thr
    210                 215                 220

Leu Tyr Asn Val Ser Leu Val Met Ser Asp Thr Ala Gly Thr Cys Tyr
225                 230                 235                 240

<210> SEQ ID NO 33
<211> LENGTH: 240
<212> TYPE: PRT
<213> ORGANISM: Artificial Sequence
<220> FEATURE:
<223> OTHER INFORMATION: IgG1 Fc IgM tp

<400> SEQUENCE: 33

Cys Pro Pro Cys Pro Ala Pro Glu Leu Leu Gly Gly Pro Ser Val Phe
 1               5                  10                  15

Leu Phe Pro Pro Lys Pro Lys Asp Thr Leu Met Ile Ser Arg Thr Pro
                 20                  25                  30

Glu Val Thr Cys Val Val Val Asp Val Ser His Glu Asp Pro Glu Val
             35                  40                  45

Lys Phe Asn Trp Tyr Val Asp Gly Val Glu Val His Asn Ala Lys Thr
 50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175
```

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys Pro Thr
    210                 215                 220

Leu Tyr Asn Val Ser Leu Val Met Ser Asp Thr Ala Gly Thr Cys Tyr
225                 230                 235                 240

<210> SEQ ID NO 34
<211> LENGTH: 240
<212> TYPE: PRT
<213> ORGANISM: Artificial Sequence
<220> FEATURE:
<223> OTHER INFORMATION: IgG4 Fc IgM tp

<400> SEQUENCE: 34

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Pro Thr
    210                 215                 220

Leu Tyr Asn Val Ser Leu Val Met Ser Asp Thr Ala Gly Thr Cys Tyr
225                 230                 235                 240

<210> SEQ ID NO 35
<211> LENGTH: 240
<212> TYPE: PRT
<213> ORGANISM: Artificial Sequence
<220> FEATURE:
<223> OTHER INFORMATION: IgG1 Fc IgM tp L234F

<400> SEQUENCE: 35

Cys Pro Pro Cys Pro Ala Pro Glu Phe Leu Gly Gly Pro Ser Val Phe

```
1               5                   10                  15
Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
                35                  40                  45

Lys Phe Asn Trp Tyr Val Asp Gly Val Glu Val His Asn Ala Lys Thr
 50                      55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                    85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
                115                 120                 125

Ser Arg Asp Glu Leu Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Val Phe Ser Cys Ser Val Met His Glu Ala Leu His
                195                 200                 205

Asn His Tyr Thr Gln Lys Ser Leu Ser Leu Ser Pro Gly Lys Pro Thr
        210                 215                 220

Leu Tyr Asn Val Ser Leu Val Met Ser Asp Thr Ala Gly Thr Cys Tyr
225                 230                 235                 240

<210> SEQ ID NO 36
<211> LENGTH: 240
<212> TYPE: PRT
<213> ORGANISM: Artificial Sequence
<220> FEATURE:
<223> OTHER INFORMATION: IgG1 Fc IgM tp L234F P331S

<400> SEQUENCE: 36

Cys Pro Pro Cys Pro Ala Pro Glu Phe Leu Gly Gly Pro Ser Val Phe
1                5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
                35                  40                  45

Lys Phe Asn Trp Tyr Val Asp Gly Val Glu Val His Asn Ala Lys Thr
 50                      55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                    85                  90                  95

Lys Val Ser Asn Lys Ala Leu Pro Ala Ser Ile Glu Lys Thr Ile Ser
                100                 105                 110

Lys Ala Lys Gly Gln Pro Arg Glu Pro Gln Val Tyr Thr Leu Pro Pro
                115                 120                 125

Ser Arg Asp Glu Leu Thr Lys Asn Gln Val Ser Leu Thr Cys Leu Val
```

```
                    130                 135                 140
Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys Pro Thr
            210                 215                 220

Leu Tyr Asn Val Ser Leu Val Met Ser Asp Thr Ala Gly Thr Cys Tyr
225                 230                 235                 240
```

<210> SEQ ID NO 37
<211> LENGTH: 240
<212> TYPE: PRT
<213> ORGANISM: Artificial Sequence
<220> FEATURE:
<223> OTHER INFORMATION: IgG4 Fc IgM tp F234L

<400> SEQUENCE: 37

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser Gln Glu Asp Pro Glu Val
            35                  40                  45

Gln Phe Asn Trp Tyr Val Asp Gly Val Glu Val His Asn Ala Lys Thr
        50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
            195                 200                 205

Asn His Tyr Thr Gln Lys Ser Leu Ser Leu Ser Leu Gly Lys Pro Thr
            210                 215                 220

Leu Tyr Asn Val Ser Leu Val Met Ser Asp Thr Ala Gly Thr Cys Tyr
225                 230                 235                 240
```

<210> SEQ ID NO 38
<211> LENGTH: 240
<212> TYPE: PRT

<213> ORGANISM: Artificial Sequence
<220> FEATURE:
<223> OTHER INFORMATION: IgG4 Fc IgM tp F234L F296Y

<400> SEQUENCE: 38

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Pro Thr
    210                 215                 220

Leu Tyr Asn Val Ser Leu Val Met Ser Asp Thr Ala Gly Thr Cys Tyr
225                 230                 235                 240
```

<210> SEQ ID NO 39
<211> LENGTH: 240
<212> TYPE: PRT
<213> ORGANISM: Artificial Sequence
<220> FEATURE:
<223> OTHER INFORMATION: IgG4 Fc IgM tp G327A S330A

<400> SEQUENCE: 39

```
Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95
```

```
Lys Val Ser Asn Lys Ala Leu Pro Ala Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Pro Thr
    210                 215                 220

Leu Tyr Asn Val Ser Leu Val Met Ser Asp Thr Ala Gly Thr Cys Tyr
225                 230                 235                 240

<210> SEQ ID NO 40
<211> LENGTH: 240
<212> TYPE: PRT
<213> ORGANISM: Artificial Sequence
<220> FEATURE:
<223> OTHER INFORMATION: IgG4 Fc IgM tp G327A S331P

<400> SEQUENCE: 40

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ser Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Pro Thr
    210                 215                 220
```

Leu Tyr Asn Val Ser Leu Val Met Ser Asp Thr Ala Gly Thr Cys Tyr
225                 230                 235                 240

<210> SEQ ID NO 41
<211> LENGTH: 240
<212> TYPE: PRT
<213> ORGANISM: Artificial Sequence
<220> FEATURE:
<223> OTHER INFORMATION: IgG4 Fc IgM tp S330A S331P

<400> SEQUENCE: 41

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys Pro Thr
    210                 215                 220

Leu Tyr Asn Val Ser Leu Val Met Ser Asp Thr Ala Gly Thr Cys Tyr
225                 230                 235                 240

<210> SEQ ID NO 42
<211> LENGTH: 240
<212> TYPE: PRT
<213> ORGANISM: Artificial Sequence
<220> FEATURE:
<223> OTHER INFORMATION: IgG1 CH2 IgG4 CH3 IgM tp

<400> SEQUENCE: 42

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
            85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
            115                 120                 125

Ser Gln Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
            195                 200                 205

Asn His Tyr Thr Gln Lys Ser Leu Ser Leu Ser Leu Gly Lys Pro Thr
210                 215                 220

Leu Tyr Asn Val Ser Leu Val Met Ser Asp Thr Ala Gly Thr Cys Tyr
225                 230                 235                 240

<210> SEQ ID NO 43
<211> LENGTH: 240
<212> TYPE: PRT
<213> ORGANISM: Artificial Sequence
<220> FEATURE:
<223> OTHER INFORMATION: IgG4 CH2 IgG1 CH3 IgM tp

<400> SEQUENCE: 43

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
            35                  40                  45

Gln Phe Asn Trp Tyr Val Asp Gly Val Glu Val His Asn Ala Lys Thr
50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
            85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
            115                 120                 125

Ser Arg Asp Glu Leu Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gly Asn Val Phe Ser Cys Ser Val Met His Glu Ala Leu His
    195                 200                 205

Asn His Tyr Thr Gln Lys Ser Leu Ser Leu Ser Pro Gly Lys Pro Thr
210                 215                 220

Leu Tyr Asn Val Ser Leu Val Met Ser Asp Thr Ala Gly Thr Cys Tyr
225                 230                 235                 240

<210> SEQ ID NO 44
<211> LENGTH: 240
<212> TYPE: PRT
<213> ORGANISM: Artificial Sequence
<220> FEATURE:
<223> OTHER INFORMATION: IgG4 CH2 / IgG1 CH3 hybrid F234L

<400> SEQUENCE: 44

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys Pro Thr
    210                 215                 220

Leu Tyr Asn Val Ser Leu Val Met Ser Asp Thr Ala Gly Thr Cys Tyr
225                 230                 235                 240

<210> SEQ ID NO 45
<211> LENGTH: 240
<212> TYPE: PRT
<213> ORGANISM: Artificial Sequence
<220> FEATURE:
<223> OTHER INFORMATION: IgG4 CH2 / IgG1 CH3 hybrid G327A S331P

<400> SEQUENCE: 45

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro

```
              20                  25                  30
Glu Val Thr Cys Val Val Val Asp Val Ser Gln Glu Asp Pro Glu Val
         35                  40                  45
Gln Phe Asn Trp Tyr Val Asp Gly Val Glu Val His Asn Ala Lys Thr
     50                  55                  60
Lys Pro Arg Glu Glu Gln Phe Asn Ser Thr Tyr Arg Val Val Ser Val
65                  70                  75                  80
Leu Thr Val Leu His Gln Asp Trp Leu Asn Gly Lys Glu Tyr Lys Cys
                 85                  90                  95
Lys Val Ser Asn Lys Ala Leu Pro Ser Pro Ile Glu Lys Thr Ile Ser
            100                 105                 110
Lys Ala Lys Gly Gln Pro Arg Glu Pro Gln Val Tyr Thr Leu Pro Pro
        115                 120                 125
Ser Arg Asp Glu Leu Thr Lys Asn Gln Val Ser Leu Thr Cys Leu Val
    130                 135                 140
Lys Gly Phe Tyr Pro Ser Asp Ile Ala Val Glu Trp Glu Ser Asn Gly
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Lys Leu Thr Val Asp Lys Ser Arg Trp
            180                 185                 190
Gln Gln Gly Asn Val Phe Ser Cys Ser Val Met His Glu Ala Leu His
        195                 200                 205
Asn His Tyr Thr Gln Lys Ser Leu Ser Leu Ser Pro Gly Lys Pro Thr
    210                 215                 220
Leu Tyr Asn Val Ser Leu Val Met Ser Asp Thr Ala Gly Thr Cys Tyr
225                 230                 235                 240

<210> SEQ ID NO 46
<211> LENGTH: 240
<212> TYPE: PRT
<213> ORGANISM: Artificial Sequence
<220> FEATURE:
<223> OTHER INFORMATION: IgG4 CH2 / IgG1 CH3 hybrid F234L F296Y

<400> SEQUENCE: 46

Cys Pro Pro Cys Pro Ala Pro Glu Leu Leu Gly Gly Pro Ser Val Phe
1               5                  10                  15
Leu Phe Pro Pro Lys Pro Lys Asp Thr Leu Met Ile Ser Arg Thr Pro
            20                  25                  30
Glu Val Thr Cys Val Val Val Asp Val Ser Gln Glu Asp Pro Glu Val
        35                  40                  45
Gln Phe Asn Trp Tyr Val Asp Gly Val Glu Val His Asn Ala Lys Thr
    50                  55                  60
Lys Pro Arg Glu Glu Gln Tyr Asn Ser Thr Tyr Arg Val Val Ser Val
65                  70                  75                  80
Leu Thr Val Leu His Gln Asp Trp Leu Asn Gly Lys Glu Tyr Lys Cys
                85                  90                  95
Lys Val Ser Asn Lys Gly Leu Pro Ser Ser Ile Glu Lys Thr Ile Ser
            100                 105                 110
Lys Ala Lys Gly Gln Pro Arg Glu Pro Gln Val Tyr Thr Leu Pro Pro
        115                 120                 125
Ser Arg Asp Glu Leu Thr Lys Asn Gln Val Ser Leu Thr Cys Leu Val
    130                 135                 140
Lys Gly Phe Tyr Pro Ser Asp Ile Ala Val Glu Trp Glu Ser Asn Gly
```

```
145                 150                 155                 160
Gln Pro Glu Asn Asn Tyr Lys Thr Thr Pro Val Leu Asp Ser Asp
                165                 170                 175
Gly Ser Phe Phe Leu Tyr Ser Lys Leu Thr Val Asp Lys Ser Arg Trp
                180                 185                 190
Gln Gln Gly Asn Val Phe Ser Cys Ser Val Met His Glu Ala Leu His
            195                 200                 205
Asn His Tyr Thr Gln Lys Ser Leu Ser Leu Ser Pro Gly Lys Pro Thr
        210                 215                 220
Leu Tyr Asn Val Ser Leu Val Met Ser Asp Thr Ala Gly Thr Cys Tyr
225                 230                 235                 240

<210> SEQ ID NO 47
<211> LENGTH: 240
<212> TYPE: PRT
<213> ORGANISM: Artificial Sequence
<220> FEATURE:
<223> OTHER INFORMATION: IgG4 CH2 / IgG1 CH3 hybrid G327A S330A

<400> SEQUENCE: 47

Cys Pro Pro Cys Pro Ala Pro Glu Phe Leu Gly Gly Pro Ser Val Phe
1               5                   10                  15
Leu Phe Pro Pro Lys Pro Lys Asp Thr Leu Met Ile Ser Arg Thr Pro
            20                  25                  30
Glu Val Thr Cys Val Val Val Asp Val Ser Gln Glu Asp Pro Glu Val
        35                  40                  45
Gln Phe Asn Trp Tyr Val Asp Gly Val Glu Val His Asn Ala Lys Thr
    50                  55                  60
Lys Pro Arg Glu Glu Gln Phe Asn Ser Thr Tyr Arg Val Val Ser Val
65                  70                  75                  80
Leu Thr Val Leu His Gln Asp Trp Leu Asn Gly Lys Glu Tyr Lys Cys
                85                  90                  95
Lys Val Ser Asn Lys Ala Leu Pro Ala Ser Ile Glu Lys Thr Ile Ser
            100                 105                 110
Lys Ala Lys Gly Gln Pro Arg Glu Pro Gln Val Tyr Thr Leu Pro Pro
        115                 120                 125
Ser Arg Asp Glu Leu Thr Lys Asn Gln Val Ser Leu Thr Cys Leu Val
    130                 135                 140
Lys Gly Phe Tyr Pro Ser Asp Ile Ala Val Glu Trp Glu Ser Asn Gly
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Lys Leu Thr Val Asp Lys Ser Arg Trp
            180                 185                 190
Gln Gln Gly Asn Val Phe Ser Cys Ser Val Met His Glu Ala Leu His
        195                 200                 205
Asn His Tyr Thr Gln Lys Ser Leu Ser Leu Ser Pro Gly Lys Pro Thr
    210                 215                 220
Leu Tyr Asn Val Ser Leu Val Met Ser Asp Thr Ala Gly Thr Cys Tyr
225                 230                 235                 240

<210> SEQ ID NO 48
<211> LENGTH: 57
<212> TYPE: DNA
<213> ORGANISM: Artificial Sequence
<220> FEATURE:
<223> OTHER INFORMATION: B72.3 signal peptide
```

```
<400> SEQUENCE: 48
atggaatggt cctgggtctt cctgttttc ctttctgtca caaccggggt gcacagc      57

<210> SEQ ID NO 49
<211> LENGTH: 19
<212> TYPE: PRT
<213> ORGANISM: Artificial Sequence
<220> FEATURE:
<223> OTHER INFORMATION: B72.3 signal peptide

<400> SEQUENCE: 49

Met Glu Trp Ser Trp Val Phe Leu Phe Phe Leu Ser Val Thr Thr Gly
1               5                   10                  15

Val His Ser

<210> SEQ ID NO 50
<211> LENGTH: 720
<212> TYPE: DNA
<213> ORGANISM: Artificial Sequence
<220> FEATURE:
<223> OTHER INFORMATION: IgG1 Fc IgM tp L309

<400> SEQUENCE: 50
tgcccaccgt gcccagcacc tgaactcctg gggggaccgt cagtcttcct cttcccccca      60
aaacccaagg acaccctcat gatctcccgg acccctgagg tcacatgcgt ggtggtggac     120
gtgagccacg aagaccctga ggtcaagttc aactggtacg tggacggcgt ggaggtgcat     180
aatgccaaga caaagccgcg ggaggagcag tacaacagca cgtaccgtgt ggtcagcgtc     240
ctcaccgtcc tgcaccagga ctggctgaat ggcaaggagt acaagtgcaa ggtctccaac     300
aaagccctcc cagcccccat cgagaaaacc atctccaaag ccaaagggca gccccgagaa     360
ccacaggtgt acaccctgcc cccatcccgg gatgagctga ccaagaacca ggtcagcctg     420
acctgcctgg tcaaaggctt ctatcccagc gacatcgccg tggagtggga gagcaatggg     480
cagccggaga caactacaa gaccacgcct cccgtgctgg actccgacgg ctccttcttc     540
ctctacagca agctcaccgt ggacaagagc aggtggcagc aggggaacgt cttctcatgc     600
tccgtgatgc atgaggctct gcacaaccac tacacgcaga agagcctctc cctgtctccg     660
ggtaaaccga ccctgtataa cgtgagcctg gtgatgagcg ataccgcggg cacctgctat     720

<210> SEQ ID NO 51
<211> LENGTH: 720
<212> TYPE: DNA
<213> ORGANISM: Artificial Sequence
<220> FEATURE:
<223> OTHER INFORMATION: IgG4 Fc IgM tp L309

<400> SEQUENCE: 51
tgtccacctt gtccagctcc tgagtttctt ggcggtcctt ctgtgttcct cttccctcca      60
aagcctaagg acaccctgat gatctccaga acaccagaag tgacctgcgt ggtagtggat     120
gttagccagg aagaccctga ggtccagttc aactggtatg tggacggcgt tgaggtccat     180
aacgccaaaa ccaagccacg agaggagcag ttcaactcaa cctaccgtgt ggtgtctgtg     240
ctcactgtcc tgcatcagga ttggctgaac ggcaaggagt acaagtgcaa ggtcagcaac     300
aagggactgc caagctccat cgagaagacc attagcaaag ccaagggtca gcctagggaa     360
ccacaggtgt atacattgcc tcccctcacag gaggagatga ccaagaacca ggtcagtctg     420
acatgcctgg tgaaagggtt ctatccctcc gatatcgcag tcgaatggga aagcaatggc     480
```

```
cagcctgaga acaactacaa aaccactcca cccgtccttg atagcgatgg cagtttcttc    540
ctgtacagcc gtctgactgt ggataagtct cgatggcagg agggtaacgt attcagctgc    600
agcgtcatgc atgaagcctt gcacaaccac tacacccaga atccctgtc tctgtcactc     660 gggaagccga ccctgtataa cgtgagcctg gtgatgagcg ataccgcggg cacctgctat    720
```

<210> SEQ ID NO 52
<211> LENGTH: 720
<212> TYPE: DNA
<213> ORGANISM: Artificial Sequence
<220> FEATURE:
<223> OTHER INFORMATION: IgG1 Fc IgM tp L309 L234F P331S

<400> SEQUENCE: 52

```
tgcccaccgt gcccagcacc tgaattcctg gggggaccgt cagtcttcct cttccccca    60 aaacccaagg acaccctcat gatctcccgg acccctgagg tcacatgcgt ggtggtggac    120
gtgagccacg aagaccctga ggtcaagttc aactggtacg tggacggcgt ggaggtgcat    180
aatgccaaga caaagccgcg ggaggagcag tacaacagca cgtaccgtgt ggtcagcgtc    240
ctcaccgtcc tgcaccagga ctggctgaat ggcaaggagt acaagtgcaa ggtctccaac    300
aaagccctcc cagccagcat cgagaaaacc atctccaaag ccaaagggca gccccgagaa    360
ccacaggtgt acaccctgcc cccatcccgg gatgagctga ccaagaacca ggtcagcctg    420
acctgcctgg tcaaaggctt ctatcccagc gacatcgccg tggagtggga gagcaatggg    480
cagccggaga acaactacaa gaccacgcct cccgtgctgg actccgacgg ctccttcttc    540
ctctacagca agctcaccgt ggacaagagc aggtggcagc aggggaacgt cttctcatgc    600
tccgtgatgc atgaggctct gcacaaccac tacacgcaga agagcctctc cctgtctccg    660
ggtaaaccga ccctgtataa cgtgagcctg gtgatgagcg ataccgcggg cacctgctat    720
```

<210> SEQ ID NO 53
<211> LENGTH: 720
<212> TYPE: DNA
<213> ORGANISM: Artificial Sequence
<220> FEATURE:
<223> OTHER INFORMATION: Hybrid Fc IgG4-CH2 IgG1-CH3 IgM tp L309

<400> SEQUENCE: 53

```
tgcccaccgt gcccagcacc tgagttcctg gggggaccat cagtcttcct gttcccccca    60
aaacccaagg acactctcat gatctcccgg acccctgagg tcacgtgcgt ggtggtggac    120
gtgagccagg aagaccccga ggtccagttc aactggtacg tggatggcgt ggaggtgcat    180
aatgccaaga caaagccgcg ggaggagcag ttcaacagca cgtaccgtgt ggtcagcgtc    240
ctcaccgtcc tgcaccagga ctggctgaac ggcaaggagt acaagtgcaa ggtctccaac    300
aaaggcctcc cgtcctccat cgagaaaacc atctccaaag ccaaagggca gccccgagaa    360
ccacaggtgt acaccctgcc cccatcccgg gatgagctga ccaagaacca ggtcagcctg    420
acctgcctgg tcaaaggctt ctatcccagc gacatcgccg tggagtggga gagcaatggg    480
cagccggaga acaactacaa gaccacgcct cccgtgctgg actccgacgg ctccttcttc    540
ctctacagca agctcaccgt ggacaagagc aggtggcagc aggggaacgt cttctcatgc    600
tccgtgatgc atgaggctct gcacaaccac tacacgcaga agagcctctc cctgtctccg    660
ggtaaaccga ccctgtataa cgtgagcctg gtgatgagcg ataccgcggg cacctgctat    720
```

<210> SEQ ID NO 54

-continued

<211> LENGTH: 720
<212> TYPE: DNA
<213> ORGANISM: Artificial Sequence
<220> FEATURE:
<223> OTHER INFORMATION: IgG4 Fc IgM tp L309 F234L

<400> SEQUENCE: 54

| | | |
|---|---|---|
| tgtccacctt gtccagctcc tgagttactt ggcggtcctt ctgtgttcct cttccctcca | 60 |
| aagcctaagg acaccctgat gatctccaga acaccagaag tgacctgcgt ggtagtggat | 120 |
| gttagccagg aagaccctga ggtccagttc aactggtatg tggacggcgt tgaggtccat | 180 |
| aacgccaaaa ccaagccacg agaggagcag ttcaactcaa cctaccgtgt ggtgtctgtg | 240 |
| ctcactgtcc tgcatcagga ttggctgaac ggcaaggagt acaagtgcaa ggtcagcaac | 300 |
| aagggactgc caagctccat cgagaagacc attagcaaag ccaagggtca gcctagggaa | 360 |
| ccacaggtgt atacattgcc tccctcacag gaggagatga ccaagaacca ggtcagtctg | 420 |
| acatgcctgg tgaaagggtt ctatccctcc gatatcgcag tcgaatggga aagcaatggc | 480 |
| cagcctgaga caactacaa aaccactcca cccgtccttg atagcgatgg cagtttcttc | 540 |
| ctgtacagcc gtctgactgt ggataagtct cgatggcagg agggtaacgt attcagctgc | 600 |
| agcgtcatgc atgaagcctt gcacaaccac tacacccaga atccctgtc tctgtcactc | 660 |
| gggaagccga ccctgtataa cgtgagcctg gtgatgagcg ataccgcggg cacctgctat | 720 |

<210> SEQ ID NO 55
<211> LENGTH: 720
<212> TYPE: DNA
<213> ORGANISM: Artificial Sequence
<220> FEATURE:
<223> OTHER INFORMATION: IgG4 Fc IgM tp L309 F234L F296Y

<400> SEQUENCE: 55

| | | |
|---|---|---|
| tgtccacctt gtccagctcc tgagttactt ggcggtcctt ctgtgttcct cttccctcca | 60 |
| aagcctaagg acaccctgat gatctccaga acaccagaag tgacctgcgt ggtagtggat | 120 |
| gttagccagg aagaccctga ggtccagttc aactggtatg tggacggcgt tgaggtccat | 180 |
| aacgccaaaa ccaagccacg agaggagcag tataactcaa cctaccgtgt ggtgtctgtg | 240 |
| ctcactgtcc tgcatcagga ttggctgaac ggcaaggagt acaagtgcaa ggtcagcaac | 300 |
| aagggactgc caagctccat cgagaagacc attagcaaag ccaagggtca gcctagggaa | 360 |
| ccacaggtgt atacattgcc tccctcacag gaggagatga ccaagaacca ggtcagtctg | 420 |
| acatgcctgg tgaaagggtt ctatccctcc gatatcgcag tcgaatggga aagcaatggc | 480 |
| cagcctgaga caactacaa aaccactcca cccgtccttg atagcgatgg cagtttcttc | 540 |
| ctgtacagcc gtctgactgt ggataagtct cgatggcagg agggtaacgt attcagctgc | 600 |
| agcgtcatgc atgaagcctt gcacaaccac tacacccaga atccctgtc tctgtcactc | 660 |
| gggaagccga ccctgtataa cgtgagcctg gtgatgagcg ataccgcggg cacctgctat | 720 |

<210> SEQ ID NO 56
<211> LENGTH: 720
<212> TYPE: DNA
<213> ORGANISM: Artificial Sequence
<220> FEATURE:
<223> OTHER INFORMATION: IgG4 Fc IgM tp L309 G327A S330A

<400> SEQUENCE: 56

| | | |
|---|---|---|
| tgtccacctt gtccagctcc tgagtttctt ggcggtcctt ctgtgttcct cttccctcca | 60 |
| aagcctaagg acaccctgat gatctccaga acaccagaag tgacctgcgt ggtagtggat | 120 |

```
gttagccagg aagaccctga ggtccagttc aactggtatg tggacggcgt tgaggtccat      180
aacgccaaaa ccaagccacg agaggagcag ttcaactcaa cctaccgtgt ggtgtctgtg      240
ctcactgtcc tgcatcagga ttggctgaac ggcaaggagt acaagtgcaa ggtcagcaac      300
aaggcactgc cagcctccat cgagaagacc attagcaaag ccaagggtca gcctagggaa      360
ccacaggtgt atacattgcc tccctcacag gaggagatga ccaagaacca ggtcagtctg      420
acatgcctgg tgaaagggtt ctatccctcc gatatcgcag tcgaatggga aagcaatggc      480
cagcctgaga caactacaa aaccactcca cccgtccttg atagcgatgg cagtttcttc       540
ctgtacagcc gtctgactgt ggataagtct cgatggcagg agggtaacgt attcagctgc      600
agcgtcatgc atgaagcctt gcacaaccac tacacccaga atccctgtc tctgtcactc       660 gggaagccga ccctgtataa cgtgagcctg gtgatgagcg ataccgcggg cacctgctat      720
```

<210> SEQ ID NO 57
<211> LENGTH: 720
<212> TYPE: DNA
<213> ORGANISM: Artificial Sequence
<220> FEATURE:
<223> OTHER INFORMATION: IgG4 Fc IgM tp L309 G327A S331P

<400> SEQUENCE: 57

```
tgtccacctt gtccagctcc tgagtttctt ggcggtcctt ctgtgttcct cttccctcca       60
aagcctaagg acaccctgat gatctccaga acaccagaag tgacctgcgt ggtagtggat      120
gttagccagg aagaccctga ggtccagttc aactggtatg tggacggcgt tgaggtccat      180
aacgccaaaa ccaagccacg agaggagcag ttcaactcaa cctaccgtgt ggtgtctgtg      240
ctcactgtcc tgcatcagga ttggctgaac ggcaaggagt acaagtgcaa ggtcagcaac      300
aaggcactgc caagccccat cgagaagacc attagcaaag ccaagggtca gcctagggaa      360
ccacaggtgt atacattgcc tccctcacag gaggagatga ccaagaacca ggtcagtctg      420
acatgcctgg tgaaagggtt ctatccctcc gatatcgcag tcgaatggga aagcaatggc      480
cagcctgaga caactacaa aaccactcca cccgtccttg atagcgatgg cagtttcttc       540
ctgtacagcc gtctgactgt ggataagtct cgatggcagg agggtaacgt attcagctgc      600
agcgtcatgc atgaagcctt gcacaaccac tacacccaga atccctgtc tctgtcactc       660 gggaagccga ccctgtataa cgtgagcctg gtgatgagcg ataccgcggg cacctgctat      720
```

<210> SEQ ID NO 58
<211> LENGTH: 720
<212> TYPE: DNA
<213> ORGANISM: Artificial Sequence
<220> FEATURE:
<223> OTHER INFORMATION: IgG4 Fc IgM tp L309 S330A S331P

<400> SEQUENCE: 58

```
tgtccacctt gtccagctcc tgagtttctt ggcggtcctt ctgtgttcct cttccctcca       60
aagcctaagg acaccctgat gatctccaga acaccagaag tgacctgcgt ggtagtggat      120
gttagccagg aagaccctga ggtccagttc aactggtatg tggacggcgt tgaggtccat      180
aacgccaaaa ccaagccacg agaggagcag ttcaactcaa cctaccgtgt ggtgtctgtg      240
ctcactgtcc tgcatcagga ttggctgaac ggcaaggagt acaagtgcaa ggtcagcaac      300
aagggactgc cagccccat cgagaagacc attagcaaag ccaagggtca gcctagggaa       360
ccacaggtgt atacattgcc tccctcacag gaggagatga ccaagaacca ggtcagtctg      420
```

```
acatgcctgg tgaaagggtt ctatccctcc gatatcgcag tcgaatggga aagcaatggc    480
cagcctgaga acaactacaa aaccactcca cccgtccttg atagcgatgg cagtttcttc    540
ctgtacagcc gtctgactgt ggataagtct cgatggcagg agggtaacgt attcagctgc    600
agcgtcatgc atgaagcctt gcacaaccac tacacccaga atccctgtc tctgtcactc     660 gggaagccga ccctgtataa cgtgagcctg gtgatgagcg ataccgcggg cacctgctat    720

<210> SEQ ID NO 59
<211> LENGTH: 720
<212> TYPE: DNA
<213> ORGANISM: Artificial Sequence
<220> FEATURE:
<223> OTHER INFORMATION: IgG4 CH2-IgG1 CH3 IgM tp L309 F234L F296Y

<400> SEQUENCE: 59
tgcccaccgt gcccagcacc tgagttactg gggggaccat cagtcttcct gttcccccca    60
aaacccaagg acactctcat gatctcccgg acccctgagg tcacgtgcgt ggtggtggac   120
gtgagccagg aagaccccga ggtccagttc aactggtacg tggatggcgt ggaggtgcat   180
aatgccaaga caaagccgcg ggaggagcag tataacagca cgtaccgtgt ggtcagcgtc   240
ctcaccgtcc tgcaccagga ctggctgaac ggcaaggagt acaagtgcaa ggtctccaac   300
aaaggcctcc cgtcctccat cgagaaaacc atctccaaag ccaaagggca gccccgagaa   360
ccacaggtgt acaccctgcc cccatcccgg gatgagctga ccaagaacca ggtcagcctg   420
acctgcctgg tcaaaggctt ctatcccagc gacatcgccg tggagtggga gagcaatggg   480
cagccggaga acaactacaa gaccacgcct cccgtgctgg actccgacgg ctccttcttc   540
ctctacagca agctcaccgt ggacaagagc aggtggcagc aggggaacgt cttctcatgc   600
tccgtgatgc atgaggctct gcacaaccac tacacgcaga gagcctctc cctgtctccg   660 ggtaaaccga ccctgtataa cgtgagcctg gtgatgagcg ataccgcggg cacctgctat   720
```